United States Patent

Baker et al.

[11] Patent Number: 6,060,469
[45] Date of Patent: May 9, 2000

[54] SPIRO-PIPERIDINE DERIVATIVES AND THEIR USE AS TACHYKININ ANTAGONISTS

[75] Inventors: Raymond Baker, Uley; Timothy Harrison, Great Dunmow; Christopher John Swain, Duxford; Brian John Williams, Great Dunmow, all of United Kingdom

[73] Assignee: Merck Sharp & Dohme Ltd., Hoddesdon, United Kingdom

[21] Appl. No.: 09/077,063

[22] PCT Filed: Nov. 20, 1996

[86] PCT No.: PCT/GB96/02853

§ 371 Date: May 18, 1998

§ 102(e) Date: May 18, 1998

[87] PCT Pub. No.: WO97/19084

PCT Pub. Date: May 29, 1997

[30] Foreign Application Priority Data

Nov. 23, 1995 [GB] United Kingdom .................... 9523944
Dec. 20, 1995 [GB] United Kingdom .................... 9526093
Feb. 16, 1996 [GB] United Kingdom .................... 9603239

[51] Int. Cl.[7] ........................ A61K 31/445; C07D 471/10
[52] U.S. Cl. ...................................... 514/227.8; 514/235.8; 514/241; 514/242; 514/252; 514/256; 514/278; 514/409; 544/6; 544/70; 544/180; 544/182; 544/230; 546/16; 548/409; 548/410
[58] Field of Search .............................. 546/16; 514/256, 514/278, 241, 242, 252, 227.8, 235.8; 544/230, 182, 180, 70, 6

[56] References Cited

U.S. PATENT DOCUMENTS 5,688,806 11/1997 Desai et al. .............................. 514/278
5,869,496 2/1999 Hale et al. .............................. 514/278

FOREIGN PATENT DOCUMENTS

WO 94/20500 9/1994 WIPO .
WO 94/29309 12/1994 WIPO .
97/49710 12/1997 WIPO .
98/13369 4/1998 WIPO .
98/49170 11/1998 WIPO .

*Primary Examiner*—Mukund J. Shah
*Assistant Examiner*—Ann M. Kessinger
*Attorney, Agent, or Firm*—J. Eric Thies; David L. Rose

[57] ABSTRACT

The present invention relates to compounds of formula (I),

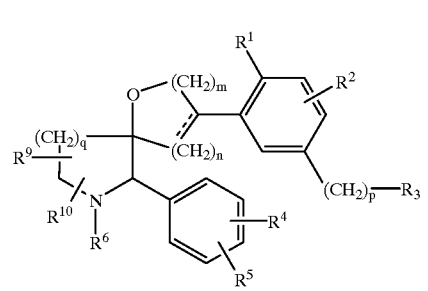

wherein $R^1$ represents halogen, hydroxy, $C_{1-6}$alkyl group optionally substituted by one or three fluorine atoms, $C_{1-6}$alkoxy group optionally substituted by one to three fluorine atoms, or $C_{1-6}$alkylthio optionally substituted by one to three fluorine atoms; $R^2$ represents hydrogen, halogen, $C_{1-6}$alkyl or $C_{1-6}$alkoxy; or when $R^2$ is adjacent to $R^1$, they may be joined together such that there is formed a 5- or 6-membered saturated or unsaturated ring containing one or two oxygen atoms; $R^3$ represents an optionally substituted 5- or 6-membered aromatic heterocyclic group containing 1, 2, 3 or 4 heteroatoms, selected from nitrogen, oxygen and sulphur; m is 0–3 and n is 0–3, with the proviso that the sum total of m+n is 2 or 3; p is zero or 1; q is 1 or 2; and when m is 1 and n is 1 or 2, the broken line represents an optional double bond; $R^4$, $R^5$, $R^6$, $R^9$ and $R^{10}$ are a variety of substituents defined in the specification; or a pharmaceutically acceptable salt thereof. The compounds are of particular use in the treatment or prevention of pain, inflammation, emesis and postherpetic neuralgia.

22 Claims, No Drawings

SPIRO-PIPERIDINE DERIVATIVES AND THEIR USE AS TACHYKININ ANTAGONISTS

This application is a 371 of PCT/GB96/02853 filed Nov. 20, 1996.

This invention relates to a class of azacyclic compounds which are useful as tachykinin antagonists. More particularly, the compounds of the invention are spiro-substituted azacyclic derivatives.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

Phe-X-Gly-Leu-Met-NH$_2$

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the NK$_1$, NK$_2$ and NK$_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem*, (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in *"Trends in Cluster Headache"* Ed. Sicuteri et al Elsevier Scientific Publishers, Amsterdam (1987) page 85)] and emesis F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIIth Congress*, Jun. 28–Jul. 2, 1992], and in disorders of bladder finction such as bladder detrusor hyper-reflexia (*Lancet.* May 16, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

International (PCT) patent specification no. WO 94/20500 (published Sep. 15, 1994) discloses spiroazacyclic derivatives as substance P antagonists. In particular, WO 94/20500 relates to spirocyclic piperidine derivatives containing a 1,8-diazaspiro[5.5]undecane core.

We have now found a further class of non-peptides which are potent antagonists of tachykinins, especially of substance P. In addition, the compounds of the present invention exhibit a high level of hepatic stability as measured by, for example, conventional liver microsome analysis.

The present invention provides compounds of the formula (I):

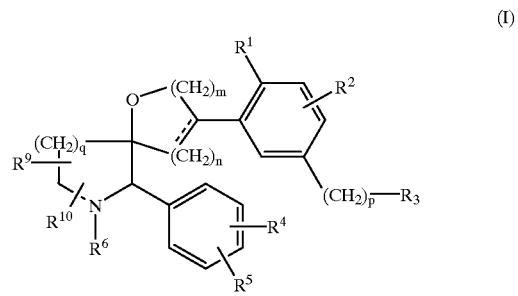

wherein

R$^1$ represents a halogen atom, a hydroxy group, a C$_{1-6}$alkyl group optionally substituted by one to three fluorine atoms, or a $C_{1-6}$alkoxy group optionally substituted by one to three fluorine atoms, or a $C_{1-6}$alkylthio group optionally substituted by one to three fluorine atoms;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two oxygen atoms;

$R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalklyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ represents hydrogen, halogen, $C_{1-6}$alkyl, $C_{1-6}$alkoxy substituted by $C_{1-4}$alkoxy or $CF_3$;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, C(NOH)$NR^aR^b$, CONHphenyl($C_{1-4}$alkyl), $COCO_2R^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —$CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^d$, oxo, $CO_2R^a$ or $CONR^aR^b$ where $R^a$ and $R^b$ are as previously defined and $R^d$ represents hydrogen, $C_{1-6}$alkyl or phenyl;

$R^{12}$ represents $OR^a$, $CONR^aR^b$ or heteroaryl;

$R^{13}$ represents H or $C_{1-6}$alkyl;

m is zero 1, 2 or 3;

n is zero, 1, 2, or 3, with the proviso that the sum total of m+n is 2 or 3;

p is zero or 1;

q is 1 or 2; and when m is 1 and n is 1 or 2, the broken line represents an optional double bond;

and pharmaceutically acceptable salts thereof.

A preferred class of compound of formula (I) is that wherein $R^1$ represents a $C_{1-6}$alkyl group optionally substituted by one to three fluorine atoms, or a $C_{1-6}$alkoxy group optionally substituted by one to three fluorine atoms.

Another preferred class of compound of formula (I) is that wherein:

$R^1$ represents a $C_{1-6}$alkyl group optionally substituted by one to three fluorine atoms, or a $C_{1-6}$alkoxy group optionally substituted by one to three fluorine atoms;

$R^2$ represents hydrogen, halogen, $C_{1-6}$alkyl or $C_{1-6}$alkoxy;

$R^3$ represents a 5- or 6-membered aromatic heterocyclic group containing 1, 2, 3 or 4 heteroatoms, selected from nitrogen, oxygen and sulphur, which group is optionally substituted by a group selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, —$(CH_2)_rNR^aR^b$, —$(CH_2)_rNR^aCOR^b$, —$(CH_2)_rCONR^aR^b$, or $CH_2C(O)R^a$, where $R^a$ and $R^b$ are each independently hydrogen or $C_{1-4}$alkyl and r is zero, 1 or 2; and $R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, C(NOH)$NR^aR^b$, CONHphenyl($C_{1-4}$alkyl), $COCO_2R^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from $C_{1-6}$alkyl, $C_{1-6}$alkoxy, halogen and trifluoromethyl) or $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z, $R^7$ and $R^8$ are as previously defined;

and pharmaceutically acceptable salts thereof.

A further preferred class of compound of the present invention is that of the formula (I')

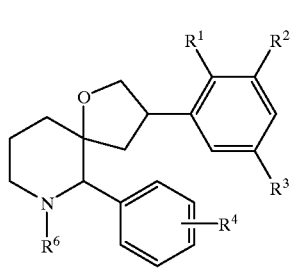

(I')

wherein $R^1$ represents a $C_{1-6}$alkyl group optionally substituted by one to three fluorine atoms, or a $C_{1-6}$alkoxy group optionally substituted by one to three fluorine atoms;

$R^2$ represents hydrogen or halogen;

$R^3$ represents an N-linked tetrazolyl group optionally substituted by a group selected from $C_{1-6}$alkyl, $C_{3-7}$cycloalkyl, $C_{3-7}$cycloalkyl$C_{1-4}$alkyl, trifluoromethyl, $SR^a$, $SOR^a$, $SO_2R^a$, phenyl, $NR^aR^b$, $NR^aCOR^b$ or $CH_2C(O)R^a$, where $R^a$ and $R^b$ are each independently hydrogen or $C_{1-4}$alkyl;

$R^4$ represents hydrogen or halogen;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl) or $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^{12}$ represents $OR^a$, $CONR^aR^b$ or heteroaryl;

$R^{13}$ represents H or $C_{1-6}$alkyl;

or a pharmaceutically acceptable salt thereof.

A particularly preferred class of compound of formula (I) is that wherein $R^1$ is a methyl, trifluoromethyl, methoxy, ethoxy, isopropoxy or trifluoromethoxy group, especially a methoxy group.

Another preferred class of compound of formula (I) is that wherein $R^2$ is a hydrogen, fluorine or chlorine atom, especially a hydrogen atom.

A further preferred class of compound of formula (I) is that wherein $R^4$ is a hydrogen atom or a fluorine atom.

Another preferred class of compound of formula (I) is that in which $R^5$ is a hydrogen atom.

Also preferred is the class of compound of formula (I) in which $R^9$ and $R^{10}$ are both hydrogen atoms.

A further preferred class of compound of formula (I) is that wherein $R^6$ is a hydrogen atom.

Also preferred is the class of compound of formula (I) in which $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from:

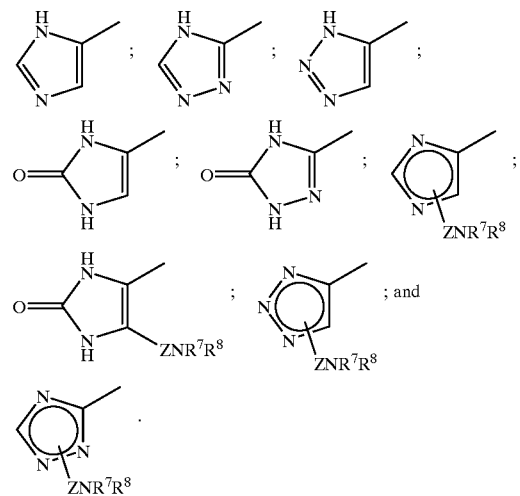

Particularly preferred heterocyclic rings are selected from:

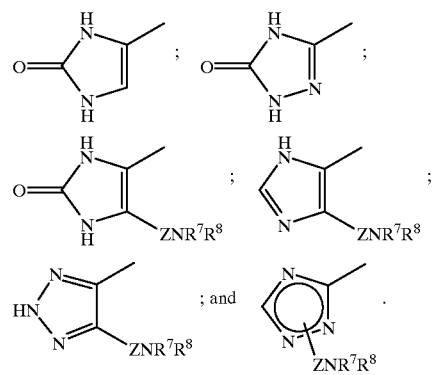

Most especially, the heterocyclic ring is selected from:

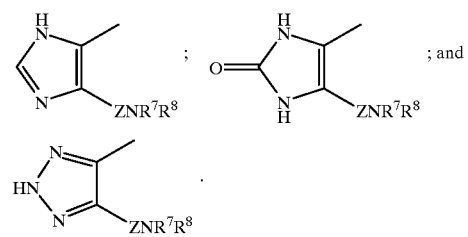

A particularly preferred heterocyclic ring is:

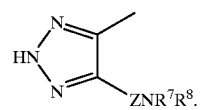

Where $R^1$ and $R^2$ are attached to adjacent carbon atoms and are joined together such that there is formed a 5- or 6-membered saturated or unsaturated ring containing one or two oxygen atoms, there is formed a fused ring moiety such as 2,3-dihydrobenzofuran, benzofuran, 3,4dihydro-2H-1-benzopyran, 2H-1-benzopyran, 1,3-benzodioxole or 1,4-benzodioxan. Particularly preferred is 2,3-dihydrobenzofuran where the oxygen atom corresponds to the position of $R^1$.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole, 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

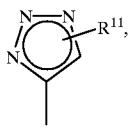

where $R^{11}$ is hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $COR^a$, $CO_2R^a$, $(CH_2)_r$ $CONR^aR^b$, $(CH_2)_rNR^aR^b$ or $(CH_2)_rNR^aCOR^b$, where $R^a$ and $R^b$ are hydrogen or $C_{1-4}$alkyl, and r is zero, 1 or 2.

Another especially preferred class of compound of formula (I) is that wherein $R^3$ is the group

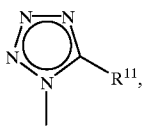

wherein $R^{11}$ is as previously defined.

$R^{11}$ is preferably hydrogen, $C_{1-4}$alkyl, especially methyl, $CF_3$, $(CH_2)_rCONR^aR^b$, $SOR^a$ or $SO_2R^a$ where $R^a$, $R^b$ and r are as previously defined.

Preferably m is 1.

Preferably n is 1 or 2, especially 1.

Preferably p is zero.

Preferably q is 2.

It will be appreciated that when the broken line represents a double bond then the group $—(CH_2)_n—$ should be interpreted as a $—(CH)_n—$ group.

One favoured group of compounds of the present invention are of the formula (Ia) and pharmaceutically acceptable salts thereof:

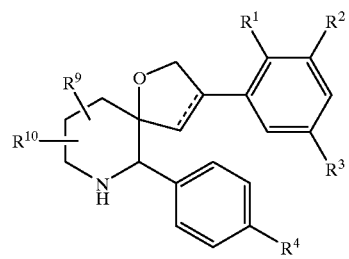

wherein $R^1$, $R^2$, $R^3$, $R^4$, $R^9$, $R^{10}$ and the broken line are as defined in relation to formula (I).

Another favoured group of compounds of the present invention are of the formula (Ib) and pharmaceutically acceptable salts thereof:

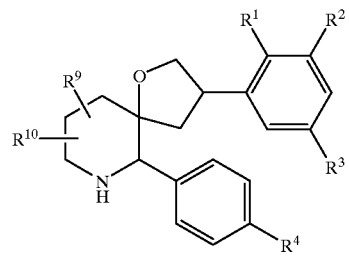

wherein $R^1$, $R^2$, $R^3$, $R^4$, $R^9$ and $R^{10}$ are as defined in relation to formula (I).

Another favoured group of compounds of the present invention are of the formula (Ic) and pharmaceutically acceptable salts thereof:

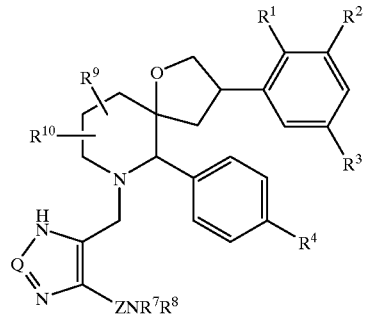

wherein $R^1$, $R^2$, $R^3$, $R^4$, $R^9$ and $R^{10}$ are defined in relation to formula (I), Q is CH or N and Z, $R^7$ and $R^8$ are as defined in relation to formula (I).

With respect to compounds of the formulae (I) and (Ic), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formulae (I) and (Ic), $R^7$ may aptly be a $C_{1-4}$alkyl group or a $C_{2-4}$alkyl group substituted by a hydroxyl or $C_{1-2}$alkoxy group, $R^8$ may aptly be a $C_{2-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino and morpholino.

In particular, $NR^7R^8$ is preferably dimethylamino, azetidinyl or pyrrolidino, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanyl, thienyl, pyridyl pyrazolyl, imidazolyl oxazolyl, isoxazolyl, thiazolyl, isothiazolyl, pyrazinyl pyrimidinyl, pyridazinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise stated.

Specific compounds within the scope of this invention include:

(6S,5R,3S)-3-(2-methoxy-5-(5-trifluoromethyl)tetrazol-1-yl)phenyl)-6-phenyl-1-oxa-7-aza-spiro[4.5]decane;
(6S,5R,3S)-3-(2-isopropoxy-5-(5-(trifluoromethyl)tetrazol-1-yl)phenyl)-6-phenyl-1-oxa-7-aza-spiro[4.5]decane;
(6S,5R,3S)-3-(2-methoxy-5-(tetrazol-1-yl)phenyl)-6-phenyl-1-oxa-7-aza-spiro[4.5]decane;
(6S,5R,3S)-3-(2-methyl-5-(5-(trifluoromethyl)tetrazol-1-yl)phenyl)-6-phenyl-1-oxa-7-aza-spiro[4.5]decane;
(6S,5R,3S)-3-(2-trifluoromethoxy-5-(5-(trifluoromethyl)tetrazol-1-yl)phenyl)-6-phenyl-1-oxa-7-aza-spiro[4.5]decane;
(6S,5R,3S)-3-(2-methoxy-3-fluoro-5-(5-(trifuoromethyl)tetrazol-1-yl)phenyl)-6-phenyl-1-oxa-7-aza-spiro[4.5]decane;
(6S, 5R, 3S)-3-(2-methoxy-5-(1,2,4-triazol-4-yl)phenyl)-6-phenyl-1-oxa-7-aza-spiro[4.5]decane;
(6S,5R,3S)-3-(2-methoxy-4-fluoro-5-(5-(trifluoromethyl)tetrazol-1-yl)phenyl)-6-phenyl-1-oxa-7-aza-spiro[4.5]decane;
(6S,5R,3S)-6-phenyl-3-(2-methoxy-5-(3,5-bis(trifluoromethyl)-1,2,4-triazol-4-yl)phenyl)-1-oxa-7-aza-spiro[4.5]dec-3-ene;
(6S,5R,3S)-6-phenyl-3-(5-(5-trifluoromethyl)tetrazol-1-yl)-2,3-dihydrobenzfuran-7-yl)-1-oxa-7-aza-spiro[4.5]decane;
(6S,5R,3S)-6-phenyl-3-(5-(5-trifluoromethyl)tetrazol-1-yl)-2,3-dihydrobenzfuran-7-yl)-1-oxa-7-aza-spiro[4.5]dec-3-ene;
(6S,5R,3S)-6-phenyl-3-(2-methoxy-5-(3,5-bis(trifluoromethyl)-1,2,4-triazol-4-yl)phenyl)-1-oxa-7-aza-spiro[4.5]decane;
(6S, 5R, 3S)-6-phenyl-3-(2-methoxy-5-(5-trifluoromethyl)isoxazol-4-yl)phenyl)-1-oxa-7-aza-spiro[4.5]dec-3-ene;
(6S, 5R,3S)-6-phenyl-3-(2-methoxy-5-(5-trifluoromethyl)isoxazol-4-yl)phenyl)-1-oxa-7-aza-spiro[4.5]decane;
(6S,5R,3S)-7-((2,3-dihydro-3-oxo-1,2,4-triazol-5-yl)methyl)-3-(2-methoxy-5-(5-(trifluoromethyl)tetrazol-1-yl)phenyl)-6-phenyl-1-oxa-7-aza-spiro[4.5]decane;
(6S,5R,3S)-7-(2-(N,N-dimethylamino)ethyl)-3-(2-methoxy-5-(5-(trifluoromethyl)tetrazol-1-yl)phenyl)-6-phenyl-1-oxa-7-aza-spiro[4.5]decane;
(6S,5R,3S)-7-((1H-imidazol-5-yl)methyl)-3-(2-methoxy-5-(5-(trifluoromethyl)tetrazol-1-yl)phenyl)-6-phenyl-1-oxa-7-aza-spiro[4.5]decane;

and pharmaceutically acceptable salts thereof.

Further preferred compounds of the present invention include:

(5R,6S)-3-[2-methoxy-5-(2,4-dimethyl-1H-imidazol-1-yl)phenyl]-6-phenyl-1-oxa-7-(tert-butoxycarbonyl)aza-spiro[4.5]dec-3-ene;
(5R,6S)-3-[2-methoxy-5-(2,4-dimethyl-1H-imidazol-1-yl)phenyl]-6-phenyl-1-oxa-7-aza-spiro[4.5]dec-3-ene;
(3S,5R,6S)-3-[2-methoxy-5-(2,4-dimethyl-1H-imidazol-1-yl)phenyl]-6-phenyl-1-oxa-7-aza-spiro[4.5]decane;
(5R,6S)-3-[2-methoxy-5-(4-pyridyl)phenyl]-6-phenyl-1-oxa-7-(tert-butoxycarbonyl)aza-spiro[4.5]dec-3-ene;
(5R,6S)-3-[2-methoxy-5-(4-piridyl)phenyl]-6-phenyl-1-oxa-7-aza-spiro[4.5]dec-3-ene;
(3S,5R,6S)-3-[2-methoxy-5-(4-pyridyl)phenyl]-6-phenyl-1-oxa-7-aza-spiro[4.5]decane;
(5R,6S)-3-[5-(4-pyridyl)-2-(trifluoromethoxy)phenyl]-6-phenyl-1-oxa-7-(tert-butoxycarbonyl)aza-spiro[4.5]dec-3-ene;
(5R,6S)-3-[5-(4-pyridyl)-2-(trifluoromethoxy)phenly]-6-phenyl-1-oxa-7-aza-spiro[4.5]dec-3-ene;
5R,6S)-3-[5-(4H-1,2,4-triazol-4-yl)-2-(trifluoromethoxy)phenyl]-6-phenyl-1-oxa-7-(tert-butoxycarbonyl)aza-spiro[4.5]dec-3-ene;
(5R,6S)-3-[5-(4H-1,2,4-triazol-4-yl)-2-(trifluoromethoxy)phenyl]-6-phenyl-1-oxa-7-aza-spiro[4.5]dec-3-ene;
(3S,5R,6S)-3-[5-(4H-1,2,4-triazol-4-yl)-2-(trifluoromethoxy)phenyl]-6-phenyl-1-oxa-7-aza-spiro[4.5]decane;
(5R,6S)-3-[2-(trifluoromethoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;

(5R,6S)-3-[2-(trifluoromethoxy-5-(3-trifluoromethyl-4H-1,2,4-triazol-4-yl)phenyl]-6-phenyl-1-oxa-7-aza-spiro[4.5]dec-3-ene;
(3S,5R,6S)-3-[2-(trifluoromethoxy-5-(3-trifluoromethyl-4H-1,2,4-triazol-4-yl)phenyl]-6-phenyl-1-oxa-7-aza-spiro[4.5]decane;
(5R,6S)-3-[2-methoxy-5-(2-trifluoromethyl-1H-imidazol-1-yl)phenyl]-6-phenyl-1-oxa-7-(tert-butoxycarbonyl)aza-spiro[4.5]dec-3-ene;
(5R,6S)-3-[2-methoxy-5-(2-trifluoromethyl-1H-imidazol-1-yl)phenyl]-6-phenyl-1-oxa-7-aza-spiro[4.5]dec-3-ene;
(3S,5R,6S)-3-[2-methoxy-5-(2-trifluoromethyl-1H-imidazol-1yl)phenyl]-6-phenyl-1-oxa-7-aza-spiro[4.5]decane;
(5R,6S)-3-[2-trifluoromethoxy-5-(2-trifluoromethyl-1H-imidazol-1-yl)phenyl]-6-phenyl-1-oxa-7-(tert-butoxycarbonyl)aza-spiro[4.5]dec-3-ene;
(5R,6S)-3-[2-trifluoromethoxy-5-(2-trifluoromethyl-1H-imidazol-1-yl)phenyl]-6-phenyl-1-oxa-7-aza-spiro[4.5]dec-3-ene;
(3S,5R,6S)-3-[2-trifluoromethoxy-5-(2-trifluoromethyl-1H-imidazol-1-yl)phenyl]-6-phenyl-1-oxa-7-aza-spiro[4.5]decane;
(5R,6S)-3-[2-methoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;
(5R,6S)-3-[2-methoxy-5-(3-trifluoromethyl-4H-1,2,4-triazol-4-yl)phenyl]-6-phenyl-1-oxa-7-aza-spiro[4.5]dec-3-ene;
(3S,5R,6S)-3-[2-methoxy-5-(3-trifluoromethyl-4H-1,2,4-triazol-4-yl)phenyl]-6-phenyl-1-oxa-7-aza-spiro[4.5]decane;
(5R,6S)-3-[2-(2-fluoroethoxy)-5-(5-trifluoromethyl-tetrazol-1-yl)phenyl]-6-phenyl-1-oxa-7-(tert-butoxycarbonyl)aza-spiro[4.5]dec-3-ene;
(5R,6S)-3-[2-(2-fluoroethoxy)-5-(5-trifluoromethyl-tetrazol-1-yl)phenyl]-6-phenyl-1-oxa-7-aza-spiro[4.5]dec-3-ene;
(3S,5R,6S)-3-[2-(2-fluoroethoxy)-5-(5-triluoromethyl-tetrazol-1-yl)phenyl]-6-phenyl-1-oxa-7-aza-spiro[4.5]decane;
(5R,6S)-3-[2-methoxy-5-(2-methyltetrazol-5-yl)phenyl]-6-phenyl-1-oxa-7-(tert-butoxycarbonyl)aza-spiro[4.5]dec-3-ene;
(5R,6S)-3-[2-methoxy-5-(2-methyltetrazol-5-yl)phenyl]-6-phenyl-1-oxa-7-aza-spiro[4.5]dec-3-ene;
(5R,6S)-3-[2-methoxy-5-(1-methyltetrazol-5-yl)phenyl]-6-phenyl-1-oxa-7-(tert-butoxycarbonyl)aza-spiro[4.5]dec-3-ene;
(5R,6S)-3-[2-methoxy-5-(1-methyltetrazol-5-yl)phenyl]-6-phenyl-1-oxa-7-aza-spiro[4.5]dec-3-ene;
(3S,5R,6S)-3-[2-methoxy-5-(1-methyltetrazol-5-yl)phenyl]-6-phenyl-1-oxa-7-aza-spiro[4.5]decane;
(5R,6S)-3-[2-chloro-5-(tetrazol-1-yl)phenyl]-6-phenyl-1-oxa-7-(tert-butoxycarbonyl)aza-spiro[4.5]dec-3-ene;
(5R,6S)-3-[2-chloro-5-(tetrazol-1-yl)phenyl]-6-phenyl-1-oxa-7-aza-spiro[4.5]decane;
(5R,6S)-3-[5-(1H-pyrazol-1-yl)-2-(trifluoromethoxy)phenyl]-6-phenyl-1-oxa-7-(tert-butoxycarbonyl)aza-spiro[4.5]dec-3-ene;
(5R,6S)-3-[5-(1H-pyrazol-1-yl)-2-(trifluoromethoxy)phenyl]-6-phenyl-1-oxa-7-aza-spiro[4.5]dec-3-ene;
(5R,6S)-3-[2-ethoxy-5-(2-trifluoromethyl-1H-imidazol-1-yl)phenyl]-6-phenyl-1-oxa-7-(tert-butoxycarbonyl)aza-spiro[4.5]dec-3-ene:
(5R,6S)-3-[2-ethoxy-5-(2-trifluoromethyl-1H-imidazol-1-yl)phenyl]-6-phenyl-1-oxa-7-aza-spiro[4.5]dec-3-ene;
(3S,5R,6S)-3-[2-ethoxy-5-(1H-imidazol-1-yl)phenyl]-6-phenyl-1-oxa-7-aza-spiro[4.5]decane;
(5R,6S)-3-[2-isopropoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;
(5R,6S)-3-[2-isopropoxy-5-(3-trifluoromethyl-4H-1,2,4-triazol-4-yl)phenyl]-6-phenyl-1-oxa-7-aza-spiro[4.5]dec-3-ene;
(3S,5R,6S)-3-[2-isopropoxy-5-(3-trifluoromethyl-4H-1,2,4-triazol-4-yl)phenyl]-6-phenyl-1-oxa-7-aza-spiro[4.5]decane;
(5R,6S)-3-[2-isopropoxy-5-(2-trifluoromethyl-1H-imidazol-1-yl)phenyl]-6-phenyl-1-oxa-7-(tert-butoxycarbonyl)aza-spiro[4.5]dec-3-ene;
(5R,6S)-3-[2-isopropoxy-5-(2-trifluoromethyl-1H-imidazol-1-yl)phenyl]-6-phenyl-1-oxa-7-azaspiro[4.5]dec-3-ene;
(3S,5R,6S)-3-[2-isopropoxy-5-(2-trifluoromethyl-1H-imidazol-1-yl)phenyl]-6-phenyl-1-oxa-7-aza-spiro[4.5]decane;
(5R,6S)-3-[2-methoxy-5-(oxazol-5-yl)phenyl]-6-phenyl-1-oxa-7-(tert-butoxycarbonyl)aza-spiro[4.5]dec-3-ene;
(5R,6S)-3-[2-methoxy-5-(oxazol-5-yl)phenyl]-6-phenyl-1-oxa-7-aza-spiro[4.5]dec-3-ene;
(3S,5R,6S)-3-[2-methoxy-5-(oxazol-5-yl)phenyl]-6-phenyl-1-oxa-7-aza-spiro[4.5]decane;
(5R,6S)-3-[2-isopropoxy-5-(oxazol-5-yl)phenyl]-6-phenyl-1-oxa-7-(tert-butoxycarbonyl)aza-spiro[4.5]dec-3-ene;
(5R,6S)-3-[2-isopropoxy-5-(oxazol-5-yl)phenyl]-6-phenyl-1-oxa-7-aza-spiro[4.5]dec-3-ene;
(3S,5R,6S)-3-[2-isopropoxy-5-(oxazol-5-yl)phenyl]-6-phenyl-1-oxa-7-aza-spiro[4.5]decane;
(5R,6S)-3-[2-benzyloxy-5-(2-trifluoromethyl-1H-imidazol-1-yl)phenyl]-6-phenyl-1-oxa-7-(tert-butoxycarbonyl)aza-spiro[4.5]dec-3-ene,
(5R,6S)-3-[2-benzyloxy-5-(2-trifluoromethyl-1H-imidazol-1-yl)phenyl]-6-phenyl-1-oxa-7-aza-spiro[4.5]dec-3-ene;
(3S,5R,6S)-3-[2-hydroxy-5-(2-trifluoromethyl-1H-imidazol-1-yl)phenyl]-6-phenyl-1-oxa-7-aza-spiro[4.5]decane;
(5R,6S)-3-[5-(1-methyl-1H-1,2,3-triazol-3-yl)-2-(trifluoromethoxy)phenyl]-6-phenyl-1-oxa-7-(tert-butoxycarbonyl)aza-spiro[4.5]dec-3-ene;
(5R,6S)-3-[5-(1-methyl-1H-1,2,3-triazol-3-yl)-2-(trifluoromethoxy)phenyl]-6-phenyl-1-oxa-7-aza-spiro[4.5]dec-3-ene;
(3S,5R,6S)-3-[5-(1-methyl-1H-1,2,3-triazol-3-yl)-2-(trifluoromethoxy)phenyl]-6-phenyl-1-oxa-7-aza-spiro[4.5]decane;
(5R,6S)-3-[5-(2-methyl-2H-1,2,3-triazol-3-yl)-2-(trifluoromethoxy)phenyl]-6-phenyl-1-oxa-7-(tert-butoxycarbonyl)aza-spiro[4.5]dec-3-ene;
(5R,6S)-3-[5-(2-methyl-2H-1,2,3-triazol-3-yl)-2-(trifluoromethoxy)phenyl]-6-phenyl-1-oxa-7-aza-spiro[4.5]dec-3-ene;
(3S,5R,6S)-3-[5-(2-methyl-2H-1,2,3-triazol-3-yl)-2-(trifluoromethoxy)phenyl]-6-phenyl-1-oxa-7-aza-spiro[4.5]decane;
(5R,6S)-3-[5-(pyrid-3-yl)-2-(trifluoromethoxy)phenyl]-6-phenyl-1-oxa-7-(tert-butoxycarbonyl)aza-spiro[4.5]dec-3-ene;
(5R,6S)-3-[5-(pyrid-3-yl)-2-(trifluoromethoxy)phenyl]-6-phenyl-1-oxa-7-aza-spiro[4.5]dec-3-ene;
(3S,5R,6S)-3-[2-isopropoxy-5-(pyrid-3-yl)phenyl]-6-phenyl-1-oxa-7-(tert-butoxycarbonyl)aza-spiro[4.5]dece;
(3S,5R,6S)-3-[2-isopropoxy-5-(pyrid-3-yl)phenyl]-6-phenyl-1-oxa-7-aza-spiro[4.5]decane;
(5R,6S)-3-[2-methoxy-5-(1H-1,2,4-triazol-1-yl)phenyl]-6-phenyl-1-oxa-7-(tert-butoxycarbonyl)aza-spiro[4.5]dec-3-ene;

(5R,6S)-3-[2-methoxy-5-(1H-1,2,4-triazol-1-yl)phenyl]-6-phenyl-1-oxa-7-aza-spiro[4.5]dec-3-ene;

(3S,5R,6S)-3-[2-methoxy-5-(1H-1,2,4triazol-1-yl)phenyl]-6-phenyl-1-oxa-7-aza-spiro[4.5]decane;

(5R,6S)-3-[5-(pyrimidin-5-yl)-2-(trifluoromethoxy)phenyl]-6-phenyl-1-oxa-7-(tert-butoxycarbonyl)aza-spiro[4.5]dec-3-ene;

(5R,6S)-3-[5-(pyrimidin-5-yl)-2-(trifluoromethoxy)phenyl]-6-phenyl-1-oxa-7-aza-spiro[4.5]dec-3-ene;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The compounds of the formula (I), (Ia), (Ib) and (Ic) will have the preferred stereochemistry of the 5-, 6-positions that is possessed by the compound of Example 2 (i.e. 5-(R) and 6-(S)). Thus for example as shown in formula (Id)

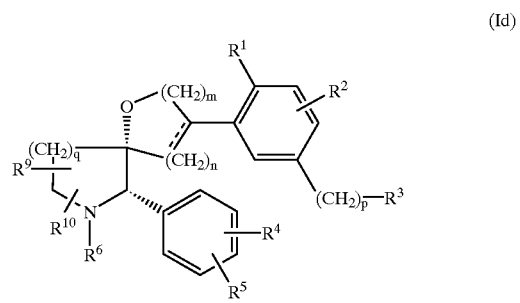

(Id)

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a premixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder: anxiety disorders, such as panic disorder with or without agoraphobia, agoraphobia without history of panic disorder. specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the ALzheimer's type, vascular dementia, and other dementias, for example, due to HIV disease, head trauma, Parkinson's disease, Huntington's disease, Pick's disease, Creutzfeldt-Jalob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A Aither aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.,* (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neumopathy, such as diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodeiator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4.859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, $\alpha$-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan. gepirone and ipsaperone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention in which m is 1 and n is 1 or 2, may be prepared by the reduction of a compound of formula (I) in which the broken line represents a double bond, hereinafter referred to as a compound of formula (II)

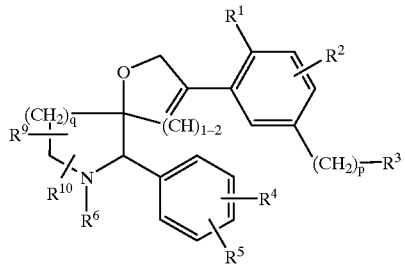

(II)

wherein $R^1$, $R^2$, $R^3$, $R^4$, $R^5$, $R^6$, $R^9$, $R^{10}$, p and q are as defined in relation to formula (I).

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof.

According to another general process (B), compounds of formula (I) may be prepared by the interconversion of a corresponding compound of formula (I) in which $R^6$ is H, hereinafter referred to as formula (III)

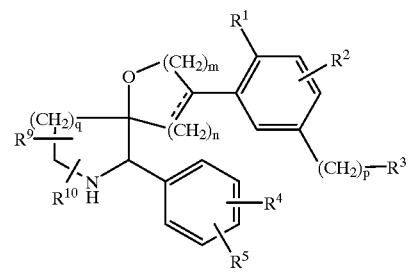

(III)

wherein $R^1$, $R^2$, $R^3$, $R^4$, $R^5$, $R^9$, $R^{10}$, m, n, p, q and the broken line are as defined in relation to formula (I) by reaction with a compound of formula (IV):

$$LG\text{—}R^{6a} \qquad (IV)$$

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another process (C), compounds of formula (I) wherein $R^6$ represents a 1,2,3-triazol-4ylmethyl group substituted by $CH_2NR^7R^8$, may be prepared by reaction of a compound of formula (V)

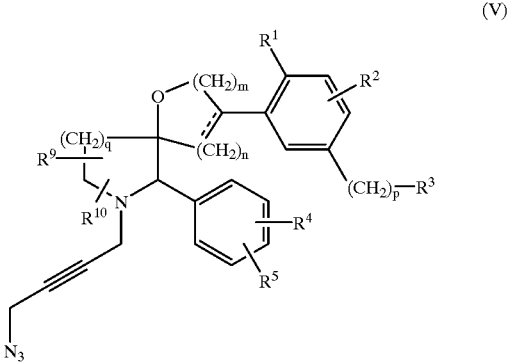

(V)

with an amine of formula $NHR^7R^8$ in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to a further process (D), compounds of formula (I) wherein $R^6$ represents a $C_{1-6}$alkyl group which is substituted by an unsubstituted or substituted 1,2,4-triazolyl group, may be prepared by reaction of an intermediate of formula (III) with a compound of formula (VI)

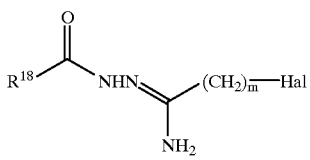

(VI)

wherein Hal is a halogen atom, for example, bromine, chlorine or iodine, m is an integer from 1 to 6 and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to a further process (E), compounds of formula (I) may be prepared by further interconversion processes from other compounds of formula (I) using suitable procedures. In particular, processes may be used to vary the group $R^6$. For example, compounds of formula (I) wherein $R^6$ is other than H may be prepared from the corresponding compounds of formula (I) wherein $R^6$ is H by reaction with a reagent suitable to introduce the group $R^6$, for example, compounds of formula (I) wherein $R^6$ is $COR^a$ may be prepared from compounds of formula (I) wherein $R^6$ is H by, for example, reaction with an appropriate acid anhydride.

Compounds of formula (I) wherein $R^6$ is $C_{1-6}$alkyl may be prepared from corresponding compounds of formula (I) wherein $R^6$ is $COR^a$ by reduction using, for example, borane or a borohydride such as sodium cyanoborohydride.

Compounds of formula (I) wherein $R^6$ is $C_{1-6}$alkyl substituted by $CONR^aR^b$ may be prepared from corresponding compounds of formula (I) wherein $R^6$ is $C_{1-6}$alkyl substituted by $CO_2R^a$ by treatment with ammonia or an amine of formula $NR^aR^b$.

Compounds of formula (I) wherein $R^6$ is $C_{1-6}$alkyl substituted by 5-oxadiazolyl may be prepared from compounds of formula (I) wherein $R^6$ is $C_{1-6}$alkyl substituted by $CO_2R^a$, where $R^a$ represents $C_{1-6}$alkyl, by reaction with a compound of formula (VII)

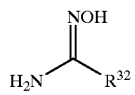

(VII)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^6$ is $C_{1-6}$alkyl substituted by thiazolyl may be prepared from compounds of formula (I) wherein $R^6$ is $C_{1-6}$alkyl substituted by $CSNH_2$ by reaction with a compound of formula $Hal-CH_2C(O)-R^{60}$, where Hal is a halogen atom, such as bromine, chlorine or iodine, and $R^{60}$ represents H or a suitable substituent.

Compounds of formula (I) wherein $R^6$ is $C_{1-6}$alkyl substituted by thioxotriazolyl may be prepared from compounds of formula (I) wherein $R^6$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

According to another general process (F), compounds of formula (I) wherein p is zero and $R^3$ is a tetrazol-1-yl group may be prepared by reaction of intermediates of formula (VIII)

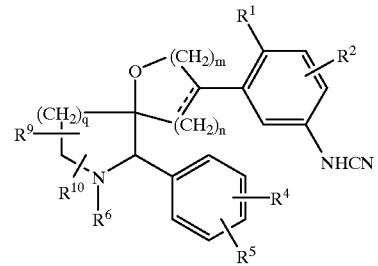

(VIII)

with ammonium chloride and sodium azide at elevated temperature, conveniently in a solvent such as dimethylformamide.

According to another general process (G), compounds of formula (I) may be prepared by a coupling reaction between a compound of formula (IX) and (X)

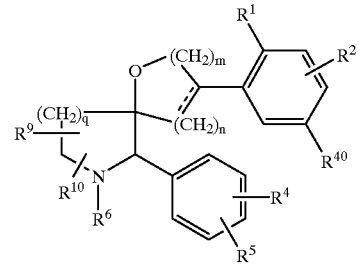

(IX)

$R^3$—$(CH_2)_p$—$R^{41}$ (X)

wherein one of $R^{40}$ and $R^{41}$ is $B(OH)_2$ or $Sn(alkyl)_3$ or a derivative thereof, and the other is a leaving group such as a halogen atom e.g. bromine or iodine, or —$OSO_2CF_3$. Where one of $R^{40}$ and $R^{41}$ is $B(OH)_2$, the reaction is conveniently effected in the presence of a palladium (0) catalyst such as tetrakis(triphenylphosphine)palladium (0) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (II) chloride, in a suitable solvent such as an aromatic hydrocarbon, for example, toluene, at an elevated temperature.

According to another general process (H), compounds of formula (I) wherein $R^6$ represents a 1,2,3-triazol-4ylmethyl group substituted by $CH_2NR^7R^8$, may be prepared by reaction of a compound of formula (XI)

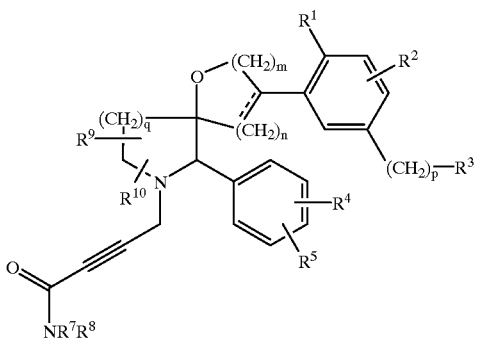

(XI)

with an azide, for example, sodium azide in a suitable solvent such as dimethylsulphoxide at a temperature of between 40° C. and 100° C. followed by reduction of the carbonyl group adjacent to —$NR^7R^8$ using a suitable reducing agent such as lithium aluminium hydride at a temperature between –10° C. and room temperature, conveniently at room temperature.

According to another general process (J), compounds of formula (I) may be prepared from a compound of formula (XXII)

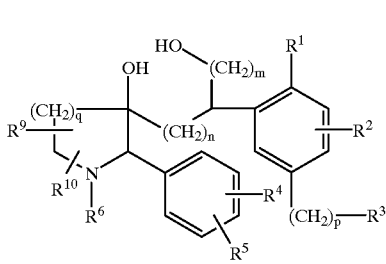

(XXII)

by an acid catalysed intramolecular cyclisation reaction.

Suitable acids of use in the reaction include mineral acids such as hydrochloric acid. The reaction is conveniently effected in a suitable organic solvent, such as an alcohol, e.g. methanol, at an elevated temperature, for example, at the reflux temperature of the chosen solvent.

According to another general process (K), compounds of formula (I) wherein $R^6$ represents the group —$CH_2C\equiv CCH_2NR^7R^8$, may be prepared from a compound of formula (XXV)

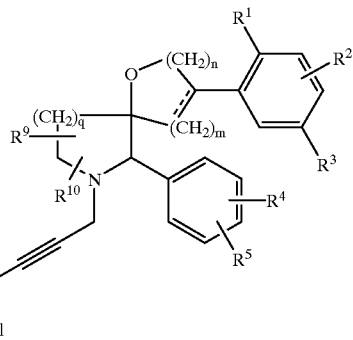

(XXV)

wherein Hal is a halogen atom such as chlorine, bromine or iodine, by reaction with an amine of formula $HNR^7R^8$ in the presence of a base.

Suitable bases of use in the reaction include alkali metal carbonates such as, for example, potassium carbonate. The reaction is conveniently effected in an organic solvent such as, for example, N,N-dimethylformamide, conveniently at room temperature.

Further details of suitable procedures will be found in the accompanying Examples.

Intermediates of formula (II) are conveniently prepared by the reaction of a compound of formula (XII)

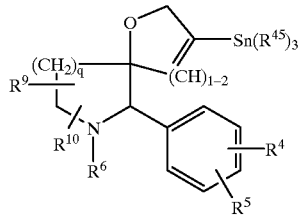

(XII)

wherein each $R^{45}$ is a $C_{1-4}$alkyl group, preferably methyl or n-butyl groups, with a compound of formula (XIII)

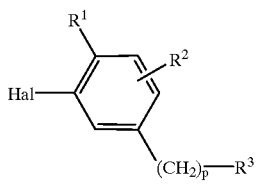

(XIII)

wherein Hal is a halogen atom, for example, chlorine, bromine or iodine, especially bromine.

The reaction is conveniently effected in the presence of lithium chloride and a transition metal catalyst such as triphenylphosphine palladium (0). Suitable solvents for the reaction include aromatic hydrocarbons, for example, toluene, the reaction being effected at a temperature between 80° C. and the reflux temperature of the solvent.

Intermediates of formula (III) may be prepared in a similar manner, preferably with an amino protecting group on the pyrrolidine/piperidine nitrogen in the compound of formula (XII). Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl.

Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonyl and benzyl groups, may also be removed by hydrogenolysis in the presence of a catalyst, for example, palladium: and trichloroethoxycarbonyl groups may be removed with zinc dust.

Intermediates of formula (V) may be prepared from a compound of formula (XIV)

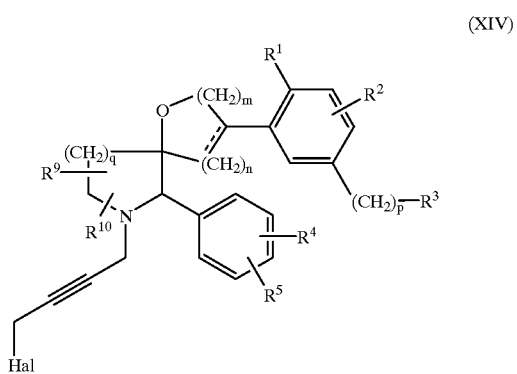

(XIV)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (XIV) may be prepared by a dropwise addition of an intermediate of formula (III) to a dihaloacetylene of formula Hal-$CH_2$—C≡C—$CH_2$-Hal where each Hal is independently chlorine, bromine or iodine, especially chlorine. The reaction is conveniently effected in a suitable solvent such as dimethylformamide in the presence of a base such as potassium carbonate.

Compounds of formula (VI) may be prepared as described in *J. Med. Chem.*, (1984) 27, 849.

Compounds of formula (XII) may be prepared from a compound of formula (XV)

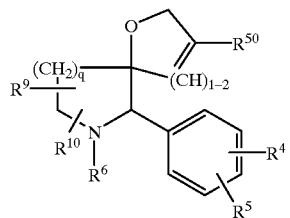

(XV)

wherein $R^{50}$ is a triflate (—$OSO_2CF_3$) group or a bromine or iodine atom, by reaction with a compound of the formula $(R^{45})_3Sn$—$Sn(R^{45})_3$, for example, hexamethyl distannane. The reaction is conveniently effected in the presence of a base, for example, lithium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (XV) may be prepared from a compound of formula (XVI):

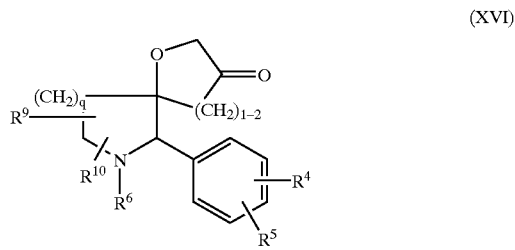

(XVI)

by enolisation of the ketone in the presence of a base, for example, sodium hexamethyldisilazide, followed by reaction with a reagent capable of introducing a suitable leaving group, for instance, where $R^{50}$ is —$OSO_2CF_3$, using 2-[N, N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (XVI) may be prepared from a compound of formula (XVII) by the following reaction sequences (Scheme A or Scheme B) or by methods analogous thereto (with the proviso that $R^9$ and $R^{10}$ are not oxo):

Scheme A

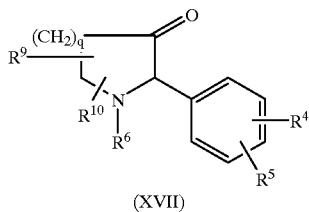

(XVII)

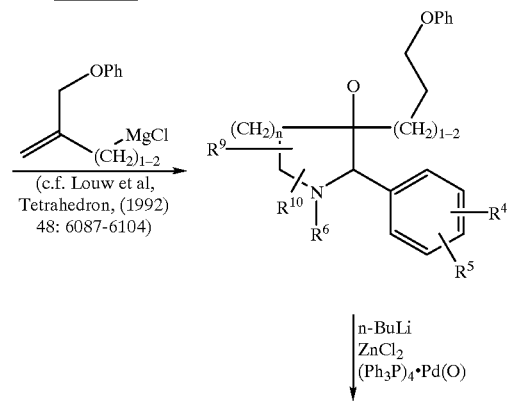

n-BuLi
$ZnCl_2$
$(Ph_3P)_4$·Pd(O)

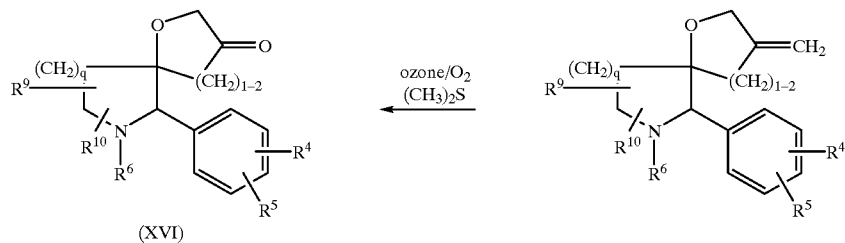
(XVI)
Scheme B
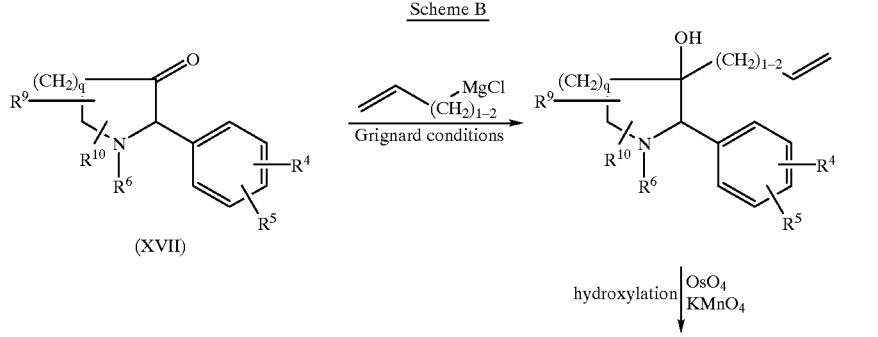
(XVII)
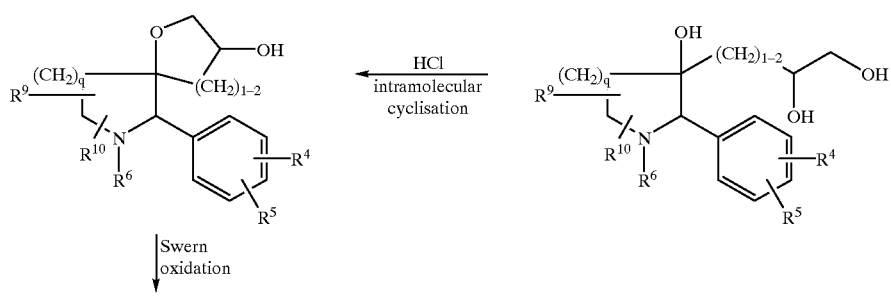
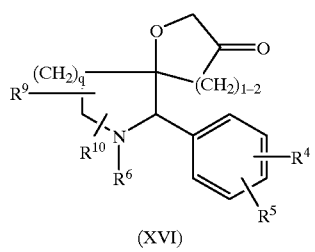
(XVI)
In an alternative method, compounds of formula (XII) may be prepared by the following reaction sequence (Scheme C) or by methods analogous thereto:

Scheme C

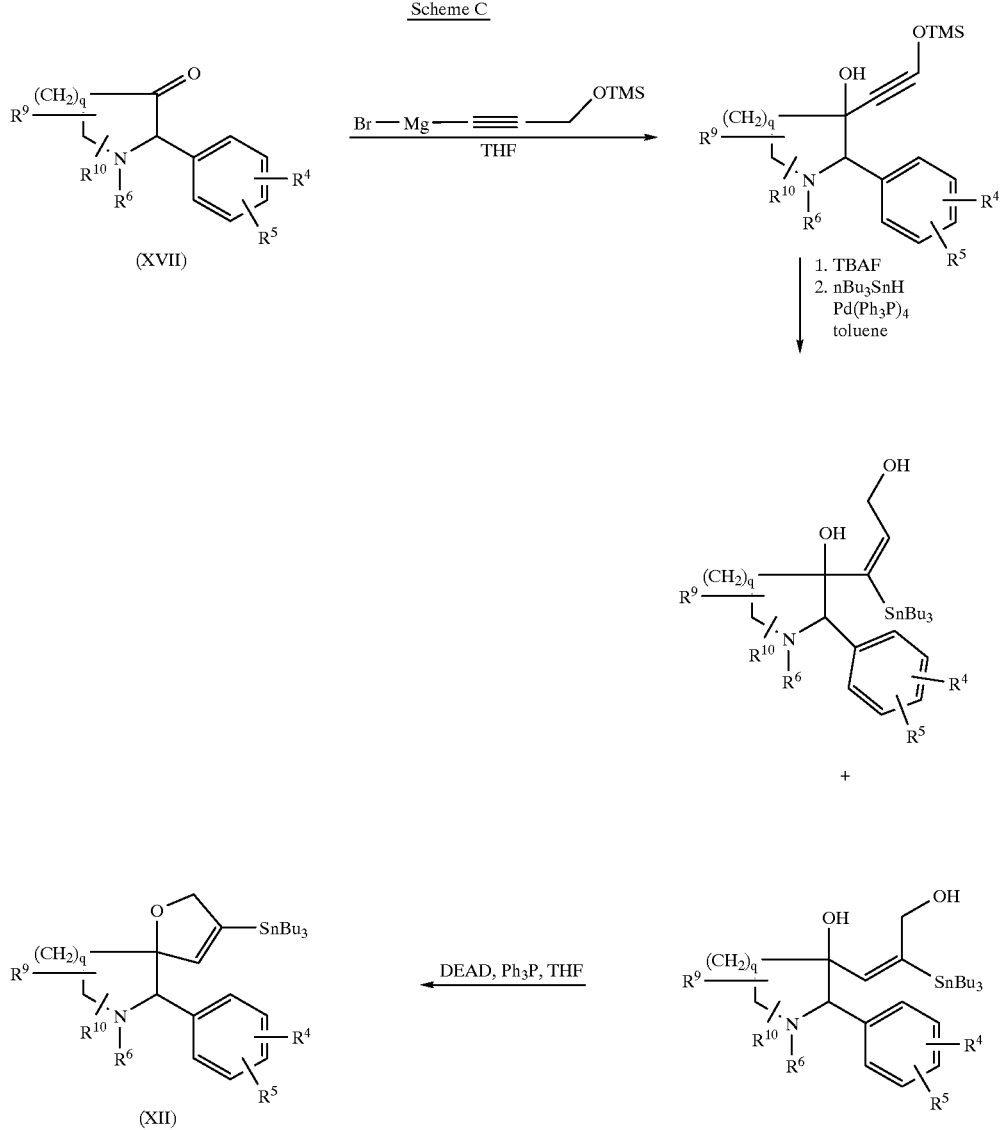

In a preferred embodiment of the aforementioned processes, $R^6$ is replaced with an amino protecting group, in particular tert-butoxycarbonyl which is conveniently removed prior to reduction of the 7-aza-spiro[4.5]dec-3-ene structure (general process (A)).

In another preferred embodiment of the aforementioned processes, $R^6$ is a benzyl group. The reduction reaction described as process (A) above for the preparation of compounds of formula (I) may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (XIII) in which p is zero and $R^3$ is an N-linked heterocyclic group may be prepared by conventional methodology, for example, from a compound of formula (XVIII)

by reaction with a suitable anhydride of the formula $(R^{60}CO)_2O$, where $R^{60}$ is hydrogen or a desired substituent for the heterocycle, followed by reaction with triphenylphosphine in carbon tetrachloride, followed by the further step of (i) reaction with an azide such as sodium azide to effect the formation of a tetrazole ring; or (ii) reaction with hydrazine hydrate to effect the formation of a 1,2,4-triazole ring; or (iii) reaction with aminoacetaldehyde diethyl acetal to effect the formation of an imidazole ring.

Compounds of formula (XVIII) may be prepared from the corresponding nitro compound by reduction using, for example, iron powder, or Raney nickel in a conventional manner.

The compounds of formula (XIII) or their nitro precursors are either known compounds or may be prepared using conventional methodology.

For compounds wherein $R^6$ is a $C_{1-6}$alkyl group substituted by a 5-membered heterocycle which in turn is substituted by a $ZNR^7R^8$ group where Z is $CH_2$, certain favoured compounds of formula (I) may be prepared from a corresponding compound with a hydrogen atom in place of the $ZNR^7R^8$. Thus, for example a compound of the formula (I) wherein $R^6$ is an imidazolinone group carrying a $CH_2NR^7R^8$ moiety may be prepared from a corresponding compound lacking the $CH_2NR^7R^8$ moiety by reaction with formaldehyde and an amine $NHR^7R^8$ under conventional Mannich reaction conditions, for example in methanol with heating. If desired a pre-formed reagent such as $R^7R^8N^+=CH_2I^-$ may be employed and a tertiary amine such as triethylamine used as acid acceptor.

Alternatively a compound of formula (I) wherein $R^6$ is a $C_{1-6}$alkyl group substituted by an imidazolinone group may be reacted with paraformaldehyde and an amine for example a secondary amine such as pyrrolidine or morpholine to give a compound wherein the imidazolinone ring is substituted by $CH_2NR^7R^8$ where $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as previously defined.

This reaction may be performed in a conventional manner, for instance, in a suitable solvent such as an alcohol for example, methanol at an elevated temperature up to the boiling point of the solvent.

A further alternative method for the preparation of certain compounds of formula (I) involves the reaction of an intermediate of formula (III) as defined above with one of the compounds of formula (XIX):

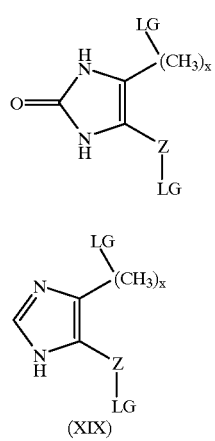

(XIX)

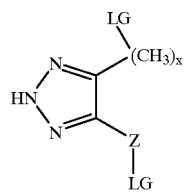

wherein each LG, which may be the same or different, is a leaving group, such as an alkyl- or arylsulphonyloxy group (e.g. mesylate or tosylate) or, in particular, a halogen atom, (e.g. bromine, chlorine or iodine), x is an integer from 1 to 6 and Z is as defined in formula (I), followed by reaction of the resultant compound with an amine $NHR^7R^8$ to complete the $ZNR^7R^8$ moiety.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (XIXa) may be protected by any suitable amine protecting group such as an acetyl group.

Compounds of formula (VIII) may be prepared by reacting a compound of formula (XX)

(XX)

with any suitable reagent for completing the $R^6$ moiety as described in any one of processes (B) to (E).

Compounds of formula (XX), and also compounds of formula (VIII), may be prepared by reaction of a compound of formula (XII) with a compound of formula (XXI)

(XXI)

according to the methods described above, followed, if desired, by reduction according to the method of general process (A).

Intermediates of formula (XXII) wherein n is 2 may be prepared by the reduction of a compound of formula (XXIII)

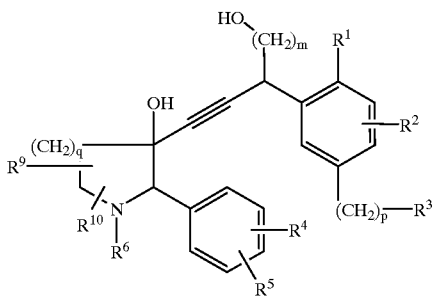

(XXIII)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

Compounds of formula (XXIII) may be prepared by the reaction of a compound of formula (XVII) with a compound of formula (XXIV)

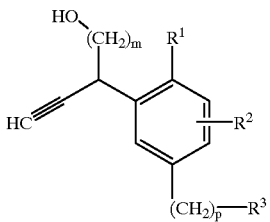

(XXIV)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at a reduced temeprature, for example, at −78° C.

Compounds of formula (XVII) may be prepared by methods described in European Patent Specification No. 0 577 394-A, or by analogous methods.

Compounds of formula (XXIV) are known compounds (see Chemische Berichte, (1988) 121, 1315–1320) or may be prepared by methods analogous to those described therein.

Intermediates of formula (V) may be prepared from a compound of formula (XXV) by reaction with an azide, for example, sodium azide in a suitable solvent such as dimethylsulphoxide at or below room temperature.

Compounds of formula (XXV) may be prepared by a dropwise addition of an intermediate of formula (III) to a dihaloacetylene of formula Hal-CH$_2$—C≡C—CH$_2$-Hal where each Hal is independentsy chlorine, bromine or iodine, especially chlorine. The reaction is conveniently effected in a suitable solvent such as dimethylformamide in the presence of a base such as potassium carbonate.

Compounds of formula (VII), (X), (XIX) and (XXI) are known compounds or may be prepared by conventional methods or using techniques analogous to those taught herein.

It will be appreciated that compounds of the formula (I) wherein R$^6$ contains an =O or =S substituent can exist in tautomeric forms. All such tautomeric forms and mixtures thereof are included within this invention. Most aptly the =O or =S substituent in R$^6$ is the =O substituent.

Where they are not commercially available, the intermediates of formula (IV) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in Protectiue Groups in Organic Chemistry, ed. J. F. W. McOmie, Plenum Press, 1973; and T. W. Greene and P. G. M. Wuts, Protective Groups in Organic Synthesis, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with IC$_{50}$ at the NK$_1$ receptor of less than 1 μM on said test method.

For the avoidance of doubt, the nomenclature adhered to throughout this specification follows the general principle illustrated below:

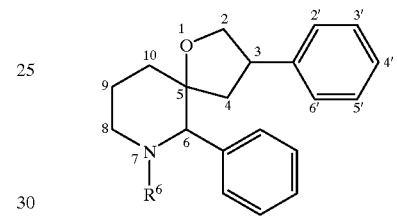

The following non-limiting Examples serve to illustrate the preparation of compounds of the present invention:

DESCRIPTION 1

(±) 1-tert-Butoxycarbonyl-2-phenylpiperidin-3-one

To a cooled (−60° C.) solution of oxalyl chloride (0.68 ml, 7.8 mmol) in dichloronmethane (17 ml) was added dimethyl sulphoxide (0.69 ml, 9.8 mmol) for 10 minutes before addition of (±)1-tert-butoxycarbonyl-3-hydroxy-2-phenylpiperidine (1.8 g, 6.5 mmol; prepared by the method described in European Patent Specification number 0 528 495-A) in dichloromethane (7 ml). The solution was stirred at −60° C. for 20 minutes, warmed to −30° C. and triethylamine (2.5 ml) added. The solution was warmed to room temperature then was washed with ice cold 10% aqueous citric acid solution (40 ml, twice), water and dried (MgSO$_4$). After evaporation the residue was purified by chromatography on silica gel (eluting with hexane containing an increasing proportion of ethyl acetate up to 20%) to give the title compound.

$^1$H NMR (250 MHz, CDCl$_3$) δ 7.5–7.3 (5H,m), 5.8 (1H, br.s), 4.2 (1H, br.s) 3.4 (1H, m), 2.6 (2H, m), 2.0 (2H, m), 1.54 (9H, s).

DESCRIPTION 2

(±)(2S*,3R*) 1-tert-Butoxycarbonyl-3-hydroxy-3-(2-methylene-3-phenoxypropyl)-2-phenylpiperidine A tetrahydrofluran solution of 3-(chloromagnesio)-2-(phenoxymethyl)-1-propene (0.91M, 3 ml) (Louw et. al. Tetrahedron 48:6087–6104, (1992), prepared from 2.74 mmol of 3-chloro-2-(phenoxymethyl)-1-propene) was slowly added to a solution of (±)1-tert-butoxycarbonyl-2-phenylpiperidin-3-one (Desc. 1) in tetrahydrofuran (3 ml).

The solution was stirred at room temperature for 1 hour, quenched by addition of saturated ammonium chloride solution (20 ml) and extracted with ethyl acetate (20 ml). The organic phase was washed (saturated brine), dried (MgSO$_4$), evaporated to a small volume and purified by chromatography on a column containing silica gel (eluting with hexane containing increasing proportions of ethyl acetate between 0% to 20%). Evaporation of the fractions gave the title compound. m/z (CI$^+$)424 (M+H), 324 (M+2H—t-BuOCO—), 368 (M+2H—t-Bu).
$^1$H NMR (360 MHz, CDCl$_3$) δ 7.48 (2H, d, J=6.9 Hz), 7.35–7.2 (6H, m) 6.9–6.88 (3H, m), 5.4 (1H, s), 5.15 (2H, d, J=13.7 Hz), 4.61 (2H, s), 4.11 (2H, m), 3.17 (1H, m), 2.66 and 2.59 (2H, AB d, J=14.0 Hz), 1.95 (2H, m), 1.79 (2H, m), 1.36 (9H, s).

DESCRIPTION 3

(±)(5R*,6S*)-3-Methylene-6-phenyl-1-oxa-7-(tert-butoxycarbonyl)aza-spiro[4.5]decane To a cooled (−80° C.) solution of (±)(2S*,3R*)1-tert-butoxycarbonyl-3-hydroxy-3-(2-methylene-3-phenoxypropyl)-2-phenylpiperidine (1.53 g, 3.62 mmol; Desc. 2) in tetrahydrofuran (20 ml) was added a solution n-butyl lithium in hexanes (2.5M, 1.45 ml, 3.62 mmol) followed by a solution of zinc chloride (0.5M in tetrahydrofuran, 7.24 ml, 3.62 mmol). The solution was allowed to warm to room temperature, tetrakis(triphenylphosphine) palladium (0) (0.23 g, 0.2 mmol) added, degassed and then heated to reflux for 16 hours. After removal of the solvent by evaporation the residue was partitioned between ethyl acetate and 2M sodium hydroxide. The organic phase was washed with saturated brine, dried (MgSO$_4$) and purified by chromatography on a column containing silica gel (eluting with hexane containing increasing proportions of ethyl acetate between 0% to 5%). Evaporation of the fractions gave the title compound. $^1$H NMR (360 MHz, CDCl$_3$) δ 7.58 (2H, d, J=8.4 Hz), 7.32–7.21 (3H, m), 5.23 (1H, s), 5.06 (1H, m), 4.97 (1H, m), 4.39 (2H, AB d, J=13.3 Hz), 3.99(1H, dd, J=13.3, 4.48 Hz), 2.83 (1H, AB d, J=15.5 Hz), 2.7 (1H, td, J=12.5 Hz 3.93 Hz) 2.5 (1H, AB d, J=15.4 Hz), 2.15 (2H, td, J=12.3 Hz 4.4 Hz), 1.69 (2H, m), 1.46 (9H,s). m/z (CI$^+$) 329 (M+2H—t-BuOCO).

DESCRIPTION 4

(±)(5R*,6S*)-3-Keto-6-phenyl-1-oxa-7-(tert-butoxycarbonyl)aza-spiro[4.5]decane

Through a cooled (−80° C.) solution of (±)(6S*,5R*)-3-methylene-6-phenyl-1-oxa-7-(tert-butoxycarbonyl)aza-spiro[4.5]decane (0.665 g; Desc. 3) in dichloromethane (5 ml) and methanol (5 ml) was bubbled a mixture of ozone and oxygen for 45 minutes. After the solution had been purged with nitrogen, dimethyl sulphide (0.5 ml) was added and then stirred under nitrogen at room temperature for 16 hours. The solvent was removed in vacuo and the residue partitioned between ethyl acetate and water. The organic phase was dried (MgSO$_4$), evaporated and the residue purified by chromatography on a column containing silica gel (eluting with hexane containing increasing proportions of ethyl acetate between 0% to 10%). Evaporation of the fractions gave the title compound. m/z (CI$^+$)332 (M+H), 232 (M+2H—t-BuOCO—), 276 (M+2H—t-Bu). $^1$H NMR (250 MHz, CDCl$_3$) δ 7.58 (2H, d, J=6.2 Hz), 7.37–7.26 (3H, m), 5.3 (1H,s), 4.15 and 4.09 (2H, AB d, J=17.4 Hz), 3.97 (1H, m), 2.80 (1H, td, J=12.9 Hz and 4.0 Hz), 2.74 and 2.48 (2H, AB d, J=18.1 Hz), 2.29 (2H, m), 1.88–1.63 (2H, m), 1.44 (9H, s).

DESCRIPTION 5

(±)(5R*,6S*)-3-Trifluoromethylsulphonyl-6-phenyl-1-oxa-7-(tert-butoxycarbonyl)aza-spiro[4.5]dec-3-ene To a cooled (−80° C.) solution of 1M sodium hexamethyldisilazide (0.38 ml, 0.38 mmol) in tetrahydrofuran was added a solution of (±)(5R*,6S*)-3-keto-6-phenyl-1-oxa-7-(tert-butoxycarbonyl)aza-spiro[4.5]decane (0.105 mg, 0.319 mmol; Desc. 4) in tetrahydrofuran (3 ml). The solution was stirred for 1 hour at −80° C. then a solution of 2-[-N,N-bis(trifluoromethylsulphonyl)-amino]-5-chloropyridine (0.163 g, 0.415 mmol) in tetrahydrofuran (3 ml) was added. The solution was stirred at −80° C. for 0.5 hours then at room temperature for 0.5 hours before being quenched by addition of saturated ammonium chloride solution and ethyl acetate. The dried (MgSO$_4$) organic phase was purified by chromatography on a column containing silica gel (eluting with hexane containing increasing proportions of ethyl acetate between 0% to 5%). Evaporation of the fractions gave the title compound. m/z (CI$^+$) 464 (M+H), 364 (M+2H—t-BuOCO—), 408 (M+2H—t-Bu). $^1$H NMR (360 MHz, CDCl$_3$) δ 7.4 (2H, d, J=7.3 Hz), 7.3–7.22 (3H, m), 6.01 (1H, t, J=2.13 Hz), 5.13 (1H, s), 4.56 and 4.26 (2H, AB dd, J=12.4 Hz and 1.97 Hz), 4.10 (1H, dt, J=12.6 Hz and 4.22 Hz), 3.00 (1H, m), 2.28–2.04 (2H, m) 1.88–1.76 (2H, m), 1.37 (9H, s).

DESCRIPTION 6

(±)(5R*,6S*)-3-Trimethylstannyl-6-phenyl-1-oxa-7-(tert-butoxycarbonyl)-aza-spiro[4.5]dec-3-ene To a degassed solution of (±)(5R*,6S*)-3-trifluoromethylsulphonyl-6-phenyl-1-oxa-7-(tert-butoxycarbonyl)aza-spiro[4.5]dec-3-ene (0.482 g, 1.04 mmol; Desc. 5), lithium chloride (0.264 g, 6.25 mmol), lithium carbonate (0.076 g) and hexamethyl distannane (0.96 g, 2.9 mmol) in tetrahydrofuran (10 ml) was added tetrakis(triphenylphosphine) palladium(0) (0.06 g). The solution was degassed and then heated at 60° C. for 5 hours under nitrogen. Water (20 ml) and ethyl acetate (20 ml) were added and the dried organic phase was purified by chromatography on a column containing silica gel (eluting with hexane containing increasing proportions of ethyl acetate between 0% to 5%). Evaporation of the fractions gave the title compound as a crystalline solid. $^1$H NMR (360 MHz, CDCl$_3$) δ 7.25 (2H, d, J=7.3 Hz), 7.1–7.0 (3H,m), 5.83 (1H, t, J=2.5 Hz), 4.78 (1H, s), 4.48 and 4.02 (2H, dd, J=12.9 Hz and 2.3 Hz), 3.96 (1H, dd, J=6.16 Hz and 13.4 Hz), 2.95 (1H, td, J=13.3 Hz and 4.5 Hz), 1.84 (1H, m), 1.68 (1H, m), 1.60 (2H, m), 1.19 (9H, s), 0 (6H, s).

DESCRIPTION 7

2-Bromo-4-(trifluoromethyl-tetrazolyl)-anisole (a) 4-amino-2-bromoanisole

A mixture 2-bromo-4-nitroanisole (15 g, 64.6 mmol) and iron powder (27.3 g, 0.49 mol) in water (100 ml) and glacial acetic acid (25 ml) was stirred at reflux for 2 hours. The mixture was allowed to cool to ambient temperature and filtered through a pad of Hyflo™ (washed with 25% acetic acid/water). The filtrate was extracted with ethyl acetate (2×250 ml) and the organic layer was dried over sodium sulphate. Removal of the solvent in vacuo left an oil which was chromatographed on silica eluting with 40% ethyl acetate/hexane giving the title compound as a brown solid (10.32 g, 79%). Mass Spec ES$^+$ 202 M+1.

(b) 2-Bromo-4-(trifluoroacetamido)anisole

4-Amino-2-bromoanisole (5 g, 24.7 mmol) was dissolved in dichloromethane (50 ml) containing triethylamine (3.44 ml, 24.7 mmol). The solution was cooled to 0° C. and trifluoroacetic anhydride (3.5 ml, 24.7 mmol) was added slowly. The reaction was stirred at ambient temperature for 2 hours, diluted with dichloromethane (200 ml) and washed with water (2×200 ml). The organic layer was dried over sodium sulphate and the solvent was removed in vacuo leaving an oil. Chromatography on silica eluting with 15–25% ethyl acetate/hexane gave the title compound as white solid (4.4 g). $^1$H NMR (250 MHz, CDCl$_3$) δ 7.79 (1H, d, J=2.6 Hz), 7.58 (1H, dd, J=2.6 Hz and 8.9 Hz), 6.90 (1H, d, J=8.9 Hz), 3.90 (3H, s).

(c) 2-Bromo-4-(trifluoromethyl-tetrazolyl)-anisole

2-Bromo-4-(trifluoroacetamido)anisole (4.3 g, 14.4 mmol) was suspended in carbon tetrachloride (80 ml). The suspension was heated to 80° C. and triphenylphosphine (4.54 g, 17.3 mmol) was added in portions over 4 hours. The reaction was stirred at 80° C. for 16 hours. The solvent was removed in vacuo and hexane (100 ml) was added to the residue and heated to reflux temperature. The suspension was allowed to cool to ambient temperature and filtered (triphenylphosphine oxide). The solvent was removed from the filtrate in vacuo leaving an oil (4.6 g). The oil in N,N-dimethylformamide (20 ml) was added to a suspension of sodium azide (1.24 g, 19.1 mmol), in N,N-dimethylformamide (20 ml) at ambient temperature. The mixture was stirred for 2 hours and poured into water (200 ml). The mixture was extracted with ethyl acetate (2×200 ml) and the combined organics were washed with water (200 ml), dried over sodium sulphate and the solvent was removed in uacuo leaving a yellow oil. Chromatography on silica eluting with 25% ethyl acetate/hexane gave the title compound as a clear oil (4.9 g). $^1$H NMR (250 MHz CDCl$_3$) δ 7.72 (1H, d, J=2.6 Hz), 7.44 (1H, dd, J=2.6 Hz and 8.9 Hz), 7.08 (1H, d, J=8.9 Hz), 4.02 (3H, s).

DESCRIPTION 8

(3S)-1-tert-Butoxycarbonyl-2-phenylpiperidin-3-one

To a cooled (−60° C.) solution of oxalyl chloride (0.68 ml, 7.8 mmol) in dicloromethane (17 ml) was added dimethyl sulphoxide (0.69 ml, 9.8 mmol) for 10 minutes before addition of (2S,3S)1-tert-butoxycarbonyl-3-hydroxy-2-phenylpiperidine (1.8 g, 6.5 mmol; prepared by the method described in European Patent Specification number 0 528 495-A) in dicloromethane (7 ml). The solution was stirred at −60° C. for 20 minutes, warmed to −30° C. and triethylamine (2.5 ml) added. The solution was warmed to room temperature then was washed with ice cold 10% aqueous citric acid solution (40 ml, twice), water and dried (MgSO$_4$). This material was used without purification on silica (enantiomeric excess >90%, chiral hplc).

DESCRIPTION 9

2-Bromo-4-nitrophenol

4-Nitrophenol (50 g) was dissolved in glacial acetic acid (400 ml) and bromine (27 ml) was added dropwise and stirred for 18 hours. The reaction mixture was then evaporated to dryness, and the crude product crystallised from dichloromethane:hexane to yield the title compound as white crystals (67 g). $^1$H NMR (250 MHz, CDCl$_3$) δ 8.44 (1H, d, J=2.6 Hz), 8.16 (1H, dd, J=2.6 and 8.9 Hz) and 7.13 (1H, d, J=9.0 Hz).

DESCRIPTION 10

2-iso-Propoxy-5-nitrobromobenzene

2-Bromo-4-nitrophenol (2.5 g; Desc. 9), 2-iodopropane (2.2 g) and potassium carbonate (5 g) were refluxed in acetone (30 ml) for 18 hours. The reaction mixture was then evaporated to dryness, and taken up in ethyl acetate/water. The organic layer was washed (water, brine), dried (MgSO$_4$) and evaporated in vacuo. Chromatography on silica eluting with 10% ethyl acetate/hexane gave the title compound (2.8 g, 94%). $^1$H NMR (250 MHz, CDCl$_3$) δ 8.46 (1H, s), 8.20 (1H, m), 6.93 (1H, m), 4.75 (1H, m), 1.42 (6H, d, J=7.5 Hz).

DESCRIPTION 11

2-iso-Propoxy-5-amino-bromobenzene

Prepared from the compound of Description 10 according to the method of Description 7(a). $^1$H NMR (360 MHz, CDCl$_3$) δ 6.91 (1H, d, J=2.7 Hz), 6.78 (1H, d, J=8.6 Hz), 6.57 (1H, dd, J=2.9 and 8.8 Hz), 4.33 (1H, m), 1.32 (3H, d, J=5.6 Hz).

DESCRIPTION 12

2-iso-Propoxy-5-(trifluoroacetamido)-bromobenzene

Prepared from the compound of Description 11 according to the method of Description 7(b). $^1$H NMR (360 MHz, CDCl$_3$) δ 7.74 (1H, d, J=2.7 Hz), 7.46 (1H, dd, J=2.7 Hz and 8.9 Hz), 6.91 (1H, d, J=8.9 Hz), 4.54 (1H, m), 1.37 (3H, d, J=5.6 Hz).

DESCRIPTION 13

2-iso-Propoxy-5-(trifluoromethyl-tetrazolyl) bromobenzene

Prepared from the compound of Description 12 according to the method of Description 7(c). $^1$H NMR (360 MHz, CDCl$_3$) δ 7.69 (1H, d, J=2.7 Hz), 7.37 (1H, dd, J=2.7 and 8.9 Hz), 7.04 (1H, d, J=8.9 Hz), 4.69 (1H, m), 1.46 (3H, d, J=6.1 Hz).

DESCRIPTION 14

2-Bromo-4-tetrazolyl-anisole

4-Amino-2-bromo-anisole (Desc. 7(a); 4.7 g) was dissolved in triethylorthoformate (50 ml), trifluoroacetic acid (1.8 ml) was added and the mixture heated at reflux for 48 hours. The solvent was removed in vacuo to afford a brown solid. Sodium azide (2.25 g) and acetic acid (25 ml) were added and the mixture heated at reflux for 6 hours. The product was purified on flash silica eluting with dichloromethane containing increasing proportions of methanol (0.25%, 0.5 and 0.75%) to give the title compound as a brown solid (3.98 g, 67% yield). $^1$H NMR (250 MHz, d$_6$-DMSO) δ 4.07 (3H, s), 7.50 (1H, d, J=9 Hz), 8.03 (1H, dd, J=9 Hz, J=3 Hz), 8.32 (1H, d, J=3 Hz), 10.16 (1H, s).

DESCRIPTION 15

2-Bromo-4-(5-(trifluoromethyl)oxazol-4-yl)anisole

Following the procedures described in *J. Org. Chem,* 1988, 53, 129 and *J. Org. Chem.,* 1988, 53, 519, 3-bromo-4-methoxybenzaldehyde was converted through to the appropriately substituted hydrazine by hydrazine formation with t-butyl hydrazine, methylation on nitrogen and reaction with trifluoroacetic anhydride.

Following the procedure in *Heterocycles,* vol 34 No 5, 1992 this hydrazine (1 g) was reacted with 'wet' silica to give the 5-hydroxy-5-trifluoromethyl-3-oxazoline (0.4 g); m/z (ES$^+$) 340/342 (M+1$^+$, 100%). Purified by flash chromatography eluent 5%→10%→15% ethyl acetate in hexane.

Dehydration of the hydroxy oxazoline (0.4 g) to give the title compound (0.123 g) was carried out by refluxing in neat POCl$_3$ for 1 hour. Purification by flash chromatography eluent 2½–5–7½–10% ethyl acetate in hexane.
$^1$H NMR (250 MHz, CDCl$_3$) δ 3.96 (3H, s), 6.97 (1H, d, J=8.6), 7.63 (1H, dd, J=8.5, 2.1), 7.94 (1H, d, J=2.2), 7.97 (1H, s).

DESCRIPTION 16

4-(2,5-Bis(trifluoromethyl)-1,3,4-oxadiazol-1-yl)-2-bromoanisole 2,5-Bistrifluoromethyl-1,3,4-oxadiazole (1.01 g) and 4-amino-2-bromoanisole were heated in a sealed tube at 110° C. for 16 hrs. The two components dissolved to give a brown oil at the reaction temperature. The residue was purified on flash chromatography using eluent 5% ethyl acetate rising to 6%→10% in hexane to afford the title compound as a yellow solid (0.7 g). $^1$H NMR (250 MHz, DMSO) δ 4.07 (3H, s), 7.47 (1H, d, J=9.0), 7.97 (1H, dd, J=8.9, 2.5) 8.28 (1H, d, J=2.5), m/z (ES$^+$) 390/392 (M+1$^+$, 100%).

DESCRIPTION 17

2-Bromo-4-(tetrazol-1-yl)anisole

4-Amino-2-bromoanisole (4.7 g) was suspended in triethylorthoformate (50 ml), trifluoroacetic acid (1.8 ml) was added, and the reaction was heated at reflux for 36 hrs. The triethylorthoformate was removed in vacuo to afford a brown oil, which was dissolved in acetic acid (25 ml), sodium azide (2.25 g) was added and the mixture was heated for 4 hrs. The solvent was removed in vacuo and the residue dispersed between ethyl acetate and saturated sodium hydrogen carbonate. The organic layer was washed with water, brine, dried (MgSO$_4$) and the solvent removed. Purification on flash silica eluting with 100% dichloromethane→0.25%→0.5%→0.75% methanol in dichloromethane afforded the title compound (4 g) as a brown solid. $^1$H NMR (250 MHz, DMSO) δ 4.06 (3H, s), 7.48 (1H, d, J=8.9) 8.03 (1H, dd, J=8.9, 2.7), 8.31 (1H, d, J=2.5), 10.15 (1H, s).

DESCRIPTION 18

5-Amino-7-bromo-2,3-dihydrobenzofuran a) 3-Bromo-4-(prop-2-enyl)oxynitrobenzene 2-Bromo-4-nitrophenol (9.2 g) was dissolved in dimethylformamide (50 ml) and sodium hydride (2.4 g) was added portionwise. The bright yellow solution was stirred until all effervescence ceased. Allyl bromide (4.7 ml) was added and the resulting solution was heated at 60° C. for 30 minutes. The mixture was cooled, quenched by the dropwise addition of water 30 ml, then diluted with water (500 ml) and extracted with ethyl acetate (3×50 ml). The combined organic extracts were washed with sodium hydroxide (2N), water, brine, dried (MgSO$_4$) and evaporated. The residue was purified on silica using 5–10% ethyl acetate in hexane to afford the title compound as a crystalline solid (10 g). $^1$H NMR (360 MHz, CDCl$_3$) δ 4.72 (2H, d, J=6 Hz), 5.37 (1H, d, J=9 Hz), 5.51 (1H, d, J=15 Hz), 6.94 (1H, d, J=6.5 Hz), 8.18 (1H, dd, J=6.5, 2.6 Hz), 8.47 (1H, J=2.6 Hz).

b) 2-Bromo-6-prop-2-enyl-4-nitrophenol

3-Bromo-4-(prop-2-enyl)oxynitrobenzene (8 g) was heated neat at 150–190° C. for 1 hr and at 200–210° C. for 1 hr. The resulting black mixture was purified on silica gel using 10% ethyl acetate in hexane as eluent. This afforded the title compound as a yellow oil which crystallised on standing (5.8 g, 72%). $^1$H NMR (360 MHz, CDCl$_3$) δ 3.50 (2H, d, J=6.5 Hz), 5.14–5.21 (2H, m), 5.91–6.03 (1H, m), 8.03 (1H, d, J=2.6 Hz), 8.30 (1H, d, J=2.6 Hz).

c) 2-Bromo-6-(2-hydroxyethyl)-4-nitrophenol

2-Bromo-6-prop-2-enyl-4-nitrophenol (5.8 g) was dissolved in dichloromethane (30 ml) and methanol (30 ml) and the resulting solution was cooled to −78° C. Ozone was bubbled through the solution until a faint blue coloration was observed and all starting material had reacted. The solution was purged with nitrogen, sodium borohydride (850 g) was added and the solution was allowed to come to room temperature. The solvent was evaporated and the residue was dispersed between ethyl acetate and HCl (1N). The ethyl acetate layer was washed with water, brine, dried (MgSO$_4$) and concentrated. The residue was purified on silica using 2% methanol in dichloromethane as eluent to afford the title compound as a white solid (4 g). $^1$H NMR (360 MHz, CDCl$_3$) δ 3.03 (2H, t, J=5.4 Hz), 4.06 (2H, t, J=5.5 Hz), 8.01 (1H, d, J=2.6 Hz), 8.35 (1H, d, J=2.6 Hz).

d) 7-Bromo-5-nitro-2,3-dihydrobenzofuran

2-Bromo-6-(2-hydroxyethyl)-4-nitrophenol (3.12 g) was dissolved in tetrahydrofuran (20 ml) and was added dropwise to a cooled (0° C.) solution of triphenylphosphine (4.03 g) and diethylazodicarboxylate (2.43 ml) in tetrahydrofuran (30 ml). The mixture was stirred for 3 h and the solvent was removed in vacuo. The residue was purified on silica using 15% ethyl acetate in hexane as eluent to afford the title compound as a white crystalline solid (2 g). $^1$H NMR (250 MHz, CDCl$_3$) δ 3.43 (2H, t, J=8.7 Hz), 4.85 (2H, t, J=9 Hz), 8.03–8.05 (1H, m), 8.20–8.29 (1H, m).

e) 5-Amino-7-bromo-2,3-dihydrobenzofuran

7-Bromo-5-nitro-2,3-dihydrobenzofuran (2 g) was suspended in acetic acid (5 ml) and water (12 ml). Iron powder (3.5 g) was added and the mixture was heated at reflux for 3hr. The cooled mixture was cooled and filtered through celite. The filtrate was concentrated and azeotroped with toluene. The residue was purified by chromatography on silica using 10% ethyl acetate in hexane as eluent to afford the title compound (1.3 g) as an oil. $^1$H NMR (250 MHz, CDCl$_3$) δ 3.22 (2H, t, J=7.5 Hz), 3.38 (2H, br s), 4.58 (2H, t, J=8 Hz), 6.51–6.53 (1H, m), 6.63–6.64 (1H, m).

DESCRIPTION 19

3-Bromo-4-trifluoromethoxy-aniline

4-Trifluoromethoxynitrobenzene (4.1 g) was suspended in water (16 ml) and concentrated sulfric acid (16 ml) and warmed to 80° C. with stirring. Potassium bromate (3.7 g) was added portionwise over 3 hours. The resulting mixture was heated at 80° C. for a further 2 hours, cooled to room temperature and poured onto ice (100 g). The mixture was extracted with ethyl acetate, dried (MgSO$_4$), filtered, and the solvent removed in vacuo. The recovered solid (1.0 g) was taken up in acetic acid (2.5 ml) and water (10 ml) and iron powder (2.0 g) added. The resulting mixture was warmed to reflux for 2 hours, cooled to room temperature and filtered through Celite™. The filtrate was extracted with ethyl acetate, the organic layers separated, dried (MgSO$_4$), filtered and the solvent removed in vacuo. Chromatography on silica gel (ethyl acetate:hexane 1:3) afforded the title compound as a yellow oil. $^1$H NMR (CDCl$_3$) δ 6.57 (1H, dd), 6.9 (1H, d), 7.06 (1H, dd).

DESCRIPTION 20

2-Bromo-4-(3-(trifluoromethyl)tetrazol-1-yl)trifluoroanisole

The title compound was prepared from the product of Description 19 according to the method of step (b) of Description 7. $^1$H NMR (CDCl$_3$) δ 7.54 (2H, m), 7.86 (1H, d, J=1.0 Hz).

DESCRIPTION 21

2-Bromo-4-(3-(trifluoromethyl)tetrazol-1-yl)toluene

The title compound was pepared from 4amino-2-bromotoluene according to the method of step (b) of Description 7. $^1$H NMR (CDCl$_3$) δ 2.53 (3H, s), 7.32 (1H, dd, J=8.0, 1.0 Hz), 7.45 (1H, d, J=8.0 Hz), 7.69 (1H, d, J=1.0 Hz).

DESCRIPTION 22

(2S,3R)-1-tert-Butoxycarbonyl-3-(3-hydroxyropyn-1yl)-2-phenylpiperidin-3-ol

To a cooled (−5° C.) solution of ethylmagnesium bromide (1M in tetrahydrofuran, 130 ml, 130 mmol) in tetrahydrofuran was added O-trimethylsilylpropargyl alcohol slowly. The reaction was stirred at 0° C. for 20 minutes and then at room temperature for 2 hours, before cooling to −10° C. To this was then added a solution of (2S)-1-tert-butoxycarbonyl-2-phenylpiperidin-3-one (Desc. 8; 30 g, 108 mmol) in tetrahydrofuran keeping the temperature below 5° C. The reaction was stirred at room temperature overnight, quenched by addition of water/saturated aqueous ammonium chloride (200 ml/200 ml) and extracted with ethyl acatate (2×200 ml). The combined organic phases were dried (MgSO$_4$) and evaporated to an oil. This oil was dissolved in ethyl acatate (400 ml) and a solution of tetrabutylammonium fluoride (1M in tetrahydrofuran, 130 ml, 130 mmol) added. After stirring at room temperature for 2 hours, water (200 ml) was added, and the two layers separated. The aqueous phase was further extracted with ethyl acatate (200 ml), the organic layers dried (MgSO$_4$) and evaporated to give the product as an oil (50 g) which was used crude for Description 23. $^1$H NMR (CDCl$_3$) δ 7.53–7.55 (2H, m), 7.19–7.35 (3H, m) 5.56 (1H, s), 4.27 (2H, s), 3.99–4.03 (1H, m) 3.25 (1H, bs), 2.77–2.81 (1H, m) 2.77 (1H, bs), 2.12–2.20 (1H, m) 1.91–1.99 (2H, m), 1.77–1.83 (1H, m), 1.39 (9H, s).

DESCRIPTION 23

(5R,6S)-3-Tributylstannyl-6-phenyl-1-oxa-7-(tert-butoxycarbonyl)aza-spiro[4.5]dec-3-ene To a solution of (2S,3R)-1-t-butoxycarbonyl-3-(3-hydroxypropyn-1-yl)-2-phenylpiperidin-3-ol (Desc. 22; 50 g) and tetrakis(triphenylphosphine)palladium (0) (2 g, 1.7 mmol) in toluene (600 ml) was added tributyltin hydride (29 ml, 108 mmol) dropwise. The reaction was stirred at room temperature for 2 hours, after which the solvent was evaporated to give a mixture of the two regioisomeric stannanes, (2S,3R)-1-t-butoxycarbonyl-3-(3-hydroxy-2-tributylstannylpropen-1yl)-2-phenylpiperidin-3-ol and (2S,3R)-1-t-butoxycarbonyl-3-(3-hydroxy-1-tributylstannyl-propen-1yl)-2-phenylpiperidin-3-ol, as an oil. This oil was dissolved in tetrahydrofuran (600 ml), triphenylphosphine (26.2 g, 100 mmol) added, and a solution of diethyl azodicarboxylate (15.7 ml, 100 mmol) in tetrahydrofuran (50 ml) added dropwise. The reaction was stirred at room temperature for 1 hour, the solvent evaporated, the residue dissolved in acetonitrile (500 ml) and extracted with hexane (6×100 ml). The combined hexane layers were evaporated and the residue chromatographed on silica, eluting with 2% ethyl acatate in dichloromethane, to yield first the title compound, (5R,6S)-3-tributylstannyl-6-phenyl-1-oxa-7-(tert-butoxycarbonyl)aza-spiro[4.5]dec-3-ene as an oil (25 g) $^1$H NMR (CDCl$_3$) δ 7.38–7.40 (2H, m) 7.15–7.25 (3H, m), 5.96 (1H, t, J=2.3 Hz), 4.93 (1H, s), 4.63 (1H, dd, J=2.23 and 12.9 Hz), 4.22 (1H, dd, J=2.23 and 12.9 Hz), 4.09–4.14 (1H, m). 3.09–3.17 (1H, m), 1.95–1.99 (1H, m), 1.83–1.86 (1H, m), 1.72–1.76 (2H, m), 1.40–1.51 (6H, m), 1.38 (9H, s), 1.25–1.32 (6H, m), 0.86–0.99 (15H, m), followed by some mixed fractions (6 g) and lastly the other regioisomer (5R,6S)-4-tributylstannyl-6-phenyl -1-oxa-7-(tert-butoxycarbonyl)aza-spiro[4.5]dec-3-ene (3 g).

DESCRIPTION 24

N-(3-Bromo-4-methoxyphenyl)acetamide

Acetic anhydride (3.11 ml, 3.37 g, 33 mmol) was added dropwise to a stirred, cooled (0° C.) solution of 3-bromo-4methoxyaniline (6.06 g, 30 mmol) in dichloromethane (60 ml). The mixture was stirred at room temperature for 90 minutes, methanol (10 ml) was added and the mixture was stirred at room temperature for 30 minutes. The solvent was evaporated under reduced pressure, saturated aqueous sodium hydrogen carbonate (100 ml) and water (50 ml) were added and the mixture was extracted with ethyl acetate (3×100 ml). The combined organic fractions were washed with aqueous hydrochloric acid (1M, 100 ml), saturated aqueous sodium hydrogen carbonate (100 ml) and brine (100 ml), dried (MgSO$_4$) and evaporated under reduced pressure. The residue was recrystallized from ethyl acetate (20 ml)/hexane (50 ml) and the solid was collected and dried in vacuo to give the title compound as a tan solid (6.41 g, 88%), $^1$H NMR (360 MHz, CDCl$_3$) δ 7.68 (1H, d, J=2.5 Hz), 7.45 (1H, dd, J=8.8, 2.5 Hz), 7.36 (1H, br s), 6.84 (1H, d, J=8.8 Hz), 3.87 (3H, s), and 2.16 (3H, s).

DESCRIPTION 25

1-(3-Bromo-4-methoxyphenyl)-2,4-dimethyl-1H-imidazole

Sodium hydride (60% dispersion in mineral oil, 0.90 g, 25.2 mmol) was added to a stirred, cooled (0° C.) solution of N-(3-bromo-4-methoxyphenyl)acetamide (4.58 g. 18.8 mmol) in dimethylformamide (60 ml). The mixture was stirred at 0° C. for 30 minutes, then propargyl bromide (80% solution in toluene, 2.51 ml, 25.2 mmol) was added. The mixture was stirred at room temperature for 30 minutes, then water (150 ml) was added. The mixture was extracted with ethyl acetate (3×150 ml) and the combined organic fractions were washed water (4×150 ml) and brine (150 ml), dried (MgSO$_4$) and evaporated under reduced pressure. The residue was dissolved in acetic acid (15 ml) and mercury (II) acetate (0.90 g, 2.8 mmol) and ammonium acetate (14.47 g, 188 mmol) were added. The mixture was heated under reflux for 4 hours, cooled and poured into water (150 ml). The pH was adjusted to 10.0 with saturated aqueous ammonia and the mixture was extracted with ethyl acetate (3×150 ml). The combined organic fractions were washed with brine (150 ml), dried (MgSO$_4$) and evaporated under reduced pressure. The residue was purified by flash column chromatography on silica gel, eluting with CH$_2$Cl$_2$/MeOH/NH$_3$ (Aq.) (95:5:0.5) and the residue was recrystallized from ethyl acetate (30 ml)/hexane (60 ml). The solid was collected and dried in vacuo to give the title compound as a cream-coloured solid (4.98 g, 94%), $^1$H NMR (360 MHz, CDCl$_3$) δ 7.48 (1H, d, J=2.6 Hz), 7.19 (1H, dd, J=8.7, 2.6 Hz), 6.95 (1H, d, J=8.7 Hz), 6.66 (1H, s), 3.95 (3H, s), 2.30 (3H, s), and 2.22 (3H, s).

DESCRIPTION 26

4-(4-Methoxyphenyl)pyridine

A mixture of 4-methoxybenzene boronic acid (2 g, 13.15 mmol), 4-bromopyridine hydrochloride (3.84 g, 19.72 mmol), diphenylphosphinobutylpalladium (II) dichloride (100 mg), dimethoxyethane (50 ml) and 2M sodium carbonate solution (30 ml) were stirred at 85° C. for 1.5 hours under a nitrogen atmosphere. The solution was allowed to cool to ambient temperature, diluted with ethyl acetate (150 ml) and washed with water (150 ml). The aqueous layer was extracted with ethyl acetate (2×100 ml). The combined organic layers were dried over sodium sulphate and the solvents were removed leaving a white solid, which was chromatographed on silica gel in 70–100% ethyl acetate/hexane giving the title compound as a white solid (1.95 g, 80%). $^1$H NMR (250 MHz, CDCl$_3$) δ 8.66–8.63 (2H, d, J=6.2 Hz), 7.63–7.59 (2H, d, J=9.0 Hz), 7.50–7.47 (2H, d, J=6.2 Hz), 7.03–6.99 (2H, d, J=9.0 Hz), and 3.87 (3H, s). m/z (ES$^+$) 186 (M+1).

DESCRIPTION 27

4-(3-Bromo-4-methoxyphenyl)pyridine 4-(4-Methoxyphenyl)pyridine (1 g, 5.4 mmol) was dissolved in glacial acetic acid (6 ml). Iron powder (30 mg, 0.54 mmol) was added followed by a solution of bromine (0.36 ml) in glacial acetic acid (3 ml) slowly over 5 minutes. The resulting solution was stirred at 60° C. for 1 hour. A solution of bromine (0.13 ml) in glacial acetic acid (1 ml) was added and stirring was continued at 60° C. for 1.5 hours. The solution was allowed to cool to ambient temperature, diluted with water (20 ml). Excess bromine was destroyed by adding in sold sodium bisulphite until all the colour had disappeared. Solid sodium carbonate was added until the solution was basic and the resulting solution was then extracted with ethyl acetate (2×30 ml) and dried over sodium sulphate. Removal of the solvent gave an oil which was chromatographed on silica gel in diethyl ether giving the title compound as a clear oil (0.77 g, 54%). $^1$H NMR (250 MHz, CDCl$_3$) δ 8.66–8.62 (2H, d, J=8.6 Hz), 7.87–7.86 (1H, d, J=2.2 Hz), 7.61–7.56 (1H, dd, J=8.5 Hz and 2.2 Hz), 7.48–7.46 (1H, d, J=8.5 Hz), 7.03–6.99 (2H, d, J=8.6 Hz), and 3.96 (3H, s). m/z (ES$^+$) 264, 266 (M+1).

DESCRIPTION 28

4-(Trifluoromethox)benzene Boronic Acid

1-Bromo-4-(trifluoromethoxy)benzene (5 g, 20.75 mmol) was dissolved in tetrahydrofuran (20 ml). The solution was cooled to −78° C. n-Butyllithium (1.6M in heaxanes, 14.3 ml, 22.8 mmol) was added dropwise keeping the temperature below −60° C. The reaction was stirred at −78° C. for 1 hour. Trimethylborate (14 ml, 0.125M) was added dropwise again keeping the temperature below −60° C. The solution was allowed to warm slowly to ambient temperature and stirred for 16 hours. A 10% citric acid solution (50 ml) was added, the solution was stirred for 1 hour and then extracted with ethyl acetate (2×100 ml). The combined organic layers were dried over sodium sulphate and removal of the solvents gave a white solid which was chromatographed on silica in 35% ethyl acetate/hexane containing 0.5% glacial acetic acid. The title compound was obtained as a white solid (3.34 g, 78%). $^1$H NMR (250 MHz, CDCl$_3$) δ 8.27–8.22 (2H, m), and 7.36–7.23 (2H, m).

DESCRIPTION 29

4-[4-(Trifluoromethoxy)phenyl]pyridine

A mixture of 4-(trifluoromethoxy)benzene boronic acid (2 g, 9.7 mmol), 4-bromopyridine hydrochloride (2.83 g, 14.5 mmol), diphenylphosphinobutylpalladium (II) dichloride (100 mg), dimethoxyethane (50 ml) and a 2M sodium carbonate solution (30 ml) were stirred at 85° C. for 2 hours. The solution was allowed to cool to ambient temperature diluted with water (100 ml), and extracted with ethyl acetate (2×100 ml). The combined organic layers were dried over sodium sulphate. Removal of the solvents in vacuo gave an oil which was chromatographed on silica in 30% ethyl acetate/hexane giving the title compound as an oil (1.86 g, 80%). $^1$H NMR (250 MHz, CDCl$_3$) δ 8.72–8.70 (2H, d, J=6.2 Hz), 7.69–7.63 (2H, d, J=9.6 Hz), 7.49–7.47 (2H, d, J=6.2 Hz), and 7.36–7.32 (2H, d, J=9.6 Hz). m/z (ES$^+$) 240 (M+1).

DESCRIPTION 30

4-[3-Bromo-4-(trifluoromethoxy)phenyl]pyridine

4-[4-(Trifluoromethoxy)phenyl]pyridine (500 mg, 2.1 mmol) was suspended in water (2 ml) and conc. sulphuric acid (2 ml). The suspension was heated to 80° C. and potassium bromate (386 mg, 2.31 mmol) was added in portions over 2 hours. The reaction was stirred at 80° C. for a further 2 hours, allowed to cool to ambient temperature and then poured onto ice. The solution was basified with 4N sodium hydroxide solution, extracted with ethyl acetate (2×30 ml) and the combined organic layers were washed with water. The solution was dried over sodium sulphate and the solvent was removed in vacuo giving an oil (467 mg) which was used without further purification. $^1$H NMR (250 MHz, CDCl$_3$) δ8.70 (2H, br s), 7.92–7.91 (1H, d, J=2.2 Hz), 7.62–7.58 (1H, dd, J=8.5 Hz and 2.2 Hz), and 7.47–7.41 (3H, m), m/z (ES$^+$) 318, 320 (M+1).

DESCRIPTION 31

4-(3-Bromo-4-trifluoromethoxyphenyl)-4H-1,2,4-triazole

The title compound was prepared from 3-bromo-4-(trifluoromethoxy)aniline, using the procedure of Bartlett and Humphrey in *J. Chem. Soc,* (1967) 1664. $^1$H NMR (360 MHz, CDCl$_3$) δ 7.42 (1H, dd, J=8.6 & 2.5 Hz), 7.50 (1H, dd, J=8.6 & 1.3 Hz), 7.73 (1H, d, J=2.5 Hz), and 8.47 (2H, s).

DESCRIPTION 32

N-[3-Bromo-4-(trifluoromethoxy)phenyl] trifluoroacetamide

The title compound was prepared from 3-bromo-4-(trifluoromethoxy)aniline, using the procedure from Description 7b. $^1$H NMR (360 MHz, CDCl$_3$) δ 7.33 (1H, dd, J=10.1 & 1.2 Hz), 7.58 (1H, dd, J=8.9 & 2.6 Hz), 7.97 (1H, d, J=2.6 Hz), and 8.01 (1H, br s).

DESCRIPTION 33

4-[3-Bromo-4-(trifluoromethoxy)phenyl]-3-trifluoromethyl-4H-1,2,4-triazole

N-[3-Bromo-4-(trifluoromethoxy)phenyl] trifluoroacetamide (1.6 g, 4.6 mmol) was suspended in carbon tetrachloride (40 ml). The suspension was heated to 80° C. and triphenylphosphine (1.8 g, 6.9 mmol) was added in portions over 1 hour. The reaction was stirred at 80° C. for 15 hours. The solvent was removed in vacuo and hexane (100 ml) was added to the residue and heated to reflux temperature. The suspension was allowed to cool to ambient temperature and filtered (triphenylphosphine oxide). The solvent was removed from the filtrate in vacuo leaving an oil (1.2 g). The oil was dissolved in dry tetrahydrofuran (5 ml), under a nitrogen atmosphere, cooled to 0° C. and treated with hydrazine hydrate (0.17 ml, 3.3 mmol). The reaction was stirred at room temperature for 10 minutes before the mixture was evaporated in vacuo. The residue was dissolved in acetic acid (20 ml), treated with triethylorthoformate (5 ml, 30 mmol) and heated at reflux for 12 hours. The black mixture was evaporated in vacuo, basified (NaOH, 1M) and extracted with ethyl acetate (2×40 ml). The extracts were washed with brine (20 ml), dried ($Na_2SO_4$) and evaporated in vacuo to a beige solid which was purified by chromatography on silica eluting with ethyl acetate/hexane (1:1) to give the title compound as a white solid (350 mg, 84%). $^1$H NMR (360 MHz, $CDCl_3$) δ 7.41 (1H, dd, J=8.8 & 2.6 Hz), 7.51 (1H, dd, J=8.8 & 1.4 Hz), 7.72 (1H, d, J=2.6 Hz), and 8.36 (1H, s).

DESCRIPTION 34

1-[3-Bromo-4-(methoxy)phenyl]-2-trifluoromethyl-1H-imidazole

2-Bromo-4-(trifluoroacetamido)anisole (Desc. 7b; 4.3 g, 14.4 mmol) was suspended in carbon tetrachloride (80 ml). The suspension was heated to 80° C. and triphenylphosphine (4.54 g, 17.3 mmol) was added in portions over 4 hours. The reaction mixture was stirred at 80° for 16 hours. The solvent was removed in vacuo and hexane (100 ml) was added to the residue and the mixture heated to reflux temperature. The suspension was allowed to cool to ambient temperature and filtered (triphenylphosphine oxide). The solvent was removed from the filtrate in vacuo leaving an oil (4.6 g). A portion of this oil (3.63 g) was dissolved in tetrahydrofuran (40 ml) and treated with aminoacetaldehyde diethyl acetal (5.0 ml, 34 mmol). The mixture was stirred at room temperature for 3 hours, concentrated in vacuo, redissolved in acetic acid (100 ml) and heated at reflux for 1 hour. The mixture was evaporated, treated with 1M sodium hydroxide solution (250 ml) and extracted with ethyl acetate (2×100 ml). The extracts were washed with brine (100 ml), combined, dried ($MgSO_4$) and evaporated to an amber oil. Purification by flash chromatography, eluting with ethyl acetate/hexane (1:2 then 2:3), gave the title compound as a tan solid (2.60 g, 71%); $^1$H NMR (250 MHz, $CDCl_3$) δ 3.97 (3H, s), 6.98 (1H, d, J=8.7 Hz), 7.12 (1H, d, J=1.1 Hz), 7.21 (1H, d, J=1.1 Hz), 7.31 (1H, dd, J=8.7, 2.6 Hz), and 7.58 (1H, d, J=2.6 Hz).

DESCRIPTION 35

1-[3-Bromo-4-(trifluoromethoxy)phenyl]-2-trifluoromethyl-1H-imidazole

The title compound was prepared from N-[3-bromo-4-(trifluoromethoxy)phenyl]trifluoroacetamide, using the procedure from Description 34. $^1$H NMR (360 MHz, $CDCl_3$) δ 7.15 (1H, d, J=1.0 Hz), 7.25 (1H, d, J=1.0 Hz), 7.34–7.46 (2H, m), and 7.70 (1H, d, J=2.4 Hz). m/z ($ES^+$) 375, 377 (M+1).

DESCRIPTION 36

4-(3-Bromo-4-methoxyphenyl)-3-trifluoromethyl-4H-1,2,4-triazole

The title compound was prepared from from N-[3-bromo-4-(trifluoromethoxy)phenyl]trifluoroacetamide, using the procedure described in Description 33. $^1$H NMR (360 MHz, $CDCl_3$) δ 3.99 (3H, s), 7.02 (1H, d, J=8.8 Hz), 7.31 (1H, dd, J=8.8 & 2.6 Hz), 7.57 (1H, d, J=2.6 Hz), and 8.31 (1H, s). m/z (ES) 322, 324 (M+1).

DESCRIPTION 37

3-Bromo-4-(2-hydroxy)ethoxy Nitrobenzene

Sodium hydride (4.13 g, 0.1 mol) was added portionwise to a solution of 2-bromo-4-nitrophenol (Desc. 9, 15 g, 0.07 mol) in N,N-dimethylformamide (85 ml). The resulting mixture was stirred at ambient temperature for 15 minutes. 2-Bromoethanol (6.85 ml, 0.0 mol) was added dropwise, and the resulting solution was heated at 60° C. for 4 hours. The solution was allowed to cool to ambient temperature, diluted with water (150 ml) and extracted with ethyl acetate (3×80 ml). The combined organic fractions were washed with brine (150 ml), dried ($MgSO_4$), and evaporated in vacuo. Purification on silica, eluting with 25%–35% ethyl acetate in hexane afforded the title compound as a yellow solid (7.9 g, 43%). $^1$H NMR (250 MHz, $CDCl_3$) δ 4.05 (2H, t, J=2.9 Hz), 4.27 (2H, t, J=2.8 Hz), 6.96 (1H, d, J=7.9 Hz), 8.18 (1H, dd, J=7.9 Hz, J=2.6 Hz), 8.45 (1H, d, J=2.8 Hz).

DESCRIPTION 38

3-Bromo-4-(2-fluoro)ethoxy Nitrobenzene

To a cooled (−78° C.) suspension of 3-Bromo-4-(2-hydroxy)ethoxy nitrobenzene (7.9 g, 30 mmol) in dichoromethane (80 ml) was added diethylaminosulphur trifluoride (3.88 ml, 31.5 mmol). The solution was stirred at ambient temperature for 2 hours, then quenched by the dropwise addition of water (100 ml). The organic layer was separated, washed with brine (100 ml), dried ($MgSO_4$), and evaporated in vacuo. Purification on silica, eluting with 15%–20% ethyl acetate in hexane afforded the title compound as a yellow oil (1.2 g, 15%). $^1$H NMR (250 MHz, $CDCl_3$) δ 4.35 (1H, dd, J=4.1 Hz, J=2.4 Hz), 4.45 (1H, dd, J=2.4 Hz, J=4.1 Hz), 4.75 (1H, dd, J=4 Hz, J=5.8 Hz), 4.95 (1H, dd, J=4 Hz, J=5.8 Hz), 6.98 (1H, d, J=9.1 Hz), 8.21 (1H, dd, J=2.7 Hz, J=9 Hz).

DESCRIPTION 39

3-Bromo-4-(2-fluoro)ethoxyaniline

Prepared from 3-Bromo-4-(2-fluoro)ethoxy nitrobenzene, using the procedure from Description 7a, but refluxing for only 5 minutes. Purification on silica, eluting with 25% ethyl acetate in hexane afforded the title compound as a brown oil. (1.4 g, 92%). m/z ($CI^+$) 234 (M+1, 100%).

DESCRIPTION 40

3-Bromo-4-[(2-fluoro)ethoxy]trifluoroacetanilide

Prepared from 3-bromo-4-(2-fluoro)ethoxy aniline, using the procedure from Description 7b, to afford the title compound as a white solid (900 mg, 80%). $^1$H NMR (250 MHz, $CDCl_3$) δ 4.23 (1H, t, J=4.23 Hz), 4.33 (1H, t, J=4.2 Hz), 4.70 (1H, t, J=4.1 Hz), 4.89 (1H, t, J=4.1 Hz), 6.93 (1H, d, J=8.9 Hz), 7.52 (1H, dd, J=8.9 Hz, J=2.7 Hz), 7.80 (1H, d, J=2.6 Hz).

DESCRIPTION 41

3-Bromo-4-[(2-fluoro)ethoxy]-[(5-trifluoromethyl)-tetrazol-1-yl]benzene

Prepared from 3-bromo-4-[(2-fluoro)ethoxy]-trifluoroacetanilide, using the procedure from Description 7c, to afford the title compound as a yellow oil (540 mg). $^1$H NMR (250 MHz, CDCl$_3$) δ 4.34 (1H, t, J=4.1 Hz), 4.45 (1H, t, J=4.1 Hz), 4.77 (1H, t, J=3.92 Hz), 4.96 (1H, t, J=4.0 Hz), 7.10 (1H, d, J=8.8 Hz), 7.43 (1H, dd, J=2.6 Hz, J=8.8 Hz), 7.73 (1H, d, J=2.6 Hz).

DESCRIPTION 42

2-Bromo-4-(1-methyltetrazol-5-yl)anisole and 2-Bromo-4(2-methyltetrazol-5-yl)anisole A mixture of 3-bromo-4-methoxybenzonitrile (9 g, 42 mmol), sodium azide (3.03 g, 46.7 mmol) and ammonium chloride (2.5 g, 46.7 mmol) in N,N-dimethylforlmamide (50 ml) was heated at 90° C. for 18 hours. The reaction was cooled, poured onto ice (200 ml) and acidified with 1N HCl to pH1. The resultant solid was filtered, dried and recrystallized from ethanol/water to give 2-bromo-4-(tetrazol-5-yl)anisole (9.2 g). $^1$H NMR 360 MHz, DMSO-d$_6$) δ 3.95 (3H, s), 7.35 (1H, d, J=8.6 Hz), 8.05 (1H, d, =8.6 Hz), 8.23 (1H, s). To a suspension of sodium hydride (60% dispersed, 1.5 g, 37 mmol) in N,N-dimethylformamide was added the foregoing anisole (5 g, 32.5 mmol) and the reaction stirred at room temperature for 2 hours. The reaction was diluted with water (70 ml) and the resultant solid filtered, dried and chromatographed on silica eluting with 60% ethyl acetate/hexane to give 2-bromo-4-(2-methyltetrazol-5-yl)anisole (3.2 g), $^1$H NMR (360 MHz, CDCl$_3$) δ 3.97 (3H, s), 4.39 (3H, s), 7.00 (1H, d, J=12.4 Hz), 8.07 (1H, dd, J=12.4 and 3.0 Hz), 8.34 (1H, d, J=3.0 Hz); and 2-bromo-4-(1-methyltetrazol-5-yl)anisole (0.8 g), 1H NMR (360 MHz, CDCl$_3$) δ 3.94 (3H, s), 4.13 (3H, s), 7.01 (1H, d, J=8.6 Hz), 7.66 (1H, dd, J=8.6 and 2.2 Hz), 7.90 (1H, d, J=2.2 Hz).

DESCRIPTION 43

2-Bromo-4-chloro-1-(tetrazol-1-yl)benzene

3-Bromo-4-chloroaniline (3 g, 14.5 mmol) in acetic acid (40 ml) was treated with triethylorthoformate (6 ml, 36.1 mmol) and heated at 70° C. for 2 hours. Sodium azide (2.84 g, 43.7 mmol) was added portionwise over 10 minutes to the solution at 70° C. and heating continued for a further 2.5 hours. Upon cooling crystals started to appear. Water (25 ml) was added and the mixture aged at 0° C. for 1 hour. The solid was filtered, washed with water (25 ml) and dried in uacuo at 60° C. for 16 hours to give the title compound (3.08 g). $^1$H NMR (250 MHz, CDCl$_3$) δ 7.63–7.89 (2H, m), 8.05 (1H, s), 9.01 (1H, s).

DESCRIPTION 44

1-[3-Bromo-4-(trifluoromethoxy)phenyl]-1H-pyrazole

Sodium nitrite (359 mg, 5.2 mmol) in water (5 ml) was added dropwise to a stirred, cooled (0° C.) suspension of 3-bromo-4-trifluoromethoxyaniline (Description 19) (1.02 g, 4 mmol) in aqueous hydrochloric acid (37%, 10 ml). The mixture was stirred at 0° C. for 30 min., then added dropwise to a stirred, cooled (−5° C.) suspension of tin (II) chloride dihydrate (4.06 g, 18 mmol) in aqueous hydrochloric acid (37%, 10 ml). The mixture was stirred at 0° C. for 30 min., then at room temperature for 30 min. The mixture was poured into cooled (0° C.) aqueous sodium hydroxide (4M, 200 ml) and extracted with ethyl acetate (3×100 ml). The combined organic fractions were washed with aqueous sodium hydroxide (4M, 2×100 ml) and brine (100 ml), dried (MgSO$_4$) and evaporated under reduced pressure. The residue was dissolved in ethanol (10 ml), cooled in ice and ethanolic hydrogen chloride (5M, 0.76 ml, 3.8 mmol) was added. The solvent was evaporated under reduced pressure, ethanol (50 ml) and malonaldehyde bis(dimethyl acetal) (0.63 ml, 0.62 g, 3.8 mmol) were added. The mixture was heated under reflux for 30 min., cooled and the solvent was evaporated under reduced pressure. Saturated aqueous sodium hydrogen carbonate (50 ml) and water (20 ml) were added and the mixture was extracted with ethyl acetate (3×50 ml). The combined organic fractions were washed with brine (50 ml), dried (MgSO$_4$) and evaporated under reduced pressure. The residue was purified by flash column chromatography on silica gel, eluting with hexane/EtOAc (92:8) to give the title compound as a yellow oil (801 mg, 65%). $^1$H NMR (360 MHz, CDCl$_3$) δ 8.04 (1H, d, J=2.6 Hz), 7.90 (1H, d, J=2.4 Hz), 7.74 (1H, d, J=1.8 Hz), 7.68 (1H, dd, J=8.9, 2.6 Hz), 7.39 (1H, d, J=8.9 Hz), and 6.50 (1H, dd, J=2–4, 1.8 Hz). m/z (ES$^+$) 307, 309 (M+1).

DESCRIPTION 45

2-Ethoxy-5-nitrobromobenzene

Iodoethane (3.7 ml) was added to a mixture of 2-bromo-4-nitrophenol (4 g) and potassium carbonate (5.1 g) in N,N dimethylformamide (20 ml) and the mixture was stirred at room temperature for 3 hours. The mixture was partitioned between water (300 ml) and ethyl acetate. After extraction with EtOAc. the combined organic fractions were washed with brine, dried (MgSO$_4$) and the solvent was evaporated under reduced pressure. The residue was purified by flash column chromatography on silica gel, eluting with hexane/EtOAc (95:5 increasing to 90:10) to give the title compound as an oil (3.4 g). $^1$H NMR (250 MHz, CDCl$_3$) δ 1.54 (3H, t, J=9.1 Hz), 4.21 (2H, q, J=7 Hz), 6.93 (1H, d, J=9.1 Hz), 8.19 (1H, dd, J=9.1, 2.7 Hz), and 8.47 (1H, d, J=2.7 Hz).

DESCRIPTION 46

3-Bromo-4-ethoxyaniline

Prepared from the compound of Description 45 according to the method of Description 7a. $^1$H NMR (250 MHz, CDCl$_3$) 1.41 (3H, t, J=7.0 Hz), 4.00 (2H, q, J=7.0 Hz), 6.58 (1H, dd, J=8.6, 2.7 Hz), 6.74 (1H, d, J=8.6 Hz), and 6.91 (1H, d, J=2.7 Hz).

DESCRIPTION 47

N-(3-Bromo-4-ethoxyphenyl)trifluoroacetamide

Prepared from the compound of Description 46 according to the method of Description 7b. 1H NMR (250 MHz, CDCl$_3$) δ 1.47 (3H, t, J=7.0 Hz), 4.10 (2H, q, J=7.0 Hz), 6.88 (1H, d, J=8.9 Hz), 7.48 (1H, dd. J=8.9, 2.6 Hz), and 7.75 (1H, d, J=2.6 Hz).

DESCRIPTION 48

1-(3-Bromo-4-ethoxyphenyl)-2-trifluoromethyl-1H-imidazole

Prepared from the compound of Description 47 according to the method of Description 34. $^1$H NMR (250 MHz, CDCl$_3$) δ 1.52 (3H, t, J=7.0 Hz), 4.16 (2H, q, J=7.0 Hz), 6.94 (1H, d, J=8.8 Hz), 7.11 (1H, d, J=1.2 Hz), 7.21 (1H, d, J=1.2 Hz), 7.27 (1H, dd, J=8.8, 2.43 Hz), and 7.56 (1H, d, J=2.43 Hz).

DESCRIPTION 49

4-(3-Bromo-4-isopropoxyphenyl)-3-trifluoromethyl-4H-1,2,4-triazole

Prepared from the compound of Description 12 according to the method of Description 33. $^1$H NMR (360 MHz, CDCl$_3$) δ 1.44 (6H, d, J=6.1 Hz), 4.66 (1H, sept, J=6.1 Hz), 7.00 (1H, d, J=8.8 Hz), 7.25 (1H, dd, J=8.8, 2.6 Hz), 7.56 (1H, d, J=2.6 Hz), and 8.30 (1H, s). m/z (ES$^+$) 350, 352 (M+1).

DESCRIPTION 50

1-(3-Bromo-4-isopropoxylphenyl)-2-trifluoromethyl-1H-imidazole

Prepared from the compound of Description 12 according to the method of Description 34. $^1$H NMR (360 MHz, CDCl$_3$) δ 1.43 (6H, d, J=6.0 Hz), 4.63 (1H, sept, J=6.1 Hz), 6.96 (1H, d, J=8.8 Hz), 7.10 (1H, d, J=1.1 Hz), 7.20 (1H, d, J=1.0 Hz), 7.25 (1H, dd, J=8.7, 2.6 Hz), and 7.56 (1H, d, J=2.6 Hz). m/z (ES$^+$) 349, 351 (M+1).

DESCRIPTION 51

1-(3-Bromo-4-methoxyphenyl)oxazole

Potassium t-butoxide (2.85 g, 25.4 mmol) was added to a cooled (0° C.) solution of (1H-benzotriazol-1-yl)methyl isocyanide (2 g, 12.7 mmol) and 3-bromo-4-methoxybenzaldehyde (2.72 g, 12.7 mmol) in tetrahydrofuran (10 ml) and ethanol (1.17 g) and the mixture was stirred at 0° C. for 2 hours. The solvent was evaporated under reduced pressure and the residue was partitioned between ethyl acetate and water. The organic phase was dried (MgSO$_4$) and the solvent was evaporated under reduced pressure. The residue was purified by flash column chromatography on silica gel, eluting with hexane/EtOAc (100:0 increasing to 75:25) to give the title compound (2.7 g). $^1$H NMR (250 MHz, CDCl$_3$) δ 1.88 (1H, s), 7.8 (1H, d, J=2.2 Hz), 7.6 (1H, dd, J=8.6, 2.2 Hz), 7.2 (1H, s), 6.8 (1H, d, J=8.6 Hz), and 3.8 (3H, s). m/z (ES$^+$) 254, 256 (M+1).

DESCRIPTION 52

3-Bromo-4-isopropoxybenzaldehyde

Potassium carbonate (10.28 g, 7.4 mmol) and 2-bromopropane (8.7 ml) were added to 3-bromo-4-hydroxybenzaldehyde (7.46 g, 3.7 mmol) in N,N-dimethylformamide (20 ml). The mixture was stirred at room temperature for 3 hours, then partitioned between ethyl acetate and water. The organic phase was washed with brine and dried (MgSO$_4$) and the solvent was evaporated under reduced pressure. The residue was purified by flash column chromatography on silica gel, eluting with hexane/EtOAc (90:10 increasing to 80:20) to give the title compound (5.34 g). $^1$H NMR (250 MHz, CDCl$_3$) δ 9.82 (1H, s), 8.03 (1H, d, J=2.0 Hz), 7.82–7.78 (1H, dd, J=6.0, 2.0 Hz), 7.00 (1H, d, J=6.0 Hz), 4.72 (1H, septet, J=6.0 Hz), and 1.40 (6H, d, J=6.0 Hz).

DESCRIPTION 53

1-(3-Bromo-4-isopropoxyphenyl)oxazole

Prepared from the compound of Description 52 according to the method of Description 51. $^1$H NMR (250 MHz, CDCl$_3$) δ (7.90, 1H, s), 7.82 (1H, d, J=2.2 Hz), 7.52 (1H, dd, J=8.6, 2.2 Hz), 7.22 (1H, s), 6.90 (1H, d, J=8.6 Hz), 4.64 (1H, septet, J=6.0 Hz), and 1.42 (6H, d, J=6.0 Hz).

DESCRIPTION 54

1-Benzyloxy-2-bromo-4-nitrobenzene

2-Bromo-4-nitrophenol (10 g), potassium carbonate (12.7 g) and benzyl bromide were dissolved in dimethylformamide and the mixture was stirred overnight. The mixture was diluted with water (1 L) and extracted with ethyl acetate (3×50 ml). The organic layer was washed with water, brine, dried (MgSO$_4$) and the solvent was evaporated under reduced pressure. The residue was purified by flash column chromatography on silica gel, eluting with hexane/EtOAc (95:5) to give the title compound as a pale yellow solid, (11.8 g, 77%). 1H NMR (250 MHz, CDCl$_3$) δ 8.49 (1H, d, J=2.7 Hz), 8.17 (1H, dd, J=9.1, 2.7 Hz), 7.45 (5H, m), 7.00 (1H, d, J=9.1 Hz), and 5.28 (2H, s).

DESCRIPTION 55

4-Benzyloxy-3-bromoaniline

Prepared from the compound of Description 54 according to the method of Description 7a. $^1$H NMR (250 MHz, CDCl$_3$) δ 7.45 (5H, m), 7.24 (1H, d, J=2.7 Hz), 7.08 (1H, d, J=2.6 Hz), 6.86 (1H, dd, J=8.6, 2.7 Hz), 5.36 (2H, s), and 3.77 (2H, br s). m/z (ES$^+$) 278, 280 (M+1).

DESCRIPTION 56

N-(2-Benzyloxy-3-bromophenyl)trifluoroacetamide

Prepared from the compound of Description 55 according to the method of Description 7b. $^1$H NMR (360 MHz, CDCl$_3$) δ 5.14 (2H, s), 6.91 (1H, d, J=7.2 Hz), 7.24–7.45 (6H, m), 7.77 (1H, d, J=2.6 Hz) and 7.90 (1H, s).

DESCRIPTION 57

1-(2-Benzyloxy-3-bromophenyl)-2-(trifluoromethyl)-1H-imidazole

Prepared from the compound of Description 56 according to the method of Description 34. m/z (ES$^+$) 397, 399 (M+1).

DESCRIPTION 58

3-Bromo-4-(trifluoromethoxy)benzonitrile 4-(Trifluoromethoxy)benzonitrile (5.57 g, 29.8 mmol) was added to 50% aqueous sulfuric acid (60 ml) and the mixture was warmed to 80° C. Potassium bromate (5.97 g, 35.7 mmol) was added in portions over 2 hours and the mixture was stirred at 80° C. for a further 2 hours. The mixture was cooled to room temperature and poured into water (200 ml). The mixture was extracted with ethyl acetate (3×200 ml) and the combined organic layers were dried (MgSO$_4$) and evaporated under reduced pressure to give the title compound as an orange oil (6.0 g) which contained 4-trifluoromethoxy)benzonitrile (ca. 30%) as determined by $^1$H NMR. $^1$H NMR (250 MHz, CDCl$_3$) δ 7.97 (1H, d, J=2.0 Hz), 7.68 (1H, dd, J=8.5, 2.0 Hz), and 7.42 (1H, dq, J=8.5, 1.5 Hz).

DESCRIPTION 59

4-[3-Bromo-4-(trifluoromethoxy)phenyl-1H-1,2,3-triazole

Trimethylsilyl diazomethane (2M solution in hexanes, 17.85 ml, 35.7 mmol) was dissolyed in diethyl ether (150 ml) and cooled to 0° C. n-Butyl lithium (1.6M solution in hexanes, 35.7 mmol) was added dropwise over 10 minutes and the reaction stirred at 0° C. for 20 min. Crude 3-bromo-4-(trifluoromethoxy)benzonitrile (Description 58) (6.0 g) was added over 5 minutes and the mixture was stirred at 0° C. for 1 hour. Saturated aqueous ammonium chloride (200 ml) and water (100 ml) were added and the mixture was extracted with ethyl acetate (3×200 ml). The combined organic layers were dried (MgSO$_4$) and evaporated to give an orange oil (10.1 g). The residue was dissolved in ethanol (150 ml) and potassium fluoride (2.09 g, 36 mmol) and concentrated hydrochloric acid (3.6 ml) were added. The mixture was heated at reflux for 1 hour, cooled to room temperature and the ethanol was evaporated under reduced pressure. Water (200 ml) was added and the mixture was extracted with ethyl acetate (3×200 ml). The combined organic layers were washed with brine (200 ml), dried (MgSO$_4$) and evaporated under reduced pressure. The residue was purified by flash column chromatography on silica gel, eluting with dichloromethane/ether (90:10) to give the title compound as a colorless solid (4.02 g, 44%). $^1$H NMR (250 MHz, CDCl$_3$) δ 8.14 (1H, d, J=2.1 Hz), 8.00 (1H, s), 7.81 (1H, dd, J=8.5, 2.1 Hz), and 7.40 (1H, dq, J=8.5, 1.4 Hz). m/z (ES$^+$) 308, 310 (M+1).

DESCRIPTION 60

2-Methyl-4-[3-bromo-4-(trifluoromethoxy)phenyl]-2H-1,2,3-triazole and 1-methyl-4-[3-bromo-4-(trifluoromethoxy)phenyl]-1H-1,2,3-triazole Tetra n-butyl ammonium fluoride solution (1M in THF, 12.5 ml, 12.5 mmol) was added over 5 minutes to a stirred solution of 4-[3-bromo-4-(trifluoromethoxy)phenyl]-1H-1,2,3-triazole (Description 59) (2.73 g, 8.85 mmol) and dimethyl sulfate (2.10 ml, 22.1 mmol) in THF (50 ml). The mixture was stirred for at room temperature for 1.5 hours, then water (100 ml) and diethyl ether (100 ml) were added. The layers were separated and the aqueous layer was extracted with ether (200 ml). The combined organic layers were washed with water (100 ml) and brine (100 ml), dried (MgSO$_4$) and evaporated under reduced pressure. The residue was purified by flash column chromatography on silica gel, eluting with hexane/EtOAc (75:25 increasing to 50:50) to give 2-methyl-4-[3-bromo-4-(trifluoromethoxy)phenyl]-2H-1,2,3-triazole as a colorless solid (1.50 g, 53%), $^1$H NMR (250 MHz, CDCl$_3$) δ 8.07 (1H, d, J=2.1 Hz), 7.81 (1H, s), 7.73 (1H, dd, J=8.5, 2.1 Hz), 7.36 (1H, dq, J=8.5, 1.4 Hz), and 4.25 (3H, s), m/z (ES$^+$) 322, 324 (M+1), and 1-methyl-4-[3-bromo-4-(trifluoromethoxy)phenyl]-1H-1,2,3-triazole as a colorless solid (566 mg, 20%), $^1$H NMR (250 MHz. CDCl$_3$) d 8.12 (1H, d, J=2.1 Hz), 7.80 (1H, dd, J=8.5, 2.1 Hz), 7.78 (1H, s), 7.36 (1H, dq, J=8.5, 1.5 Hz), and 4.17 (3H, s), m/z (ES$^+$) 322, 324 (M+1).

DESCRIPTION 61

3-(4-Trifluoromethoxyphenyl)pyridine 4-(Trifluoromethoxy) phenyl boronic acid (1.3 g, 6.31 mmol) was dissolved in ethylene glycol dimethyl ether (50 ml). 3-Bromopyridine (1 ml, 9.5 mmol), aqueous sodium carbonate (2M, 30 ml), and Pd(dppb)Cl$_2$ (100 mg) were added and the reaction mixture was stirred at 85° C. for 3 hours. The mixture was allowed to cool to room temperature, then water (200 ml) was added and the mixture was extracted with ethyl acetate (3×100 ml). The combined organic fractions were dried (MgSO$_4$) and the solvent was evaporated under reduced pressure. The residue was purified by flash column chromatography on silica gel, eluting with hexane/ether (60:40) to give the title compound as an oil (1.26 g, 84%). $^1$H NMR (250 MHz, CDCl$_3$) δ 8.84 (1H, s), 8.60 (1H, br d), 7.87 (1H, m), 7.61 (2H, m), and 7.36 (3H, m). m/z (ES$^+$) 240 (M+1).

DESCRIPTION 62

3-(3-Bromo-4-trifluoromethoxyphenyl)pyridine 3-(4-Trifluoromethoxyphenyl)pyridine (Description 61) (1.26 g, 5.27 mmol) was suspended in aqueous sulfic acid (50%, 16 ml) and cooled to 0° C. Potassium bromate (0.88 g, 5.27 mmol) was added in portions over 2 hours and the mixture was stirred at room temperature for 40 min. The mixture was poured into ice/water and basified with aqueous sodium hydroxide (4M). The mixture was extracted with ethyl acetate (3×100 ml) and the combined organic fractions were washed with brine, dried (MgSO$_4$) and the solvent was evaporated under reduced pressure. The residue was purified by flash column chromatography on silica gel, eluting with hexane/ether (60:40) to give the title compound as an oil (1.2 g, 74%). $^1$H NMR (360 MHz, CDCl$_3$) δ 8.82 (1H, s), 8.62 (1H, d), 7.84 (2H, m), 7.54 (1H, dd, J=8.5, 2.2 Hz), 7.41 (2H, m). m/z (ES$^+$) 318, 320 (M+1).

DESCRIPTION 63

3-(Trimethylstannyl)pyridine

3-Bromopyridine (0.8 g, 5.1 mmol), hexamethylditin (5 g, 15.3 mmol), lithium chloride (1.3 g, 30.6 mmol) and lithium carbonate (375 mg, 5.1 mmol) were suspended in tetrahydrofuran (10 ml) under a nitrogen atmosphere. Tetrakis (triphenylphosphine)palladium (0) (290 mg, 0.25 mmol) was added and the solution was stirred at 60° C. for 16 hours, allowed to cool to room temperature, filtered and the solvent was evaporated under reduced pressure. The residue was partitioned between ethyl acetate and water, and the organic layer was dried (Na$_2$SO$_4$) and the solvent was evaporated under reduced pressure. The residue was purified by flash column chromatography on silica gel, eluting with hexane/EtOAc (90:10) to give the title compound as an oil (302 mg). $^1$H NMR (250 MHz, CDCl$_3$) δ 8.66–8.62 (1H, m), 8.58–8.52 (1H, m), 7.93–7.75 (1H, m), 7.27–7.22 (1H, m), and 0.34 (9H, s). MS (ES$^+$) 240–248 (M+1).

DESCRIPTION 64

2-(Benzyloxy)bromobenzene

A mixture of 2-bromophenol (10 g, 57.8 mmol), benzyl bromide (27.5 ml, 0.23 mol) and potassium carbonate (64 g, 0.462 mol) in N,N-dimethylformamide (70 ml) was stirred at room temperature for 72 hours. The suspension was poured into water (500 ml) and extracted with ethyl acetate (2×300 ml). The combined organic fractions were washed with water (300 ml), dried (Na$_2$SO$_4$) and the solvent was evaporated under reduced pressure. The residue was purified by flash column chromatography on silica gel, eluting with hexane/EtOAc (98:2) to give the title compound as a colourless oil (2.9 g). $^1$H NMR (250 MHz, CDCl$_3$) δ 7.58–7.19 (8H, m), 6.95–6.81 (2H, m), and 5.16 (2H, m).

DESCRIPTION 65

(5R,6S)-3-(2-Benzyloxyphenyl)-6-phenyl-1-oxa-7-(tert-butoxycarbonyl)aza-spiro[4.5]dec-3-ene Prepared from the compound of Description 64 and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 7.49–7.34 (7H, m), 7.27–7.17 (4H, m), 7.10–7.06 (1H, m), 6.99–6.90 (2H, m), 6.65–6.64 (1H, t, J=2.05 Hz), 5.11 (2H, dd (AB), J=11.5 Hz), 5.07 (1H, s), 4.98–4.92 (1H, dd, J=12.06, 2.05 Hz), 4.67–4.61 (1H, dd, J=12.06, 2.05 Hz), 4.13–4.06 (1H, m), 3.18–3.10 (1H, m), 2.08–2.03 (1H, m), 1.82–1.71 (3H, m), and 1.32 (9H, s). MS (ES$^+$) 498 (M+1).

DESCRIPTION 66

(5R,6S)-3-(2-Hydroxyphenyl)-6-phenyl-1-oxa-7-(tert-butoxycarbonyl)aza-spiro[4.5]decane (5R,6S)-3-(2-Benzyloxyphenyl)-6-phenyl-1-oxa-7-(tert-butoxycarbonyl)aza-spiro[4.5]dec-3-ene (Description 65)

(450 mg, 0.9 mmol) was dissolved in methanol (15 ml) and 10% palladium on carbon (50 mg) was added. The solution was shaken under hydrogen (50 psi) for 5 hours. The mixure was filtered and the solvent was evaporated under reduced pressure. The residue was purified by flash column chromatography on silica gel, eluting with hexane/EtOAc (85:15) to give the title compound as a foam (253 mg, 68%). $^1$H NMR (360 MHz, CDCl$_3$) δ 7.59–7.57 (2H, m), 7.34–7.29 (2H, m), 7.26–7.22 (1H, m), 7.13–7.05 (2H, m), 6.87–6.83 (1H, m), 6.77–6.74 (1H, m), 5.78 (1H, br s), 5.36 (1H, s), 4.26–4.21 (1H, dd, J=8.9, 7.1 Hz), 4.01–3.95 (1H, m), 3.94–3.89 (1H, dd, J=8.9, 7.2 Hz), 3.70–3.66 (1H, m), 2.87–2.79 (1H, m), 2.50–2.44 (1H, m), 2.25–2.08 (2H, m), 1.81–1.70 (3H, m), and 1.36 (9H, s). MS (ES$^+$) 410 (M+1).

DESCRIPTION 67

(3S,5R,6S)-3-(5-Bromo-2-hydroxyphenyl)-6-phenyl-1-oxa-7-(tert-butoxycarbonyl)aza-spiro[4.5]decane (5R,6S)-3-(2-Hydroxyphenyl)-6-phenyl-1-oxa-7-(tert-butoxycarbonyl)aza-spiro[4.5]decane (Description 66) (100 mg, 0.24 mmol) was dissolved in a 3:2 dichloromethane/methanol mixture (5 ml). Tetrabutylammonium perbromide (118 mg, 0.24 mmol) was added in portions over 10 minutes and the reaction was stirred until the solution became colourless (10 min.). The solvent was evaporated under reduced pressure and the residue was partitioned between ethyl acetate and water. The organic layer was dried (Na$_2$SO$_4$) and the solvent was evaporated under reduced pressure. The residue was purified by flash column chromatography on silica gel, eluting with hexane/EtOAc (80:20) to give the title compound as a foam (76 mg). $^1$H NMR (360 MHz, CDCl$_3$) δ 7.57–7.55 (2H, m), 7.34–7.31 (2H, m), 7.27–7.25 (1H, m), 7.21–7.16 (2H, m), 6.67–6.64 (1H, d, J=8.4 Hz), 6.20 (1H, br s), 5.33 (1H, s), 4.23–4.19 (1H, dd, J=9.06 and 7.07 Hz), 4.02–3.95 (1H, m), 3.94–3.89 (1H, dd, J=9.1 and 6.57 Hz), 3.61–3.57 (1H, m), 2.85–2.81 (1H, m), 2.51–2.45 (1H, m), 2.19–2.13 (2H, m), 1.80–1.73 (3H, m), and 1.36 (9H, s). MS (ES$^+$) 488, 490 (M+1).

DESCRIPTION 68

(3S,5R,6S)-3-(5-Bromo-2-isopropoxyphenyl)-6-phenyl-1-oxa-7-(tert-butoxycarbonyl)aza-spiro[4.5]decane To a solution of (3S,5R,6S)-3-(5-bromo-2-hydroxyphenyl)-6-phenyl-1-oxa-7-(tert-butoxycarbonyl)aza-spiro[4.5]decane (Description 67) (69 mg, 0.14 mmol) and 2-bromopropane (53 ml, 0.56 mmol) in N,N-dimethylformamide (5 ml) was added potassium carbonate (157 mg, 1.12 mmol). The solution was stirred at 50° C. for 72 hours, allowed to cool to ambient temperature, poured into water (50 ml) and extracted with ethyl acetate (2×50 ml). The combined organicfractions were washed with water, dried (Na$_2$SO$_4$) and the solvent was evaporated under reduced pressure. The residue was purified by flash column chromatography on silica gel, eluting with hexane/EtOAc (85:15) to give the title compound as an oil (68.4 mg, 91%). $^1$H NMR (360 MHz, CDCl$_3$) δ 7.5–7.55 (2H, m), 7.34–7.23 (5H, m), 6.72–6.70 (1H, d, J=8.5 Hz), 5.20 (1H, s), 4.53–4.47 (1H, m), 4.24–4.21 (1H, m), 4.01–3.98 (1H, m), 3.75–3.68 (1H, m), 3.65–3.61 (1H, m), 2.92–2.84 (1H, m), 2.41–2.35 (1H, m), 2.18–2.12 (2H, m), 1.77–1.72 (3H, m), 1.40 (9H, s), and 1.34–1.31 (6H, m). MS (ES$^+$) 530, 532 (M+1).

DESCRIPTION 69

3-Bromo-4-methoxyphenylhydrazine

A solution of sodium nitrite (3.16 g, 45.8 mmol) in water (30 ml) was added dropwise over 30 minutes to a stirred, cooled (−5° C.) suspension of 4-amino-2-bromoanisole (Description 7a) (7.31 g, 36.2 mmol) in concentrated hydrochloric acid (50 ml), maintaining the temperature below 0° C. The mixture was stirred at ca. 0° C. for 30 minutes then added portionwise to a suspension of tin (II) chloride dihydrate (36.87 g, 163 mmol) in concentrated hydrochloric acid (50 ml) at −10° C. The resulting thick paste was stirred at −2° C. for 15 min., allowed to warm to room temperature over 20 minutes and stirred at room temperature for a further 20 min. The reaction mixture was recooled, basified with aqueous sodium hydroxide (10M) and extracted with ethyl acetate (2×250 ml). The ex-tracts were washed with brine (250 ml), combined, dried (MgSO$_4$) and the solvent was evaporated under reduced pressure to give 3-bromo-4-methoxphenylhydrazine (7.27 g, 93%). $^1$H NMR (250 MHz, CDCl$_3$) δ 3.84 (3H, s), 6.75 (1H, dd, J=8.8, 2.6 Hz), 6.83 (1H, d, J=8.8 Hz), and 7.11 (1H, d, J=2.6 Hz).

DESCRIPTION 70

1-(3-Bromo-4-methoxyphenyl)-5-trifluoromethyl-1H-1,2,4-triazole and 1-(3-bromo-4-methoxyphenyl)-1H-1,2,4-triazole Trifluoroacetamide (5.87 g, 51.9 mmol) and dimethylformamide dimethyl acetal (3.3 ml, 62 mmol) in dioxane (20 ml) were stirred at 80° C. for 30 min. The the solvent was evaporated under reduced pressure to give a dark yellow oil (7.71 g). A portion of this oil (5.04 g) was added to a solution of 3-bromo-4-methoxyphenylhydrazine (Description 69) (4.29 g, 19.8 mmol) in acetic acid (40 ml) and the mixture stirred at 90° C. overnight. The mixture was cooled and the solvent was evaporated under reduced pressure. The residue was dissolved in ethyl acetate (50 ml) and stirred with saturated aqueous sodium hydrogen carbonate (150 ml) for 15 minutes. The phases were separated and the aqueous phase was extracted with ethyl acetate (2×50 ml). The extracts were washed with brine (50 ml), combined, dried (MgSO$_4$) and the solvent was evaporated under reduced pressure. The residue was purified by flash column chromatography on silica gel, eluting with hexane/EtOAc (80:20 increasing to 25:75) to give 1-(3-bromo-4-methoxyphenyl)-5-trifuoroinethyl-1H-1,2,4-triazole (0.194 g, 3%), $^1$H NMR (360 MHz, CDCl$_3$) δ 3.98 (3H, s), 7.00 (1H, d, J=8.8 Hz), 7.40 (1H, dd, J=8.8, 2.6 Hz), 7.69 (1H, d, J=2.6 Hz), 8.11 (1H, s), and 1-(3-bromo-4-methoxyphenyl)-1H-1,2,4-triazole (0.63 g, 13%), $^1$H NMR 360 MHz, CDCl$_3$) δ 3.96 (3H, s), 6.85 (1H, d, J=8.8 Hz), 7.58 (1H, dd, J=8.8, 2.6 Hz), 7.89 (1H, d, J=2.6 Hz), 8.09 (1H, s), and 8.47 (1H, s).

DESCRIPTION 71

5-(4-Trifluoromethoxy)phenylpyrimidine 4-(Trifluoromethoxy)phenylboronic acid (2 g) and 5-bromopyrimidine 1.7 g) were dissolved in ethylene glycol dimethyl ether (20 ml). Lithium chloride (1.22 g) and sodium carbonate (2 g in 10 ml water) were added and the solution was purged with nitrogen (×3). Tetrakis (triphenylphosphine) palladium (0) (200 mg) was added, the mixture was purged with nitrogen (×3) and stirred at 80° C. for 3 hours. The mixture was cooled, diluted with water (50 ml) and extracted with ethyl acetate (3×50 ml). The combined organic fractions were washed with brine, dried (MgSO$_4$) and the solvent was evaporated under reduced pressure. The residue was purified by flash column chromatography on silica gel, eluting with hexane/EtOAc (50:50) to give the title compound as an amorphous solid (1.3 g) $^1$H NMR (250 MHz, CDCl$_3$) δ 7.39 (2H, dd, J=8.8, 0.9 Hz), 7.62 (2H, dd, J=8.8, 0.9 Hz), 8.95 (2H, s), and 9.30 (1H, s).

DESCRIPTION 72

5-(3-Bromo-4-trifluoromethoxy)phenylpyrimidine

Bromine (0.13 ml) and silver sulphate (0.4 g) and were added to a solution of 5-(4-trifluoromethoxy) phenylpyrimidine (Description 71) (0.62 g, 2.6 mmol) in sulphulic acid (2 ml) and the reaction stirred at room temperature for 45 minutes. The reaction was cooled to 0° C. and ice (10 g) was added. The mixture was neutralized with sodium hydroxide (4M) and filtered, washing with dichloromethane. The filtrate was extracted with dichloromethane (3×50 ml) and the combined organic fractions were washed with aqueous sodium bisulphite (5%, 100 ml) and brine, dried (MgSO$_4$) and the solvent was evaporated under reduced pressure to give the title compound as an oil (0.64 g). $^1$H NMR (360 MHz, CDCl$_3$) δ 7.47 (1H, dd, J=8.5, 1.36 Hz), 7.55 (1H, dd, J=8.5, 2.2 Hz), 7.87 (1H, d, J=2.2 Hz), 8.93 (2H, s), and 9.26 (1H, s). MS (ES$^+$) 319, 321 (M+1).

EXAMPLE 1A (±)(3S*,5R*,6S*)-3-(2-Methoxy-5-(5-(trifluoromethyl)tetrazol-1-yl)phenyl)-6-phenyl-1-oxa-7-(tert-butoxycarbonyl)aza-spiro[4.5]dec-3-ene A mixture of (±)(5R*,6S*)-3-trimethylstannyl-6-phenyl-1-oxa-7-(tert-butoxycarbonyl)aza-spiro[4.5]dec-3-ene (0.2 g, 0.419 mmol; Desc. 6), lithium chloride (0.106 g, 2.51 mmol), 2-bromo-4-(trifluoromethyl-tetrazolyl)-anisole (0.16 g, 0.502 mmol; Desc. 7) in toluene was degassed before addition of tetrakis(triphenylphosphine) palladium(0) (0.06 g) degassed thoroughly the solution was heated to 110° C. for 14 hours. The solution was partitioned between water and ethyl acetate and the dried organic phase was purified by chromatography on a column containing silica gel (eluting with hexane containing increasing proportions of ethyl acetate between 0% to 10%). Evaporation of the fractions gave a residue which was dissolved in hexane/diethyl ether (2:1), filtered and the soluble filtrate was evaporated to give the title compound. m/z (CI$^+$)558 (M+H), 458(M+2H—t-BuOCO—), 502 (M+2H—t-Bu). $^1$H NMR (360 MHz, CDCl$_3$) δ 7.59–7.06 (8H, m), 6.71 (1H, t, J=1.98 Hz), 5.16 (1H, s), 4.91 and 4.56 (2H, AB dd, J=12.0 Hz and 2 Hz), 4.12 (1H, m), 3.97 (3H, s), 3.12 (1H, m), 2.1–2.3 (2H, m), 1.5–1.9 (3H, m), 1.36 (9H, s).

EXAMPLE 1B (±)(3S*,5R*,6S*)-3-(2-Methoxy-5-(5-(trifluoromethyl)tetrazol-1-yl)phenyl)-6-phenyl-1-oxa-7-aza-spiro[4.5]dec-3-ene (±)(3S*,5R*,6S*)-3-(2-Methoxy-(5-(trifluoromethyl) tetrazol-1-yl)phenyl)-6-phenyl-1-oxa-7-(tert-butoxycarbonyl)aza-spiro[4.5]dec-3-ene (135 mg; Ex. 1A) was dissolved in anhydrous trifluoroacetic acid (10 ml) for 10 minutes before evaporation to dryness and purification by chromatography on a column containing silica gel (eluting with dichloromethane containing increasing proportions of methanol/aqueous ammonia (25:1) between 0% to 5%) to give the title compound. m/z (CI$^+$)458 (M+H, 100%). $^1$H NMR (360 MHz, CDCl$_3$) δ 7.33–7.22 (6H, m), 6.99 (1H, d, J=9.0 Hz), 6.88 (1H, d, J=2.67 Hz), 6.12 (1H,t, J=1.97 Hz), 4.91 and 4.53 (2H, AB dd, J=12.4 Hz and 2.0 Hz), 4.3 (1H, s), 3.8 (3H, s), 3.38 (1H, br.d), 3.10 (1H, br.t). 2.3 (1H,m), 1.91 (3H, m).

EXAMPLE 2

(±)(3S*,5R* 6S*)-3-(2-Methoxy-5-(5-(trifluoromethyl)tetrazol-1-yl)phenyl)-6-phenyl-1-oxa-7-aza-spiro[4.5]decane A mixture of (±)(3S*,5R*,6S*)-3-(2-methoxy-5-(5-(trifluoromethyl)-tetrazol-1-yl)phenyl)-6-phenyl-1-oxa-7-aza-spiro[4.5]dec-3-ene (Ex. 1B) and 10% palladium hydroxide/carbon in methanol (20 ml) containing acetic acid (1 ml) was hydrogenated at 50 psi for 4 hours. The solution was filtered, evaporated and purified by chromatography on a column containing silica gel (eluting with dichloromethane containing increasing proportions of methanol/aqueous ammonia (25:1) between 0% to 5%) to give the title compound. m/z (CI$^+$)460 (M+H, 100%). $^1$H NMR (360 MHz, CDCl$_3$) δ 7.41 (2H, br.d), 7.17 (3H, m), 7.06 (1H, t, J=7.5 Hz), 6.88 (1H, d, J=8.82 Hz), 6.17 (1H, d, J=2.62 Hz), 4.19 (1H, t, J=8.22 Hz), 4.02 (1H, s), 3.91 (1H, m), 3.79 (3H, s), 3.31 (1H,t, J=8.77 Hz), 3.08 (1H, br.d, J=12.2 Hz), 2.85 (1H, td, J=10.5 Hz), 2.16 (2H,m), 1.96 (1H, dd, J=12.6 Hz and 8.23 Hz), 1.78 (1H, t, J=11.0 Hz), 1.60 (2H, m).

To a sample dissolved in methanol was added 1M HCl in methanol (1 equivalent). The solution was evaporated and on addition of diethyl ether a colourless crystalline solid was formed, mp 244–246° C.

EXAMPLE 3

(3S,5R,6S)-3-(2-Methoxy-5-(5-(trifluoromethyl) tetrazol-1-yl)nhenyl)-6-phenyl-1-oxa-7-aza-spiro [4.5]decane The title compound was prepared in a manner analogous to Example 2 using (3S,5R,6S)-3-(2-methoxy-5-(5-(trifluoromethyl)tetrazol-1-yl)phenyl)-6-phenyl-1-oxa-7-aza-spiro[4,5]dec-3-ene as the starting material, which compound was prepared in an analogous fashion to Example 1B using (3S)1-tert-butoxycarbonyl-2-phenylpiperidin-3-one (Desc. 8) as the starting material instead of the racemic phenylpiperidinone described in Description 1. m/z (CI$^+$) 460 (M+H, 100%). $^1$H NMR (360 MHz, CDCl$_3$) δ 7.41 (2H, br.d), 7–17 (3H, m), J=7.06 (1H, t, J=7.5 Hz), 6.88 (1H, d, J=8.82 Hz), 6.17 (1H, d, J=2.62 Hz), 4.19 (1H, t, J=8.22 Hz), 4.02 (1H, s), 3.91 (1H, m), 3.79 (3H, s), 3.31 (1H, t, J=8.77 Hz), 3.08 (1H, br.d, J=12.2 Hz), 2.85 (1H, td, J=10.5 Hz), 2.16 (2H,m), 1.96 (1H, dd, J=12.6 Hz and 8.23 Hz), 1.78 (1H, t, J=11.0 Hz), 1.60 (2H, m). (enantiomeric excess 94%, chiral hplc).

EXAMPLE 4A (3S,5R,6S)-3-(2-Isopropoxy-5-(5-trifluoromethyl-tetrazol-1-yl)phenyl)-6-phenyl-1-oxa-7-(tert-butoxycarbonyl)aza-spiro[4.5]dec-3-ene Prepared from the compound of Description 13 and (5R,6S)-3-trimethylstannyl-6-phenyl-1-oxa-7-(tert-butoxycarbonyl)aza-spiro[4.5]dec-3-ene according to the method of Example 1A. Mass Spec ES$^+$ 586 M+1.

EXAMPLE 4B (3S,5R,6S)-3-(2-Isopropoxy-5-(5-trifluoromethyl-tetrazol-1-yl)phenyl)-6-phenyl-1-oxa-7-aza-spiro [4.5]dec-3-ene Prepared from the compound of Example 4A according to the method of Example 1B. $^1$H NMR (250 MHz, CDCl$_3$) δ 7.33–7.37 (2H, m), 7.14–7.24 (3H, m), 6.9 (2H, m), 6.20 (1H, m), 4.89 (1H, dd, J=2.1 and 11.9 Hz), 4.62 (1H, m), 4.36 (1H, dd, J=2.1 and 11.9 Hz), 3.77 (1H, s), 3.30 (1H, m), 2.84 (1H, m), 1.46–2.00 (5H, m), 1.2–1.46 (6H, m).

EXAMPLE 5

(3S,5R,6S)-3-(2-Isopropoxy-5-(5-trifluoromethyl-tetrazol-1-yl)phenyl)-6-phenyl-1-oxa-7-aza-spiro [4.5]decane Hydrochloride Prepared from the compound of Example 4B according to the method of Example 2. $^1$H NMR (250 MHz, CDCl$_3$) δ

7.55 (2H, vb s), 7.15–7.06 (4H, m), 6.86 (1H, d, J=8.9 Hz), 6.07 (1H, d, J=2.5 Hz), 4.57 (1H, m), 4.23 (1H, t, J=8.0 Hz), 3.86–4.00 (2H, m), 3.36 (1H, vb s), 3.14 (1H, t, J=9.0 Hz), 2.83 (1H, vb s), 2.43 (1H, vb s), 2.14 (1H, m), 1.96 (1H, m), 1.56–1.79 (3H, m), 1.32 (6H, m). Mass spec ES+ 488 (M+1).

EXAMPLE 6A (3S,5R,6S)-3-(2-Methoxy-5-(tetrazol-1-yl)phenyl)-6-phenyl-1-oxa-7-(tert-butoxycarbonyl)aza-spiro[4.5]dec-3-ene Prepared from the compound of Description 14 and (5R,6S)-3-trimethylstannyl-6-phenyl-1-oxa-7-(tert-butoxycarbonyl)aza-spiro[4.5]dec-3-ene according to the method of Example 1A, to give the title compound as a white foam (280 mg; 57%) MS (ES+) 490 (M+1, 100%).

EXAMPLE 6B (3S,5R,6S)-3-(2-Methoxy-5-(tetrazol-1-yl)phenyl)-6-phenyl-1-oxa-7-aza-spiro[4.5]dec-3-ene Prepared from the compound of Example 6A according to the method of Example 1B, to give the title compound as a white foam (0.13 g, 75%) MS m/z (ES+) 390 (M+1, 90%). $^1$H NMR (250 MHz, CDCl$_3$) δ 1.81–2.08 (4H, m), 2.78–2.90 (1H, m), 3.45–3.34 (1H, m), 3.79 (1H, s), 3.86 (3H, s), 4.34 (1H, dd, J=2 Hz, J=12 Hz), 4.94 (1H, dd, J=2 Hz, J=12 Hz), 6.20–6.23 (1H, m), 6.93–6.98 (1H, m), 7.04–7.08 (1H, m), 7.13–7i.24 (3H, m), 7.34–7.46 (3H, m), 8.82 (1H, s).

EXAMPLE 7

(3S,5R,6S)-3-(2-Methoxy-5-(tetrazol-1-yl)phenyl)-6-phenyl-1-oxa-7-aza-spiro[4.5]decane Prepared from the compound of Example 6B according to the method of Example 2, to give the title compound as a white foam (64 mg) MS m/z (ES+) 392 (M+1, 100%). $^1$H NMR (250 MHz, CDCl$_3$) δ 1.56–2.22 (6H, m), 2.76–2.90 (1H, m), 3.18–3.30 (2H, m), 3.68 (1H, s), 3.79 (3H, s), 3.82–3.99 (1H, m), 4.07–4.16 (1H, m), 6.42 (1H, d, J=3 Hz), 6.87 (1H, d, J=9 Hz), 7.20–7.32 (3H, m), 7.39–7.45 (1H, dd, J=3 Hz, 9 Hz), 7.46–7.54 (2H, m), 8.61 (1H, s).

In an analogous fashion, the compounds of Table I were prepared from (5R,6S)-3-trimethylstannyl-6-phenyl-1-oxa-7-(tert-butoxycarbonyl)aza-spiro[4.5]dec-3-ene and the appropriate halogenated substituted phenyl compound (cf. formula XIII)):

TABLE 1

| Ex. No. | R$^1$ | R$^2$ | R$^3$ | Data |
|---|---|---|---|---|
| 8 | CH$_3$ | H | (5-CF$_3$-tetrazol-1-yl) | $^1$H NMR (360MHz, D$_2$O) δ 1.19–1.23(3H, m), 1.78–2.00(3H, m), 2.39(3H, s), 3.26(1H, td, J=10, 3.5), 3.46(1H, t, J=11.0), 3.65(1H, m), 3.90(1H, p, J=7.0), 4.27(1H, t, J=11), 4.44(1H, s), 5.90(1H, d J=1.0), 7.0(1H,td, J=6.0, 1.0), 7.25(3H, m), 7.29(1H, d, J=6.0), 7.51(2H, m); m/z (ES+) 444 (100%, M + H); mp 269–271° C. |
| 9 | OCF$_3$ | H | (5-CF$_3$-tetrazol-1-yl) | $^1$H NMR (360MHz, D$_2$O) δ 1.83–1.90(3H, m), 2.10–2.40(3H, m), 2.39(3H, s), 3.20(1H, td, J=10, 2.0), 3.49(2H, m), 4.06(1H, p, J=6.0), 4.26(1H, t, J=6.0), 4.41(1H, s), 6.07(1H, d J=1.0), 7.03(1H, m), 7.26(2H, m), 7.49(4H, m); m/z (ES+) 514 (100%, M + H). mp 255–258° C. |
| 10 | OCH$_3$ | 3'-F | (5-CF$_3$-tetrazol-1-yl) | $^1$H NMR (360MHz, CDCl$_3$) δ 1.54–1.64(2H, m), 1.78(1H, dd, J=10, 10), 1.98(1H, dd, J=8.5, 8.5), 2.09–2.16(2H, m), 2.81(1H, t J=12), 3.24–3.29(3H, m), 3.71(1H, s), 3.90(1H, m), 3.93(3H, d, J=2.5), 4.15(1H, t, J=8), 5.86(1H, t, J=2.5), 6.91(1H, t, J=7.5), 6.98(1H, dd, J=11.0, 2.5), 7.11(2H, t, J=7.5), 7.42(2H, d, J=7.5); m/z (ES+) 478 (100%, M + H). |
| 11 | OCH$_3$ | H | (imidazol-1-yl) | $^1$H NMR (360MHz, D$_2$O) δ 1.74–1.89(3H, m), 2.07–2.18(3H, m), 3.15(1H, m), 3.69(3H, s), 3.86(1H, t, J 3.86 Hz), 4.35 (1H, s), 3.11(1H, d, J=2.6), 6.94(1H, d, J=8.8), 7.16–7.19(2H, m), 7.26–7.30(2H, m), 7.43(2H, d, J=7.4), 8.80(2H, s). m/z (ES+) 391 (100%, M + H). mp 181–183° C. |

TABLE 1-continued

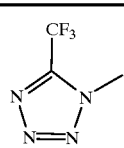

| Ex. No. | R¹ | R² | R³ | Data |
|---|---|---|---|---|
| 12 | OCH₃ | 4'-F | 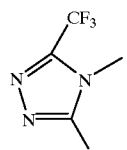 | $^1$H NMR (250Mz, CDCl$_3$) δ 1.52–1.63(2H, m), 1.74–2.15(4H, m), 2.75–2.84(2H, m), 3.16–3.26(2H, m), 3.64(1H, s), 3.81(3H, s), 3.85–3.95(1H, m), 4.12(1H t J=8.2), 5.93(1H, d, J=8.2), 6.66(1H, d, J=11.4), 6.85–6.91(1H, m), 7.11(2H, t, J=7.5), 7.41(2H, t, J=7.2); m/z (ES⁺) 478 (M + H). |
| 13 dec-3-ene | OCH₃ | H | 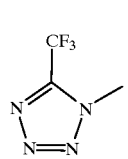 | $^1$H NMR (250MHz, CDCl$_3$) δ 1.69(1H, bd, J=12.7), 1.83(1H, dd, J=13.6, 4.3), 1.96–2.14(2H, m), 2.83(1H, td, J=12.5, 2.8), 3.31(1H, bd, J=10.4), 3.81(1H, s), 3.88(3H, s), 4.24~(1H, dd, J=12.0, 2.2), 4.81(1H, dd J=12.0, 2.2), 6.12(1H, m), 6.69(1H, d, J=2.6), 6.91(1H, d, J=8.9), 7.12–7.20(4H, m), 7.33–7.40(2H, m); m/z (ES+) 525 (100%, M + H). |
| 14 | 2'-O—CH₂—CH₂-3' | | 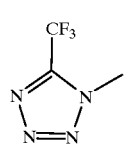 | $^1$H NMR (360MHz, DMSO d$_6$) δ 1.77–1.83(3H, m), 2.98–3.10(1H, m), 3.18(2H, t, J=9.0), 3.25–3.32(3H, m), 3.62(1H, qn, J=10), 4.13(1H, t, J=8.0), 4.44–4.51(3H, m), 6.49(1H, d, J=2.0), 7.22(1H, t, J=7.5), 7.35(2H, t, J=7.5), 7.40(1H, d, J=2.0), 7.52(2H, d, J=7.5); m/z (ES+) 472 (100%, M + H). |
| 15 dec-3-ene | 2'-O—CH₂—CH₂-3' | | 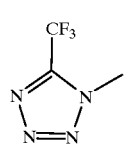 | $^1$H NMR (360MHz, CDCl$_3$) δ 1.94–2.30(4H, m), 3.08–3.28(1H, m), 3.30–3.72(3H, m), 4.48(1H, d J=12.4), 4.74(1H, d, J=10.5), 4.83–4.96(3H, m), 6.54(1H, s), 7.30(1H, d, J=1.9), 7.4–7.5(3H, m), 7.53–7.60(2H, m), 7.63(1H, d, J=1.9).; m/z (ES+) 470 (100%, M + H). |
| 16 | OCH₃ | H | 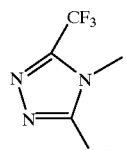 | $^1$H NMR (360MHz, CDCl$_3$) δ 1.56–1.66(1H, m), 1.76(1H, dd, J=12.7, 10.3), 1.94(1H, dd, J=12.7, 9.0), 2.01–2.17(2H, m), 2.80(1H, bt, J=12.2), 3.15(1H, t, J=8.8), 3.24(1H, bd, J=10.2), 3.66(1H, s), 3.81(4H, bs), 3.86–3.98(1H, m), 4.14(1H, dd, J=8.3), 5.78(1H, d, J=2.3), 6.81(1H, d, J=8.8), 6.88(1H, t, J=7.4), 7.02(1H, dd, J=8.8, 2.3), 7.10(2H, t, J=7.6), 7.44(2H, d, J=7.3); m/z (ES+) 527 (100%, M + H). |
| 17 dec-3-ene | OCH₃ | H | 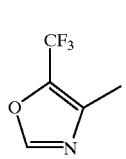 | $^1$H NMR (360MHz, CDCl$_3$) δ 1.80(1H, td, J=13.4, 4.4), 1.92–2.06(3H, m), 2.82(1H, td, J=12.4), 3.27(1H, bd, J=12.2), 3.77(1H, s), 3.82(3H, s), 4.35(1H,dd, J=11.9, 2.0), 4.90(1H, dd, J=11.9, 2.0), 6.87(1H, d, J=8.6), 7.09–7.21(4H, m), 7.36(1H, d, J=7.0), 7.52(1H, dd, J=8.6, 2.1), 7.94(1H, s); m/z (ES+) 457 (100%, M + H). |
| 18 | OCH₃ | H | 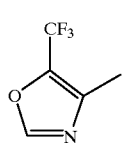 | $^1$H NMR (360MHz, CDCl$_3$) δ 1.78–1.84(1H, dd, J=11.9, 7.2), 1.92–2.19(4H, m), 2.80(1H, td, J=12.1, 2.4), 3.18–3.27(2H, m), 3.67(1H, s), 3.72(3H, s), 3.74–3.83(1H, m), 3.74–3.83(1H, m), 4.14(1H, t, J=7.6), 6.80(1H, d, J=8.6), 6.95(1H, d, J=2.0), 7.14–7.30(3H, m), 7.43–7.50(3H, m), 7.92(1H, s), 7.92(1H,s); m/z (ES+) 459 (100%, M + H). |

EXAMPLE 19

(6S,5R,3S)-7-((2,3-Dihydro-3-oxo-1,2,4-triazol-5-yl)methyl)-3-(2-methoxy-5-(5-(trifluoromethyl) tetrazol-1-yl)phenyl)-6-phenyl-1-oxa-7-aza-spiro [4.5]decane The hydrochloride salt of the product of Example 3 (0.4 g), N-carbomethoxy-2-chloroacetamidrazone (0.149 g) and potassium arbonate (0.552 g) were suspended in dimethylformamide (5 ml) at 40° C. for 4 h and then cooled to room temperature. Water (50 ml) and ethyl acetate (50 ml) were added and the organic phase was washed further with saturated brine and dried (MgSO₄). After evaporation, a solution of the residue in toluene (50 ml) was heated to reflux for 5 h and cooled to room temperature and evaporated to dryness. The residue was purified by chromatography on silica, eluting with dichloromethane followed by 5% methanol in dichloromethane. The fractions containing the desired product were evaporated to dryness and the residue recrystallized from toluene to give the title compound, mp 186–187° C.; $^1$H NMR (360 MHz, DMSO-$_6$) δ 11.14(1H,s), 11.11(1H,s), 7.51(3H, m), 7.11(3H,m), 6.87(1H, t, J=7.4 Hz), 6.2(1H, d, J=2.4 Hz), 4.00(1H, t, J=8.0 Hz),3.80(3H, s), 3.70(1H, m), 3.22(1H, d, J=14.3 Hz), 2.88(2H, m), 2.77(1h, d, J=14.2 Hz), 2.17(1H, td, J=11.1 Hz), 2.04–1.89(3H, m), 1.74(1H, t, J=12.3 Hz), 1.52–1.42(2H, m); m/z (CI+) 557 (100%, M+H).

EXAMPLE 20

(6S,5R,3S)-7-(2-(N,N-Dimethylamino)ethyl)-3-(2-methoxy-5-(5-(trifluoromethyl)tetrazol-1-yl)phenyl)-6-phenyl-1-oxa-7-aza-spiro[4.5]decane The hydrochloride salt of the product of Example 3 (0.263 g) was dissolved in dimethylformamide (6 ml), 2-dimethylaminoethyl chloride (82 mg) and potassium carbonate (0.16 g) were added, and the mixture heated to 60° C. for 3 hrs under an atmosphere of nitrogen. The reaction mixture was dispersed between water (100 ml) and ethyl acetate (50 ml). The organic layer was washed with brine, dried (MgSO$_4$) and the solvent removed in uacuo to afford a clear oil. Purification was carried by flash silica chromatography eluting with a gradient of 2% MeOH in DCM (0.3% NH$_3$)→3%→4% MeOH in DCM (0.3% NH$_3$) to give the title compound. $^1$H NMR (360 MHz, CDCl$_3$) δ 1.44(1H, td, J=13.9, 5.0 Hz), 1.61(1H, bd, J=13.2 Hz), 1.77(1H, dd, J=12.4, 10.6 Hz), 1.89(1H, dd, J=12.8, 8.5 Hz), 2.04(6H, s), 2.02–2.14(3H,m), 2.24(1H, bt, J=11.4 Hz), 2.342.40(2H, m), 2.51–2.61(1H, m), 3.13(–3.26(3H, m), 3.82(3H, s), 3.86(1H, q, J=8.8 Hz), 4.12(1H, t, J=8.2 Hz), 6.05(1H, d, J=2.6 Hz), 6.82–6.92(2H, m), 7.07–7.14(3H, m), 7.44(2H, bd, J=6.6 Hz); m/z (ES+) 531 (100%, M+H).

EXAMPLE 21

(6S,5R,3S)-7-((1H-Imidazol-5-yl)methyl)-3-(2-methoxy-5-(5-(trifluoromethyl)tetrazol-1-yl)phenyl)-6-phenyl-1-oxa-7-aza-spiro[4.5]decane The product of Example 3 (0.3 g) was dissolved in dimethylformamide (6 ml), ((N-p-toluenesulfonyl)-1H-imidazol-5-yl)methyl methanesulfonate (0.188 g) and potassium carbonate (0.17 g) were added and the reaction was heated at 60° C. for 3 hrs under an atmosphere of nitrogen. The reaction was diluted with water (100 ml) and extracted with ethyl acetate (3×50 ml). The combined organics were washed with water, brine, dried (MSO$_4$) and the solvent removed in vacuo to afford a clear oil. Purification was carried out by flash chromatography eluting with a gradient of 5→10→15% ethyl acetate in hexane. The tosylated protected compound (0.293 g) was stirred with methanolic hydrogen chloride (1.0M) (30 ml) at room temperature for 1½ hr. Purification by flash chromatography eluting with 1.5→3% methanol in dichloromethane (0.3% NH$_3$) afforded the title compound as a white foam (0.189 g). $^1$ H NMR (360 MHz, CDCl$_3$) δ 1.45(1H, td, J 3.7, 12.8H), 1.59(1H, bd, J 13.5 Hz), 1.8(1H, dd, J 10.7,12.4 Hz), 1.92(1H, dd, J 12.5. 8.6 Hz), 2.02(1H, bd, J 13.0 Hz), 2.12(1H, bd, J 14.8 Hz), 2.21(1H, bt, J 10.0 Hz), 3.07–3.26(4H,m), 3.60(1H,d, J 14.2 Hz), 3.82(3H, s), 3.88(1H, t, J 9.2 Hz), 4.14(1H, t, J 8.1 Hz), 6.07(1H,d, J 2.6 Hz), 6.77(1H, s), 6.86(1H, d, J 8.8 Hz), 6.95(1H, t, J 7.3 Hz), 7.12–7.22(3H, m), 7.44–7.58(3H, m); m/z (EI+) 540 (100%, M+H).

EXAMPLE 22A

(5R,6S)-3-[2-Methoxy-5-(2,4-dimethyl-1H-imidazol-1-yl)phenyl]-6-phenyl-1-oxa-7-(tert-butoxycarbonyl)aza-spiro[4.5]dec-3-ene Prepared from the compound of Description 25 and (5R,6S)-3-tributylstannyl-6-phenyl-1-oxa-7-(tert-butoxycarbonyl)aza-spiro[4.5]dec-3-ene according to the method of Example 1A. $^1$H (250 MHz, CDCl$_3$) δ 7.46 (2H, m), 7.24 (3H, m), 7.15 (1H, dd, J=8.7 & 2.6 Hz), 6.97 (1H, d, J=8.7 Hz), 6.90 (1H, d, J=2.6 Hz), 6.69 (1H, t, J=2.0 Hz), 6.66 (1H, s), 5.16 (1H, s), 4.94 (1H, dd, J=12.0 & 2.0 Hz), 4.58 (1H, dd, J=12.0 & 2.0 Hz), 3.92 (3H, s), 2.27 (3H, s), 2.23 (3H, s), 2.87–1.41 (6H, m), and 1.37 (9H, s). m/z (ES$^+$) 516 (M+1).

EXAMPLE 22B

(5R,6S)-3- [2-Methoxy-5-(2,4-dimethyl-1H-imidazol-1-yl)phenyl]-6-phenyl-1-oxa-7-aza-spiro [4.5]dec-3-ene Prepared from the compound of Example 22A according to the method of Example 1B. $^1$HNMR (250 MHz, CDCl$_3$) δ 7.38 (2H, m), 4.20 (3H, m), 7.05 (1H, dd, J=8.7 & 2.6 Hz), 6.85 (1H, d, J=8.7 Hz), 6.66 (1H, d, J=2.6 Hz), 6.59 (1H, s), 6.13 (1H, t, J=2.0 Hz), 4.86 (1H, dd, J=12.0 & 2.0 Hz), 4.32 (1H, dd, J=12.0 & 2.0 Hz), 3.82 (3H, s), 3.81 (1H, s), 3.30 (1H, m), 2.82 (1H, m), 2.75 (1H, br s), 2.22 (6H, s), and 2.18–1.62 (4H, m). m/z (ES$^+$) 416 (M+1).

EXAMPLE 23

(3S,5R,6S)-3-[2-Methoxy-5-(2,4-dimethyl-1H-imidazol-1-yl)phenyl]-6-phenyl-1-oxa-7-aza-spiro [4.5]decane Hydrochloride Prepared from the compound of Example 22B according to the method of Example 2. $^1$HNMR (250 MHz, DMSO-d$_6$) δ 9.64 (1H, br s), 8.93 (1H, br s), 7.47 (2H, m), 7.25 (5H, m), 7.00 (1H, d, J=8.9), 6.32 (1H, d, J=2.4), 4.42 (1H, m), 4.07 (1H, m), 3.70 (1H, m), 3.62 (3H, s), 3.46–3.01 (4H, m), 3.00 (1H, m), 2.25 (3H, s), 2.22 (3H, s), and 2.30–1.64 (4H, m. m/z (ES$^+$) 418 (M+1).

EXAMPLE 24A

(5R,6S)-3-[2-Methoxy-5-(4-pyridyl)phenyl]-6-phenyl-1-oxa-7-(tert-butoxycarbonyl)aza-spiro[4.5] dec-3-ene Prepared from the compound of Description 27 and (5R,6S)-3-trimethylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 8.66–8.62 (2H, m), 7.61–7.46 (5H, m), 7.32–7.20 (4H, m), 7.04–6.99 (1H, m), 6.68–6.67 (1H, m), 5.19 (1H, s), 5.06–5.01 (1H, dd, J=12.0 Hz and 2.0 Hz), 4.71–4.65 (1H, dd, J=12.0 Hz and 2.0 Hz), 4.16–4.08 (1H, m), 3.93 (3H, s), 3.18–3.06 (1H, m), 2.16–2.10 (1H m), 1.90–1.78 (3H, m), and 1.38 (9H, s). m/z (ES$^+$) 499 (M+1).

EXAMPLE 24B

(5R,6S)-3-[2-Methoxy-5-(4-pyridyl)phenyl]-6-phenyl-1-oxa-7-aza-spiro[4.5]dec-3-ene Prepared from the compound of Example 24A according to the method of Example 1B. $^1$H NMR (360 MHz, CDCl$_3$)

δ 8.64–8.61 (2H, d, J=6.2 Hz), 7.46–7.39 (3H, m), 7.37–7.35 (2H, d, J=6.2 Hz), 7.22–7.15 (3H, m), 7.13–7.12 (1H, d, J=3.2 Hz), 6.91–6.89 (1H, d, J=8.6 Hz), 6.14–6.13 (1H, m), 4.94–4.90 (1H, dd, J=11.9 Hz and 2.0 Hz), 4.39–4.35 (1H, dd, J=11.9 Hz and 2.0 Hz), 3.82 (3H, s), 3.80 (1H, s), 3.31–3.28 (1H, m), 2.88–2.80 (1H, m), 2.76 (1H, br s), 2.08–1.98 (2H, m), 1.86–1.77 (1H, m), and 1.71–1.63 (1H, m). m/z (ES$^+$) 399 (M+1).

EXAMPLE 25

(3S,5R,6S)-3-[2-Methoxy-5-(4-pyridyl)phenyl]-6-phenyl-1-oxa-7-aza-spiro[4.5]decane Dihydrochloride A mixture of (5R,6S)-3-[2-methoxy-5-(4-pyridyl)phenyl]-6-phenyl-1-oxa-7-aza-spiro[4.5]dec-3-ene (131 mg, 0.33 mmol), ammonium formate (126 mg, 1.97 mmol) and 10% palladium on charcoal (25 mg) in methanol (10 ml) was stirred at 70° C. for 36 hours. The solution was allowed to cool to ambient temperature and filtered. The solvent was removed in vacuo and the residue was chromatographed on alumia (grade III) in 50% ethyl acetate/hexane giving the title compound (33 mg). The dihydrochloride salt was made by treatment with an ethereal hydrogen chloride solution. $^1$H NMR (360 MHz, DMSO-d$_6$) δ 9.71 (1H, m), 9.01 (1H, m), 8.97–8.93 (2H, m), 7.95–7.91 (2H, m), (7.85–7.83 (1H, m), 7.60–7.56 (2H, m), 7.51–7.47 (3H, m), 7.12–7.10 (1H, m), 6.96 (1H, s), 4.53–4.49 (1H, m), 4.14–4.10 (1H, m), 3.87–3.83 (1H, m), 3.72 (3H, S), 3.65–3.20 (5H, m), 3.12–3.08 (1H, m), 2.10–2.05 (2H, m), and 1.92–1.81 (2H, m), m/z (ES$^+$) 401 (M+1).

EXAMPLE 26A (5R,6S)-3-[5-(4-Pyridyl)-2-(trifluoromethoxy)phenyl]-6-phenyl-1-oxa-7-(tert-butoxycarbonyl)aza-spiro [4.5]dec-3-ene Prepared from the compound of Description 30 and (5R,6S)-3-trimethylstannyl-6-pheny-1-oxa-7-(tert-butoxycarbonyl)aza-spiro[4.5]dec-3-ene according to the method of Example 1A. $^1$H NMR (360 MHz, CDCl$_3$) δ 8.66–8.63 (2H, m), 7.56–7.53 (1H, m), 7.47–7.37 (5H, m), 7.29–7.21 (4H, m), 6.57–6.56 (1H, m), 5.17 (1H, s), 4.99–4.96 (1H, m), 4.65–4.62 (1H, m), 4.15–4.09 (1H, m), 3.16–3.12 (1H, m), 2.15–2.11 (1H, m), 1.92–1.86 (3H, m), and 1.36 (9H, s), m/z (ES$^+$) 553 (M+1).

EXAMPLE 26B (5R,6S)-3-[5-(4-Pyridyl)-2-(trifluoromethoxy)phenyl]-6-phenyl-1-oxa-7-aza-spiro[4.5]dec-3-ene Dihydrochloride Prepared from the compound of Example 26A according to the method of Example 1B. $^1$H NMR (360 MHz, DMSO-d$_6$) δ 9.82 (1H, br s), 9.19 (1H, br s), 8.92 (2H, br s), 8.20 (2H, br s), 7.97–7.95 (1H, m) 7.66 (1H, s), 7.55–7.48 (3H, m), 7.36–7.31 (3H, m) 6.47 (1H, s), 5.00–4.97 (1H, m), 4.68–4.65 (1H, m), 4.51–4.47 (1H, m), 3.35–3.31 (2H, m), 3.15–3.11 (1H, m), 2.57–2.53 (2H, m), 2.13–2.09 (1H, m), and 1.98–1.96 (1H, m). m/z (ES$^+$) 453 (M+1).

EXAMPLE 27A (5R,6S)-3-[5-(4H-1,2,4-Triazol-4-yl)-2-(trifluoromethoxy)phenyl]-6-phenyl-1-oxa-7-(tert-butoxycarbonyl)aza-spiro[4.5]dec-3-ene Prepared from the compound of Description 31 and (5R,6S)-3-trimethylstannyl-6-phenyl-1-oxa-7-(tert-butoxycarbonyl)aza-spiro[4.5]dec-3-ene according to the method of Example 1A. m/z (ES$^+$) 543 (M+1).

EXAMPLE 27B (5R,6S)-3-[5-(4H-1,2,4-Triazol-4-yl)-2-(trifluoromethoxy)phenyl]-6-phenyl-1-oxa-7-aza-spiro[4.5]dec-3-ene Prepared from the compound of Example 27A according to the method of Example 1B. $^1$H NMR (360 MHz, CDCl$_3$) δ 1.62–1.72 (1H, m), 1.82–1.87 (1H, m), 1.98–2.11 (2H, m), 2.85 (1H, dt, J=12.5 & 2.9 Hz), 3.29–3.34 (1H, m), 3.84 (1H, s), 4.37 (1H, dd, J=12.2 & 2.1 Hz), 4.86 (1H, dd, J=12.2 & 2.1 Hz), 6.10–6.11 (1H, m), 6.82 (1H, d, J=2.7 Hz), 7.20–7.26 (4H, m), 7.33–7.40 (4H, m), and 8.36 (2H,s). m/z (ES$^+$) 443 (M+1).

EXAMPLE 28

(3S,5R,6S)-3-[5-(4H-1,2,4-Triazol-4-yl)-2-(trifluoromethoxy)phenyl]-6-phenyl-1-oxa-7-aza-spiro[4.5]decane Hydrochloride Prepared from the compound of Example 27B according to the method of Example 2. $^1$H ( (360 MHz, D$_2$O) δ 1.83–1.97 (3H, m), 2.16–2.39 (3H, m), 3.24 (1H, t, J=12.9 Hz), 3.52–3.55 (1H, m), 3.59–3.64 (1H, m), 4.02 (1H, t, J=8.3 Hz), 4.24 (1H, t, 8.5 Hz), 4.44 (1H, s), 6.08 (1H, d, J=2.3 Hz), 7.21 (1H, t, J=7.4 Hz), 7.31–7.42 (4H, m), 7.51 (2H, m), and 8.72 (2H,s). m/z (ES$^+$) 445 (M+1).

EXAMPLE 29A (5R,6S)-3-[2-(Trifluoromethoxy-5-(3-trifluoromethyl-4H-1,2,4-triazol-4-yl)phenyl]-6-phenyl-1-oxa-7-(tert-butoxycarbonyl)aza-spiro[4.5] dec-3-ene Prepared from the compound of Description 33 and (5R,6S)-3-trimethylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 1.34 (9H, s), 1.83–1.90 (3H, m), 2.12–2.14 (1H, m), 3.143.17 (1H, m), 4.11–4.14 (1H, m), 4.55 (1H, dd, J=12.3 & 2.1 Hz), 4.90 (1H, dd, J=12.3 & 1.9 Hz), 5.14 (1H, s), 6.60 (1H, d, J=2.0 Hz), 7.17–7.47 (8H, m), and 8.34 (1H,s). m/z (ES$^+$) 611 (M+1).

EXAMPLE 29B (5R,6)-3-[2-(Trifluoromethoxy-5-(3-trifluoromethyl-4H-1,2,4-triazol-4-yl)phenyl]-6-phenyl-1-oxa-7-aza-spiro[4.5]dec-3-ene Prepared fiom the compound of Example 29A according to the method of Example 1B. $^1$H NMR (360 MHz, CDCl$_3$) δ 1.65–1.68 (1H, m), 1.77–2.03 (4H, m), 2.80–2.90 (1H, m), 3.27 (1H, m), 3.77 (1H, s), 4.32 (1H, dd, J=12.1 & 2.2 Hz), 4.82 (1H, dd, J=12.0 & 2.0 Hz), 6.15–6.16 (1H, m), 6.85 (1H, d, J=2.6 Hz), 7.14–7.36 (7H, m), and 8.27 (1H.s). m/z (ES$^+$) 511 (M+1).

EXAMPLE 30

(3S,5R,6S)-3-[2-(Trifluoromethoxy-5-(3-trifluoromethyl-4H-1,2,4-triazol-4-yl)phenyl]-6-phenyl-1-oxa-7-aza-spiro[4.5]decane Hydrochloride Prepared from the compound of Example 29B according to the method of Example 2. $^1$H NMR (360 MHz, D$_2$O) δ

1.80–1.97 (3H, m), 2.15–2.19 (1H, m), 2.25 (1H, m), 2.38 (1H, dd, J=13.5 & 9.6 Hz), 3.24 (1H, dt, J=13.0 & 3.3 Hz), 3.48–3.55 (2H, m), 4.07–4.14 (1H, m), 4.28 (1H, t, 8.7 Hz), 4.44 (1H, s), 5.74 (1H, d, J=9.4 Hz), 6.99 (1H, t, J=7.5 Hz), 7.30 (2H, t, J=7.8 Hz), 7.39 (1H, dd, J=8.8 & 2.4 Hz), 7.44–7.52 (3H, m), and 8.74 (1H, s). m/z (ES$^+$) 513 (M+1).

EXAMPLE 31A (5R,6S)-3-[2-Methoxy-5-(2-trifluoromethyl-1H-imidazol-1-yl)phenyl]-6-phenyl-1-oxa-7-(tert-butoxycarbonyl)aza-spiro[4.5]dec-3-ene Prepared from the compound of Description 34 and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 7.58–6.96 (10 H, m), 6.31 (1H, t, J=2.0 Hz), 5.16 (1H, s), 4.93 (1H, dd, J=12.0, 2.0 Hz), 4.57 (1H, dd, J=12.0, 2.0 Hz), 3.93 (3H, s), 3.11 (2H, m), 2.11 (1H, m), 1.90–1.70 (3H, m), and 1.36 (9H, s). m/z (ES$^+$) 556 (M+1).

EXAMPLE 31B (5R,6S)-3-[2-Methoxy-5-(2-trifluoromethyl-1H-imidazol-1-yl-)phenyl]-6-phenyl-1-oxa-7-aza-spiro[4.5]dec-3-ene Prepared from the compound of Example 31A according to the method of Example 1B. $^1$H NMR (360 MHz, CDCl$_3$) δ 1.79–1.83 (3H, m), 1.96–2.04 (2H, m), 2.82 (1H, dt, J=12.2 & 2.7 Hz), 3.25–3.29 (1H, m), 3.76 (1H, s), 3.84 (3H, s), 4.28 (1H, dd, J=11.9 & 2.2 Hz), 4.84 (1H, dd, J=11.9 & 2.0 Hz), 6.15 (1H, t, J=2.0 Hz), 6.75 (1H, d, J=2.6 Hz), 6.86 (1H, d, J=8.8 Hz), 7.03 (1H, d, J=1.2 Hz), 7.13–7.19 (5H, m), and 7.35 (2H, d, J=7.6 Hz). m/z (ES$^+$) 456 (M+1).

EXAMPLE 32

(3S,5R,6S)-3-[2-Methoxy-5-(2-trifluoromethyl-1H-imidazol-1-yl)phenyl]-6-phenyl-1-oxa-7-aza-spiro[4.5]decane Hydrochloride Prepared from the compound of Example 31B according to the method of Example 2. $^1$H NMR (360 MHz, D$_2$O) δ 1.82–1.99 (3H, m), 2.19–2.25 (3H, m), 3.25 (1H, dt, J=12.8 & 2 Hz), 3.36 (1H, t, J=8.9 Hz), 3.53–3.56 (1H, m), 3.80 (3H, s), 3.99–4.04 (1H, m), 4.19 (1H, t, J=8.3 Hz), 4.41 (1H, s), 5.85 (1H, d, J=2.4 Hz), 7.00 (1H, d, J=8.8 Hz), 7.10 (1H, t, J=7.5 Hz), 7.20–7.23 (2H, m), 7.30–7.34 (3H, m), and 7.52–7.57 (2H, m). m/z (ES$^+$) 458 (M+1).

EXAMPLE 33A (5R,6S)-3-[2-Trifluoromethoxy-5-(2-trifluoromethyl-1H-imidazol-1-yl)phenyl]-6-phenyl-1-oxa-7-(tert-butoxycarbonyl)aza-spiro[4,5]dec-3-ene Prepared from the compound of Description 35 and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 1.34 (9H, s), 1.80–2.03 (3H, m), 2.09–2.20 (1H, m), 3.10–3.18 (1H, m), 4.09–4.15 (1H, m), 4.57 (1H, dd, J=12.2 & 2.2 Hz), 4.91 (1H, dd, J=12.2 & 2.0 Hz), 5.15 (1H, s), 6.57 (1H, m), 7.14 (1H, d, J=1.2 Hz), and 7.18–7.49 (9H, m). m/z (ES$^+$) 610 (M+1).

EXAMPLE 33B (5R,6S)-3-[2-Trifluoromethoxy-5-(2-trifluoromethyl-1H-imidazol-1-yl)phenyl]-6-phenyl-1-oxa-7-aza-spiro[4.5]dec-3-ene Prepared from the compound of Example 33A according to the method of Example 1B. $^1$H NMR (360 MHz, CDCl$_3$) δ 1.76–2.06 (4H, m), 2.83 (1H, m), 3.25–3.30 (1H, m), 3.79 (1H, s), 4.32 (1H, dd, J=12.1 & 2.2 Hz), 4.82 (1H, dd, J=12.1 & 2.1 Hz), 6.12 (1H, t, J=2.1 Hz), 6.87 (1H, d, J=2.5 Hz), 7.06 (1H,d, J=1.2 Hz), and 7.15–7.36 (8H, m). m/z (ES$^+$) 510 (M+1).

EXAMPLE 34

(3S,5R,6)-3-[2-Trifluoromethoxy-5-(2-trifluoromethyl-1H-imidazol-1-yl)phenyl]-6-phenyl-1-oxa-7-aza-spiro[4.5]decane Hydrochloride Prepared from the compound of Example 33B according to the method of Example 2. $^1$H NMR (360 MHz, D$_2$O) δ 1.81–1.98 (3H, m), 2.16–2.38 (3H, m), 3.25 (1H, dt, J=12.8 & 2 Hz), 3.46 (1H, t, J=8.8 Hz), 3.52–3.55 (1H, m), 4.04–4.09 (1H, m), 4.25 (1H, t, J=8.7 Hz), 4.42 (1H, s), 5.76 (1H, d, J=2.4 Hz), 7.01 (1H, t, J=7.5 Hz), 7.27–7.33 (4H, m), 7.36–7.40 (2H, m), and 7.50 (2H, m). m/z (ES$^+$) 512 (M+1).

EXAMPLE 35A (5R,6S)-3-[2-Methoxy-5-(3-trifluoromethyl-4H-1,2,4triazol-4-yl)phenyl]-6-phenyl-1-oxa-7-(tert-butoxycarbonyl)aza-spiro[4.5]dec-3-ene Prepared from the compound of Description 36 and (5R,6S)-3-tributylstannyl-6-phenyl-1-oxa-7-(tert-butoxycarbonyl)aza-spiro[4–5]dec-3-ene according to the method of Example 1A. $^1$H NMR (250 MHz, CDCl$_3$) δ 1.36 (9H, s), 1.78–1.89 (3H, m), 2.09–2.14 (1H, m), 3.06–3.20 (1H, m), 3.95 (3H, s), 4.10–4.16 (1H, m), 4.56 (1H, dd, J=12.0 & 2.1 Hz), 4.92 (1H, dd, J=12.0 & 2.0 Hz), 5.16 (1H, s), 6.70 (1H, t, J=2.0 Hz), 6.98 (1H, d, J=2.6 Hz), 7.02 (1H, d, J=8.8 Hz), 7.20–7.30 (4H, m), 7.45 (2H, d, J=6.6 Hz), and 8.30 (1H, s). m/z (ES$^+$) 557 (M+1).

EXAMPLE 35B (5R,6S)-3-[2-Methoxy-5-(3-trifluoromethyl-4H-1,2,4-triazol-4-yl)phenyl]-6-phenyl-1-oxa-7-aza-spiro[4.5]dec-3-ene Prepared from the compound of Example 35A according to the method of Example 1B. $^1$H NMR (360 MHz, CDCl$_3$) δ 1.80–1.85 (2H, m), 1.96–2.04 (2H, m), 2.82 (1H, dt, J=12.3 & 2.9 Hz), 3.23–3.30 (1H, m), 3.76 (1H, s), 3.85 (3H, s), 4.27 (1H, dd, J=11.9 & 2.1 Hz), 4.83 (1H, dd, J=11.9 & 2.0 Hz), 6.16 (1H, t, J=2.0 Hz), 6.72 (1H, d, J=2.6 Hz), 6.90 (1H, d, J=8.8 Hz), 7.12–7.19 (4H, m), 7.35 (2H, d, J=7.1 Hz), and 8.22 (1H, s). m/z (ES$^+$) 457 (M+1).

EXAMPLE 36

(3S,5R,6S)-3-[2-Methoxy-5-(3-trifluoromethyl-4H-1,2,4-triazol-4-yl)phenyl]-6-phenyl-1-oxa-7-aza-spiro[4.5]decane Oxalate Prepared from the compound of Example 35B according to the method of Example 2. $^1$H NMR (360 MHz, D$_2$O) δ 1.75–1.81 (3H, m), 2.15–2.21 (3H, m), 3.17 (1H,m), 3.30–3.35 (1H, m), 3.44–3.47 (1H, m), 3.75 (3H, s), 3.97 (1H, t, J=9.0 Hz), 4.14 (1H, t, 8.3 Hz), 4.34 (1H, s), 5.75 (1H, d, J=2.4 Hz), 7.00 (2H, t, J=8.9 Hz), 7.20–7.27 (3H, m), 7.44–7.46 (2H, m), and 8.60 (1H, s). m/z (ES$^+$) 459 (M+1).

EXAMPLE 37A (5R,6S)-3-[2-(2-fluoroethoxy)-5-(5-trifluoromethyl-tetrazol-1-yl)phenyl]-6-phenyl-1-oxa-7-(tert-butoxycarbonyl)aza-spiro[4.5]dec-3-ene Prepared from the compound of Description 41 and (5R,6S)-3-trimethylstannyl-6-phenyl-1-oxa-7-(tert-butoxycarbonyl)aza-spiro[4.5]dec-3-ene according to the method of Example 1A, to afford the title compound as a yellow oil (600 mg, 78%). $^1$H NMR (250 MHz, CDCl$_3$) δ 1.35 (9H, s), 1.85 (3H, m), 2.10 (1H, m), 3.15 (1H, m), 4.10 (1H, m), 4.31 (1H, dt, J=1.8 Hz, J=3 Hz), 4.40 (1H, dt, J=1.9 Hz, J=3 Hz), 4.56 (1H, d, J=2.1 Hz), 4.61 (1H, d, J=2.1 Hz) ,4.73 (1H, m), 4.92 (2H, m), 4.98 (1H, d. J=2.0 Hz), 5.15 (1H, s), 6.76 (1H, t, J=2.0 Hz), 7.05 (1H, d, J=8.9 Hz), 7.18 (1H, d, J=2.6 Hz), 7.21 (3H, m), 7.36 (1H, dd, J=2.6 Hz, J=8.8 Hz), 7.44 (2H, dd, J=1.5 Hz, J=6.5 Hz).

EXAMPLE 37B (5R,6S)-3-[2-(2-fluoroethoxy)-5-(5-trifluoromethyl-tetrazol-1-yl)phenyl]-6-phenyl-1-oxa-7-aza-spiro[4.5]dec-3-ene The compound of Example 37A was stirred in 1N methanolic HCl at ambient temperature for 15 hours. The solvent was evaporated in vacuo and the residue partitioned between aqueous saturated potassium carbonate (50 ml) and ethyl acetate (3×50 ml). The combined organic fractions were washed with brine (50 ml), dried (MgSO$_4$) and evaporated in vacuo. Purification on silica, eluting with 10% methanol in dichloromethane afforded the title compound as a white solid. $^1$H NMR (250 MHz, CDCl$_3$) δ 1.66 (1H, d, J=12.9 Hz), 1.80 (1H, dt, J=4.3 Hz, J=13.3 Hz), 2.0 (1H, d, J=15.4 Hz), 2.07 (1H, m), 2.82 (1H, dt, J=2.8 Hz, J=12.4 Hz), 2.95 (1H, broad s), 3.30 (1H, d, J=12.4 Hz), 3.81 (1H, s), 4.21 (1H, m), 4.29 (1H, m), 4.36 (1H, dd, J=2.1 Hz, J=12 Hz), 4.7 1 (1H, m), 4.85 (1H, m), 4.89 (1H, dd, J=2.1 Hz, J=2.1 Hz), 6.27 (1H, t, J=2.1 Hz), 6.92 (2H, m), 7.18 (3H, m), 7.26 (1H, m), 7.37 (2H, dd J=1.8 Hz, J=8 Hz). m/z (CI$^+$) 490 (M+1, 100%).

EXAMPLE 38

(3S,5R,6S)-3-[2-(2-fluoroethoxy)-5-(5-trifluoromethyl-tetrazol-1-yl)phenyl]-6-phenyl-1-oxa-7-aza-spiro[4.5]decane Hydrochloride Prepared from the compound of Example 37B according to the method of Example 2, to afford the title compound as a white solid (140 mg, 41%). $^1$H NMR (360 MHz, CDCl$_3$) δ 1.56 (1H, m), 1.65 (1H, m), 1.79 (1H, t, J=10.5 Hz), 2.0 (1H, m), 2.17 (2H, m), 2.81 (1H, dt, J=12.3 Hz), 3.24 (1H, t, J=8.9 Hz), 3.28 (1H, m), 3.81 (1H, s), 3.95 (1H, t, J=9.1 Hz), 4.20 (2H, m), 4.26 (1H, d, J=3.8 Hz), 4.69 (1H, t, J=4.1 Hz), 4.82 (1H. t. J=4.0 Hz), 6.10 (1H, d, J=2.5 Hz), 6.87 (1H, d, J=8.8 Hz), 6.98 (1H, t, J=7.5 Hz), 7.13 (3H, m), 7.47 (2H, d, J=7.5 Hz). m/z (CI$^+$) 492 (M+1, 100%).

EXAMPLE 39A (5R,6S)-3-[2-Methoxy-5-(2-methyltetrazol-5-yl)phenyl]-6-phenyl-1-oxa-7-(tert-butoxycarbonyl)aza-sipiro[4.5]dec-3-ene Prepared from compound of Description 42 and (5R,6S)-3-tributylstannyl-6-phenyl-1-oxa -7-(tert-butoxycarbonyl)aza-spiro[4.5]dec-3-ene according to the method of Example 1A. $^1$H NMR (360 MHz, CDCl$_3$) 1.37 (9H, s), 1.83–1.88 (3H, m), 2.02–2.06 (1H, m), 3.12 (1H, m), 3.92 (3H, s), 4.13 (1H, m), 4.37 (3H, s), 4.71 (1H, d, J=12.6 Hz), 5.03 (1H, d, J=12.6 Hz), 5.17 (1H, s), 6.70 (1H, s), 7.01 (1H, d, J=8.7 Hz), 7.19–7.28 (3H, m), 7.48 (2H, d, J=7.6 Hz), 7.83 (1H, s), 8.03 (1H, dd, J=8.7 and 2.1 Hz).

EXAMPLE 39B (5R,6S)-3-[2-Methoxy-5-(2-methyltetrazol-5-yl)phenyl]-6-phenyl-1-oxa-7-aza-spiro[4.5]dec-3-ene Prepared from the compound of Example 39A according to the method of Example 1B. $^1$H NMR (360 MHz, DMSO-d$_6$) δ 1.84–1.88 (2H, m), 2.02–2.06 (2H, m), 3.06–3.10 (2H, m), 3.83 (3H, s), 4.39 (3H, s), 4.44 (1H, d, J=12.6 Hz), 4.58 (1H, bs) 4.96 (1H, d, J=12.6 Hz), 5.75 (1H, s), 7.16 (1H, d, J=8.7 Hz), 7.28–7.34 (3H, m), 7.46–7.50 (3H, m), 7.91 (1H, d, J=6.6 Hz).

EXAMPLE 40A (5R,6S)-3-[2-Methoxy-5-(1-methyltetrazol-5-yl)phenyl]-6-phenyl-1-oxa-7-(tert-butoxycarbonyl)aza-spiro[4.5dec-3-ene Prepared from compound of Description 42 and (5R,6S)-3-tributylstannyl-6-phenyl-1-oxa-7-(tert-butoxycarbonyl)aza-spiro[4.5]dec-3-ene (Desc. 23) according to the method of Example 1A. $^1$H NMR (360 MHz, CDCl$_3$) δ (1.33 (9H, s) 1.75–1.89 (3H, m), 2.04–2.12 (1H, m), 3.09–3.17 (1H, m), 3.95 (3H, s), 4.01 (3H, s), 4.11–4.15 (1H, m), 4.63 (1H, d, J=12.1 Hz). 4.98 (1H, d, J=12.1 Hz), 5.17 (1H, s), 6.69 (1H, s), 7.07 (1H, d, J=8.7 Hz), 7.19–7.28 (2H, m), 7.42–7.47 (3H, m), 7.61 (1H, d, J=8.7 Hz), 7.96 (1H, s).

EXAMPLE 40B (5R,6S)-3-[2-Methoxy-5-(1-methyltetrazol-5-yl)phenyl]-6-phenyl-1-oxa-7-aza-spiro[4.5]dec-3-ene Prepared from compound of Example 40A according to the method of Example 1B. $^1$H NMR (360 MHz, CDCl$_3$) δ 1.86–1.96 (3H, m), 2.02–20.6 (1H, m), 2.94–3.00 (1H, m), 3.54–3.60 (1H, m), 3.98 (3H, s), 4.14 (3H, s), 4.46 (1H, d, J=12.6 Hz), 4.92 (1H, d, J=12.6 Hz), 5.36 (1H, s), 6.06 (1H, s), 6.98 (1H, d, J=7.2 Hz), 7.16–7.36 (5H, m), 7.40–7.50 (2H, m).

EXAMPLE 41

(3S,5R,6S)-3-[2-Methoxy-5-(1-methyltetrazol-5-yl)phenyl]-6-phenyl-1-oxa-7-aza-spiro[4.5]decane Prepared from compound of Example 40B according to the method of Example 2. $^1$H NMR (360 MHz, CDCl$_3$) δ 1.55–1.64 (2H, m), 2.00–2.18 (2H, m), 2.82 (1H, dt, J=12.5 and 2.6 Hz), 3.23–3.30 (2H, m), 3.54 (2H, bs), 3.74 (1H, s), 3.79 (3H, s), 3.87 (3H, s), 3.87–3.98 (1H, m), 6.72 (1H, s), 6.90 (1H, d, J=8.6 Hz), 7.14–7.32 (3H, m), 7.48–7.54 (4H, m).

EXAMPLE 42

(5R, 6S)-3-[2-Chloro-5-(tetrazol-1-yl)phenyl]-6-phenyl-1-oxa-7-(tert-butoxycarbonyl)aza-spiro[4.5]dec-3-ene Prepared from compound of Description 43 and (5R,6S)-3-tributylstannyl-6-phenyl-1-oxa-7-(tert-butoxycarbonyl)aza-spiro[4.5]dec-3-ene (Desc. 23) according to the method of Example 1A. $^1$H NMR (360 MHz, CDCl$_3$) δ 1.36 (9H, s), 1.81–1.93 (3H, m), 2.13–2.19 (1H, m), 3.17–3.20 (1H, m), 4.09–4.16 (1H, m), 4.59 (1H, d, J=12.3 Hz), 4.98 (1H, d, J, 12.3 Hz), 5.18 (1H, s), 6.54 (1H, s), 7.21–7.30 (3H, m), 7.46–7.48 (3H, m), 7.53–7.62 (2H, m), 8.97 (1H, m).

EXAMPLE 43

(5R,6S)-3-[2-Chloro-5-(tetrazol-1-yl)phenyl]-6-phenyl-1-oxa-7-aza-spiro[4.5]decane Prepared from compound of Example 42 according to the method of Example 2. $^1$H NMR (250 MHz, CDCl$_3$) δ

1.67–2.08 (4H, m), 2.86 (1H, dt, J=12.1 and 3.0 Hz), 3.27–3.32 (1H, m), 3.79 (1H, s), 4.33 (1H, d, J=12.2 Hz), 4.89 (1H, d, J=12.2 Hz), 5.98 (1H, s), 6.99 (1H,s), 7.22–7.31 (3H, m), 7.39–7.43 (2H, m), 7.49 (2H, s), 8.87 (1H, s).

EXAMPLE 44A (5R,6S)-3-[5-(1H-Pyrazol-1-yl)-2-(trifluoromethoxy)phenyl]-6-phenyl-1-oxa-7-(tert-butoxycarbonyl)aza-spiro[4.5]dec-3-ene Prepared from the compound of Description 44 and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 7.88 (1H, d, J=2.3 Hz), 7.73 (1H, d, J=1.8 Hz), 7.60–7.21 (8H, m), 6.58 (1H, t, J=2.1 Hz), 6.49 (1H, dd, J=2.3, 1.8 Hz), 5.15 (1H, s), 4.96 (1H, dd, J=12.3, 2.1 Hz), 4.64 (1H, dd, J=12.3, 2.1 Hz), 4.15 (1H, m), 3.16 (1H, m), 2.15–1.80 (4H, m), and 1.36 (9H, s). m/z (ES$^+$) 542 (M+1).

EXAMPLE 44B (5R,6S)-3-[5-(1H-Pyrazol-1-yl)-2-(trifluoromethoxy)phenyl]-6-phenyl-1-oxa-7-aza-spiro[4.51]dec-3-ene Hydrochloride Prepared from the compound of Example 44A according to the method of Example 1B. M.p. 262–265° C. $^1$H NMR (250 MHz, CD$_3$OD) δ 8.21 (1H, d, J=2.0 Hz), 7.71 (2H, m), 7.50 (3H, m), 7.37 (4H, m), 6.54 (1H, t, J=2.0 Hz), 6.31 (1H, t, J=2.0 Hz), 5.00 (1H, dd, J=12.5, 2.0 Hz), 4.65 (1H, dd, J=12.5, 2.0 Hz), 4.56 (1H, s), 3.48 (1H, m), 3.25 (1H, m), and 2.38–1.96 (4H, m). m/z (ES$^+$) 442 (M+1). Found: C, 59.39; H, 4.74; N, 8.64. $C_{24}H_{22}F_3N_3O_2$.HCl.0.5H$_2$O requires: C, 59.20; H. 4.97; N. 8.63%.

EXAMPLE 45A (5R,6S)-3-[2-Ethoxy-5-(2-trifluoromethyl-1H-imidazol-1-yl)phenyl]-6-phenyl-1-oxa-7-(tert-butoxycarbonyl)aza-spiro[4.5]dec-3-ene Prepared from the compound of Description 48 and (5R,6S)-3-tributylstannyl-6-phenyl-1-oxa-7-(tert-butoxycarbonyl)aza-spiro[4.5]dec-3-ene according to the method of Example 1A. m/z (ES$^+$) 570 (M+1).

EXAMPLE 45B (5R,6S)-3-[2-Ethoxy-5-(2-trifluoromethyl-1H-imidazol-1-yl)phenyl]-6-phenyl-1-oxa-7-aza-spiro[4.5]dec-3-ene Prepared from the compound of Example 45A according to the method of Example 1B. $^1$H NMR (360 MHz, CDCl$_3$) δ 1.46 (3H, t, J=10 Hz), 1.61–2.06 (4H, m), 2.82 (1H, td, J=17.2, 3.6 Hz), 3.26 (1H, dt, J=17.5, 2.7 Hz), 3.76 (1H, s), 4.04 (2H, q, J=10 Hz), 4.31 (1H, dd, J=17.2, 3.1 Hz), 4.88 (1H, d, J=17.2, 3.1 Hz), 6.20 (1H, t, J=3 Hz), 6.76–6.86 (2H, m), 7.03 (1H, d, J=1.7 Hz), 7.06–7.24 (4H, m), and 7.29–7.39 (2H, m). m/z (ES$^+$) 470 (M+1).

EXAMPLE 46

(3S,5R,6S)-3-[2-Ethoxy-5-(1H-imidazol-1-yl)phenyl]-6-phenyl-1-oxa-7-aza-spiro[4.5]decane Prepared from the compound of Example 45B according to the method of Example 2. $^1$H NMR (360 MHz, CDCl$_3$) δ 1.41 (3H, t, J=6.8 Hz), 1.54–1.64 (2H, m), 1.79–1.96 (2H, m) 1.97–2.22 (2H, m), 2.81 (1H, td, J=10.0, 2.1 Hz), 3.13 (1H, t, J=8.0 Hz), 3.23 (1H, br d, J=9.8 Hz), 3.65 (1H, s), 3.82–4.04 (3H, m), 4.14 (1H, t, J=8.0 Hz), 6.08 (1H, d, J=8.7 Hz), 6.90 (1H, d, J=1Hz), 6.96 (2H, m), 7.10–7.22 (3H, m), and 7.43 (2H, d, J=7.2 Hz). m/z (ES$^+$) 472 (M+1).

EXAMPLE 47A (5R,6S)-3-[2-Isopropoxy-5-(3-trifluoromethyl-4H-1,2,4-triazol-4-yl)phenyl]-6-phenyl-1-oxa-7-(tert-butoxycarbonyl)aza-spiro[4.5]dec-3-ene Prepared from the compound of Description 49 and (5R,6S)-3-tributylstannyl-6-phenyl-1-oxa-7-(tert-butoxycarbonyl)aza-spirol4.5]dec-3-ene according to the method of Example 1A. $^1$H NMR (360 MHz, CDCl$_3$) δ 1.35 (9H, s), 1.40 (6H, t, J=5.7 Hz), 1.79–1.84 (IH, m), 2.09–2.12 (1H, m), 3.13–3.17 (IH, m), 4.09–4.15 (1H, m), 4.58 (1H, dd, J=12.2, 2.1 H), 4.6–4.69 (1H, m), 4.93 (1H, dd, J=12.2, 2.1 Hz), 5.14 (1H, s), 6.64 (1H, d, J=2.0 Hz), 6.64 (1H, d, J=2.0 Hz), 6.98 (1H, d, J=8.9 Hz), 7.04 (1H, d, J=2.6 Hz), 7.17–7.27 (4H, m), 7.44 (1H, d, J=7.3 Hz), and 8.28 (1H, s). m/z (ES$^+$) 585 (M+1).

EXAMPLE 47B (5R,6S)-3-[2-Isopropoxy-5-(3-trifluoromethyl-4H-1,2,4-triazol-4-yl)phenyl]-6-phenyl-1-oxa-7-aza-spiro[4.5]dec-3-ene Prepared from the compound of Example 47A according to the method of Example 1B. $^1$H NMR (360 MHz, CDCl$_3$) δ 1.34 (6H, dd, J=6.0, 1.6 Hz), 1.70–1.82 (3H, m), 1.96–2.03 (2H, m), 2.82 (1H, dt, J=12.1, 2.8 Hz), 3.76 (1H, s), 4.32 (1H, dd, J=12.0, 2.1 Hz), 4.55–4.61 (1H, m), 4.86 (1H, dd, J=12.0, 2.0 Hz), 6.16 (1H, t, J=2.1 Hz), 6.78 (1H, d, J=2.7 Hz), 6.87 (1H, d, J=8.9 Hz), 7.67–7.20 (4H, m), 7.33–7.35 (2H, m), and 8.22 (1H, s). m/z (ES$^+$) 485 (M+1).

EXAMPLE 48

(3S,5R,6S)-3-[2-Isopropoxy-5-(3-trifluoromethyl-4H-1,2,4-triazol-4-yl)phenyl]-6-phenyl-1-oxa-7-aza-spiro[4.5]decane Hydrochloride Prepared from the compound of Example 47B according to the method of Example 2. $^1$H NMR (360 MHz, D$_2$O) δ 1.27–1.30 (6H, m), 1.75–1.95 (3H, m), 2.13–2.29 (3H, m), 3.18–3.25 (1H, m), 3.35 (1H, t, J=8.7 Hz), 3.49–3.52 (1H, m), 4.02–4.06 (1H, m), 4.23 (1H, t, J=8.5 Hz), 4.39 (1H, s), 4.57–4.63 (1H, m), 5.72 (1H, d, J=2.4 Hz), 7.01 (1H, t, J=7.5 Hz), 7.09 (1H, d, J=8.9 Hz), 7.21–7.30 (3H, m), 7.48–7.50 (2H, d, J=7.4 Hz), and 8.64 (1H, s). m/z (ES$^+$) 487 (M+1).

EXAMPLE 49A (5R,6S)-3-[2-Isopropoxy-5-(2-trifluoromethyl-1H-imidazol-1-yl)phenyl]-6-phenyl-1-oxa-7-(tert-butoxycarbonyl)aza-spiro[4.5]dec-3-ene Prepared from the compound of Description 50 and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) d 1.33 (9H, s), 1.39–1.42 (6H, m), 1.79 (3H, m), 2.09 (1H, m), 3.13 (1H, m), 4.10–4.18 (1H, m), 4.57–4.67 (2H, m), 4.92–4.96 (1H, m), 5.14 (1H, s), 6.63 (1H, m), 6.94 (1H, d, J=8.85 Hz), 7.07 (1H, d, J=2.5 Hz), 7.09 (1H, d, J=0.9 Hz), 7.18–7.25 (5H, m), 7.45 (1H, d, J=7.5 Hz), and 8.28 (1H, s). m/z (ES$^+$) 584 (M+1).

EXAMPLE 49B (5R,6S)-3-[2-Isopropoxy-5-(2-trifluoromethyl-1H-imidazol-1-yl)phenyl]-6-phenyl-1-oxa-7-azaspiro[4.5]dec-3-ene Prepared from the compound of Example 49A according to the method of Example 1B. $^1$H NMR (250 MHz, CDCl$_3$) d 1.33 (6H, dd. J=6.0, 2.1 Hz), 1.63–1.72 (2H, m), 1.95–2.03 (2H, m), 2.82 (1H, dt, J=12.0, 3.0 Hz ), 3.23–3.29 (1H, m), 3.76 (1H, s), 4.32 (1H, dd, J=12.0, 2.2 Hz), 4.51–4.61 (1H, sept, J=6.0 Hz), 4.86 (1H, dd, J=12.0, 2.1 Hz), 6.18 (1H, t, J=2.1 Hz), 6.80–6.85 (2H, m), 7.04 (1H, d, J=1.29 Hz), 7.07–7.21 (4H, m), and 7.33–7.37 (2H, m). m/z (ES$^+$) 484 (M+1).

EXAMPLE 50

(3S,5R,6S)-3-[2-Isopropoxy-5-(2-trifluoromethyl-1H-imidazol-1-yl)phenyl]-6-phenyl-1-oxa-7-aza-spiro[4.5]]decane Hydrochloride Prepared from the compound of Example 49B according to the method of Example 2. $^1$H NMR (360 MHz, D$_2$O) d 1.29–1.32 (6H, m), 1.79–2.00 (3H, m), 2.18–2.28 (3H, m), 3.24–3.37 (2H, m), 3.55–3.58 (1H, m), 4.02–4.10 (1H, m), 4.23 (1H, t, J=8.4 Hz), 4.41 (1H, s), 4.55–4.61 (1H, m), 5.79 (1H, d, J=2.1 Hz), 7.04–7.09 (2H, m), 7.15–7.17 (2H, m), 7.24–7.33 (3H, m), and 7.51 (2H, d, J=7.3 Hz). m/z (ES$^+$) 486 (M+1).

EXAMPLE 51A (5R,6S)-3-[2-Methoxy-5-(oxazol-5-yl)phenyl]-6-phenyl-1-oxa-7-(tert-butoxycarbonyl)aza-spiro[4.5]dec-3-ene Prepared from the compound of Description 51 and (5R,6S)-3-tributylstannyl-6-phenyl-1-oxa-7-(tert-butoxycarbonyl)aza-spiro[4.5]dec-3-ene according to the method of Example 1A.

EXAMPLE 51B (5R,6S)-3-[2-Methoxy-5-(oxazol-5-yl)phenyl]-6-phenyl-1-oxa-7-aza-spiro[4.5]dec-3-ene Prepared from the compound of Example 51A according to the method of Example 1B. $^1$H NMR (360 MHz, CDCl$_3$) δ 1.66 (1H, d, J=11.2 Hz), 1.8 (1H, d, J=4.4 Hz), 1.92–2.08 (2H, m), 3.28 (1H, d, J=10.5 Hz), 3.8 (4H, s), 4.32 (1H, dd, J=12.0, 2.1 Hz), 4.88 (1H, dd, J=12.0, 2.2 Hz), 6.10–6.18 (1H, m), 6.82 (1H, d, J=9.0 Hz), 7.2 (1H, d, J=2.0 Hz), 7.10–7.24 (4H, m), 7.38–7.42 (3H, m), and 7.82 (1H, s). m/z (ES$^+$) 389 (M+1).

EXAMPLE 52

(3S,5R,6S)-3-[2-Methoxy-5-(oxazol-5-yl)phenyl]-6-phenyl-1-oxa-7-aza-spiro[4.5]decane Prepared from the compound of Example 51B according to the method of Example 2. $^1$H NMR (250 MHz, CDCl$_3$) δ 1.44–1.62 (1H, m), 1.80–1.94 (2H, m), 2.02–2.20 (2H, m), 2.62–2.76 (1H, m), 3.06–3.27 (2H, m), 3.70 (3H, s), 3.76–3.86 (2H, m), 4.02–4.15 (2H, m), 6.48 (1H, d, J=2.0 Hz), 6.6 (1H, d, J=9.0 Hz), 7.0 (1H, s), 7.24–7.36 (4H, m), 7.62 (2H, d, J=8.0 Hz), and (7.86, 1H, s). m/z (ES$^+$) 391 (M+1).

EXAMPLE 53A (5R,6S)-3-[2-Isopropoxy-5-(oxazol-5-yl)phenyl]-6-phenyl-1-oxa-7-(tert-butoxycarbonyl)aza-spiro[4.5]dec-3-ene Prepared from the compound of Description 53 and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 7.86 (1H, s), 7.56–7.22 (8H, m), 6.92 (1H, d, J=8.7 Hz), 6.62 (1H, t, J=2.0 Hz), 5.10 (1H, s), 5.03 (1H, dd, J=12.2, 2.0 Hz), 4.76–4.64 (2H, m), 4.10 (1H, m), 3.14 (1H, m), 2.13–1.60 (4H, m), and 1.44–1.22 (15H, m). m/z (ES$^+$) 517 (M+1).

EXAMPLE 53B (5R,6S)-3-[2-Isopropoxy-5-(oxazol-5-yl)phenyl]-6-phenyl-1-oxa-7-aza-spiro[4.5]dec-3-ene Prepared from the compound of Example 53A according to the method of Example 1B. $^1$H NMR (250 MHz, CDCl$_3$) δ 1.27 (6H, d, J=6.0 Hz), 2.80–1.98 (2H, m), 2.02–1.99 (1H, m), 2.50–2.42 (1H. br s), 2.94–2.86 (1H, br s), 3.50–3.48 (1H, br d, J=17.0 Hz), 4.12 (1H, s), 4.5 (2H, m), 4.98 (1H, br d, J=12.4 Hz), 6.03 (1H, br s), 6.81 (1H, d, J=8.8 Hz), 7.08 (iH, d, J=2.1 Hz), 7.22 (4H, m), 7.4 (1H, dd, J=8.6, 2.2 Hz), 7.56 (2H, m), and 7.85 (1H, s). m/z (ES$^+$) 417 (M+1).

EXAMPLE 54

(3S,5R,6S)-3-[2-Isopropoxy-5-(oxazol-5-yl)phenyl]-6-phenyl-1-oxa-7-aza-spiro[4.5]decane Prepared from the compound of Example 53B according to the method of Example 2. $^1$H NMR (250 MHz, CDCl$_3$) δ 1.19 (1H, m), 1.24 (3H, d, J=6 Hz), 1.30 (3H, d, J=6.0 Hz), 1.50–2.01 (2H, m), 2.16 (1H, br d, J=9.0 Hz), 2.43 (1H, br s), 2.90 (1H, br s), 3.15 (1H, dd, J=8.3 Hz, 10.3 Hz), 3.50–3.42 (1H, br d, J=7.0 Hz), 3.94–3.82 (1H, m), 3.99–4.10 (2H, m), 4.52 (1H, septet, J=6 Hz), 6.53 (1H, s), 6.81 (1H, d, J=8.5 Hz), 7.0 (1H, s), 7.43–7.22 (4H, m), 7.76–7.63 (1H, br s), and 7.83 (1H, s). m/z (ES) 419 (M+1).

EXAMPLE 55A (5R,6S)-3-[2-Benzyloxy-5-(2-trifluoromethyl-1H-imidazol-1-yl)phenyl]-6-phenyl-1-oxa-7-(tert-butoxycarbonyl) aza-spiro[4.5]dec-3-ene Prepared from the compound of Description 57 and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 1.32 (9H, s), 1.71–1.84 (4H, m), 2.03–2.13 (1H, m), 3.04–3.16 (IH, m), 4.05–4.13 (1H, m), 4.60 (1H, dd), 4.91 (1H, dd), 5.09 (1H, s), 5.17(2H, q), 6.70 (1H, t), 7.04 (2H, dd), 7.11 (1H, d), 7.15–7.28 (5H, m), and 7.35–7.49 (7H, m).

EXAMPLE 55B (5R,6S)-3-[2-Benzyloxy-5-(2-trifluoromethyl-1H-imidazol-1-yl)phenyl]-6-phenyl-1-oxa-7-aza-spiro[4.5]dec-3-ene Prepared from the compound of Example 55A according to the method of Example 1B. m/z (ES$^+$) 532 (M+1).

EXAMPLE 56

(3S,5R,6S)-3-[2-Hydroxy-5-(2-trifluoromethyl-1H-imidazol-1-yl)phenyl]-6-phenyl-1-oxa-7-aza-spiro[4.5]decane Hydrochloride Prepared from the compound of Example 55B according to the method of Example 2. $^1$H NMR (360 MHz, DMSO-d$_6$) δ 1.66 (1H, t, J=12 Hz), 1.70–1.81 (2H, m), 1.91–2.10 (3H, m), 3.03–3.071 (1H, m), 3.10 (1H, t, J=8 Hz), 3.25–3.28 (1H, m), 3.820 (1H, qn, J=10 Hz), 4.15 (1H, t, J=7.2 Hz), 4.45 (1H, d, J=10.8 Hz), 5.97 (1H, d, J=2 Hz), 6.90 (1H, d, J=8.6 Hz), 7.03 (1H, dd, J=7, 2 Hz), 7.10 (1H, t, J=7.5 Hz), 7.23 (1H, d, J=1 Hz), 7.28 (1H, t, J=8 Hz), 7.42 (1H, d, J=1 Hz), and 7.51 (1H, d, J=7H). m/z (ES$^+$) 444 (M+1).

EXAMPLE 57A (5R,6S)-3-[5-(1-Methyl-1H-1,2,3-triazol-3-yl)-2-(trifluoromethoxy)phenyl]-6-phenyl-1-oxa-7-(tert-butoxycarbonyl)aza-spiro[4.5]dec-3-ene Prepared from 1-methyl-4-[3-bromo-4-(trifluoromethoxy)phenyl]-1H-1,2,3-triazole (Description 60) and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 7.75 (1H, s), 7.74–7.67 (2H, m), 7.50–7.40 (2H, m), 7.35–7.19 (4H, m), 6.57 (1H, t, J=2.1 Hz), 5.15 (1H, br s), 4.96 (1H, dd, J=12, 2.1 Hz), 4.65 (1H, dd, J=12, 2.1 Hz), 4.17 (3H, s), 4.15–4.05 (1H, m), 3.23–3.08 (1H, m), 2.18–2.05 (1H, m), 1.95–1.75 (3H, m), and 1.35 (9H, s). m/z (ES$^+$) 557 (M+1).

EXAMPLE 57B (5R,6S)-3-[5-(1-Methyl-1H-1,2,3-triazol-3-yl)-2-(trifluoromethoxy)phenyl]-6-phenyl-1-oxa-7-aza-spiro[4.5]dec-3-ene Prepared from the compound of Example 57A according to the method of Example 1B. $^1$H NMR (250 MHz, CDCl$_3$) δ 7.68 (1H, s), 7.60 (1H, dd, J=8.5, 2.2 Hz), 7.42–7.35 (3H, m), 7.26–7.10 (4H, m), 6.15 (1H, t, J=2.1 Hz), 4.88 (1H, dd, J=12, 2.1 Hz), 4.42 (1H, dd. J=12, 2.1 Hz), 4.15 (3H, s), 3.78 (1H, s), 3.35–3.20 (1H, m), 2.84 (1H, dt, J=12, 2.8 Hz). and 2.12–1.60 (4H, m). m/z (ES$^+$) 457 (M+1).

EXAMPLE 58

(3S,5R,6S)-3-[5-(1-Methyl-1H-1,2,3-triazol-3-yl)-2-(trifluoromethoxy)phenyl]-6-phenyl-1-oxa-7-aza-spiro[4.5]decane Prepared from the compound of Example 57B according to the method of Example 2. $^1$H NMR (250 MHz, CDCl$_3$) δ 7.73 (1H, dd, J=8.5, 2.1 Hz), 7.60–7.50 (2H, m), 7.42 (IH, s), 7.41–7.25 (3H, m), 7.18 (1H, dq, J=8.5, 1.5 Hz), 6.63 (1H, d, J=2.1 Hz), 4.19 (3H, s), 4.13 (1H, t, J=8.0 Hz), 3.91–3.74 (1H, m), 3.70 (1H, s), 3.35–3.20 (2H, m), 2.84 (1H, dt, J=12, 3 Hz), 2.20–1.80 (4H, m), and 1.70–1.55 (2H, m). m/z (ES$^+$) 459 (M+1).

EXAMPLE 59A (5R,6S)-3-[5-(2-Methyl-2H-1,2,3-triazol-3-yl)-2-(trifluoromethoxy)phenyl]-6-phenyl-1-oxa-7-(tert-butoxycarbonyl)aza-spiro[4.5]dec-3-ene Prepared from 2-Methyl-4-[3-bromo-4-(trifluoromethoxy)phenyl]-2H-1,2,3-triazole (Description 60) and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz, CDCl$_3$) δ 7.79 (1H, s), 7.67 (1H, dd, J=8.5, 2.1 Hz), 7.63 (1H, d, J=2.1 Hz), 7.50–7.44 (2H, m), 7.36–7.18 (4H, m), 6.57 (1H, t, J=2.1 Hz), 5.18 (1H, br s), 4.98 (1H, dd, J=12, 2.1 Hz), 4.66 (1H, dd, J=12, 2.1 Hz), 4.25 (3H, s), 4.20–4.10 (1H, m), 3.20–3.05 (1H, m), 2.20–2.05 (1H, m), 1.95–1.78 (3H, m), and 1.37 (9H, s). m/z (ES$^+$) 557 (M+1).

EXAMPLE 59B (5R,6S)-3-[5-(2-Methyl-2H-1,2,3-triazol-3-yl)-2-(trifluoromethoxy)phenyl]-6-phenyl-1-oxa-7-aza-spiro[4.5]dec-3-ene Prepared from the compound of Example 59A according to the method of Example 1B. $^1$H NMR (250 MHz, CDCl$_3$) δ 7.73 (1H, s), 7.58 (1H, dd, J=8.5, 2.2 Hz), 7.42–7.34 (2H, m), 7.30–7.10 (5H, m), 6.12 (1H, t, J=2.1 Hz), 4.89 (1H, dd, J=12, 2.1 Hz), 4.40 (1H, dd, J=12, 2.1 Hz), 4.23 (3H, s), 3.79 (1H, s), 3.35–3.20 (1H, m), 2.84 (1H, dt, J=12, 2.9 Hz), and 2.15–1.60 (4H, m), m/z (ES$^+$) 457 (M+1).

EXAMPLE 60

(3S,5R,6S)-3-[5-(2-Methyl-2H-1,2,3-triazol-3-yl)-2-(trifluoromethoxy)phenyl]-6-phenyl-1-oxa-7-aza-spiro[4.5]decane Prepared from the compound of Example 59B according to the method of Example 2. $^1$H NMR (250 MHz, CDCl$_3$) δ 7.62–7.51 (3H, m), 7.49 (1H, s), 7.42–7.36 (3H, m), 7.17 (1H, dq, J=8.5, 1.5 Hz), 6.65 (1H, d, J=2.1 Hz), 4.24 (3H, s), 4.10 (1H, t, J=7.9 Hz), 3.92–3.74 (1H, m), 3.69 (1H, s), 3.32–3.22 (2H, m), 2.84 (1H, dt, J=12, 3 Hz), 2.20–1.85 (4H, m), and 1.69–1.56 (2H, m). m/z (ES$^+$) 459 (M+1).

EXAMPLE 61A (5R,6S)-3-[5-(Pyrid-3-yl)-2-(trifluoromethoxy)phenyl]-6-phenyl-1-oxa-7-(tert-butoxycarbonyl)aza-spiro[4.5]dec-3-ene Prepared from the compound of Description 62 and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 8.78 (1H, dd, J=4.9, 1.8 Hz), 7.82 (1H, m), 7.48 (3H, m), 7.38 (3H, m), 7.24 (3H, m), 6.55 (1H, t, J=2.1 Hz), 5.16 (1H, s), 4.97 (1H, dd, J=2.1, 12.2 Hz), 4.63 (1H, dd, J=2.1, 12.2 Hz), 4.13 (1H, m), 3.16 (1H, m), 2.15 (1H, m), 1.86 (2H, m), 1.64 (1H, m), 1.34 (9H, s). m/z (ES$^+$) 553 (M+1).

EXAMPLE 61B (5R,6S)-3-[5-(Pyrid-3-yl)-2-(trifluoromethoxy)phenyl]-6-phenyl-1-oxa-7-aza-spiro[4.5]dec-3-ene Hydrochloride (5R,6S)-3-[5-(Pyrid-3-yl)-2-(trifluoromethoxy)phenyl]-6-phenyl-1-oxa-7-(tert-butoxycarbonyl)aza-spiro[4.5]dec-3-ene (Description 61A) (230 mg, 0.42 mmol) was dissolved in diethylether (10 ml). Ethereal HCl (2M, 10 ml) was added and the reaction mixture was stirred at room temperature over night. The solid was collected and dried in vacuo to give the title compound as a solid (175 mg, 92%). $^1$H NMR (360 MHz, DMSO-d$_6$) δ 9.73 (1H, m), 9.14 (1H, m), 8.96 (1H, d, J=2.0 Hz), 8.67 (1H, dd, J=5.1, 1.6 Hz), 8.23 (1H, d, J=7–9 Hz), 7.78 (1H, dd, J=8.6, 2.3 Hz), 7.65 (1H, dd, J=7.9, 5.1 Hz), 7.48 (4H, m), 7.33 (3H, m), 6.42 (1H, t), 4.99 (1H, dd, J=12.5 Hz), 4.66 (1H, d, J=10.4 Hz), 4.50 (1H, ad, J=12.5 Hz), 3.33 (1H, m), 3.13 (1H, m), 2.08 (2H, m), 1.88 (2H, m). m/z (ES$^+$) 453 (M+1).

EXAMPLE 62

(3S,5R,6S)-3-[2-Isoproproxy-5-(pyrid-3-yl)phenyl]-6-phenyl-1-oxa-7-(tert-butoxycarbonyl)aza-spiro[4.5]decane (3S,5R,6S)-3-(5-Bromo-2-isopropoxyphenyl)-6-phenyl-1-oxa-7-(tert-butoxycarbonyl)aza-spiro[4.5]decane (Description 68) (100 mg, 0.19 mmol), 3-(trimethylstannyl) pyridine (Description 63) (60 mg, 0.25 mmol) and lithium chloride (48 mg, 1.14 mmol) were suspended in toluene (5 ml) under a nitrogen atmosphere. Tetrakis (triphenylphosphine) palladium (0) (20 mg, 0.017 mmol) was added and the solution was stirred at 100° C. for 16 hours, allowed to cool to ambient temperature and filtered. The filtrate was washed with water, dried (Na$_2$SO$_4$) and the solvent was evaporated under reduced pressure. The residue was purified by flash column chromatography on silica gel, eluting with hexane/EtOAc (80:20) to give the title compound as an oil (33 mg). $^1$H NMR (360 MHz, CDCl$_3$) δ 8.78 (1H, s), 8.56–8.52 (1H, m), 7.80–7.78 (1H, m), 7.57–7.54 (2H, m), 7.40–7.37 (2H, m), 7.31–7.20 (4H, m), 6.95–6.94 (1H, d, J=8.3 Hz), 5.24 (1H, s), 4.65–4.58 (1H, m), 4.31–4.26 (1H, m), 4.03–3.97 (1H, m), 3.87–3.82 (1H, m), 3.74–3.69 (1H, m), 2.94–2.87 (1H, m), 2.44–2.39 (1H, m), 2.31–2.14 (2H, m), 1.81–1.75 (3H, m), 1.40–1.36 (6H, m), and 1.32 (9H, s). MS (ES$^+$) 529 (M+1).

EXAMPLE 63

(3S,5R,6S)-3[-2-Isopropoxy-5-(pyrid-3-yl)phenyl]-6-phenyl-1-oxa-7-aza-spiro [4.5]decane Dihydrochloride (3S,5R,6S)-3-[2-Isopropoxy-5-(pyrid-3-yl)phenyl]-6-phenyl-1-oxa-7-(tert-butoxycarbonyl)aza-spiro[4.5]decane (Description 62) (29 mg, 0.05 mmol) was dissolved in diethyl ether (2 ml). Ethereal hydrochloric acid (1M, 2 ml) was added and the solution was stirred for 16 hours. The solid was collected and dried in vacuo to give the title compound as a solid (13 mg). $^1$H NMR (360 MHz, CDCl$_3$) δ 9.70–9.67 (1H, m), 9.03–8.97 (1H, m), 8.84–8.78 (1H, m), 8.34–8.32 (1H, m), 8.01–8.00 (1H, m), 7.59–7.57 (3H, m), 7.47–7.43 (2H, m), 7.39–7.38 (1H, m), 7.11–7.08 (1H, d, J=8.8 Hz), 6.60–6.59 (1H, d, J=2.2 Hz), 4.67–4.63 (1H, m), 4.52–4.49 (1H, m), 4.18–4.14 (1H, m), 3.83–3.81 (1H, m), 2.25–2.22 (2H, m), 3.13–3.07 (1H, m), 2.13–2.07 (3H, m), 1.82–1.75 (3H, m), and 1.27–1.22 (6H, m). MS (ES$^+$) 429 (M+1).

EXAMPLE 64A (5R,6S)-3-[2-Methoxy-5-(1H-1,2,4-triazol-1-yl)phenyl]-6-phenyl-1-oxa-7-(tert-butoxycarbonyl)aza-spiro[4.5]dec-3-ene Prepared from 1-(3-bromo-4-methoxyphenyl)-1H-1,2,4-triazole (Description 70) and (5R,6S)-3-tributylstannyl-6-phenyl-1-oxa-7-(tert-butoxycarbonyl)aza-spiro[4.5]dec-3-ene according to the method of Example 1A. $^1$H NMR (360 MHz, CDCl$_3$) δ 1.31 (9H, s), 1.78 –1.88 (3H, m), 2.08–2.14 (1H, m), 3.10–3.16 (1H, m), 3.91 (3H, s), 4.09–4.15 (1H, m), 4.64 (1H, dd, J=12.1, 2.1 Hz), 4.99 (1H, dd, J=12.0, 2.0 Hz), 5.17 (1H, S), 6.69 (1H, t, J=2.0 Hz), 7.00 (1H, d, J=8.9 Hz), 7.18–7.28 (3H, m), 7.33 (1H, d, J=2.6 Hz), 7.45–7.57 (3H, m), 8.08 (1H, s), and 8.44 (1H, s). m/z (ES$^+$) 489 (M+1).

EXAMPLE 64B (5R,6S)-3-[2-Methoxy-5-(1H-1,2,4-triazol-1-yl)phenyl]-6-phenyl-1-oxa-7-aza-spiro[4.5]dec-3-ene Prepared from the compound of Example 64A according to the method of Example 1B. $^1$H NMR (250 MHz, CDCl$_3$) δ 1.64–1.68 (1H, m), 1.96–2.05 (3H, m), 2.83 (1H, dt, J=12.4, 2.8 Hz), 3.26–3.29 (1H, m), 3.78 (1H, s), 3.82 (3H, s), 4.35 (1H, dd, J=11.9, 2.2 Hz), 4.88 (1H, dd, J=11.9, 2.1 Hz), 6.19 (1H, t, J=2.0 Hz), 6.89 (1H, d, J=8.8 Hz), 7.04 (1H, d, J=2.7 Hz), 7.11–7.21 (3H, m), 7.36–7.42 (3H, m), 8.05 (1H, s), and 8.35 (1H, s). m/z (ES$^+$) 389 (M+1).

EXAMPLE 65

(3S,5R,6S)-3-[2-Methoxy-5-(1H-1,2,4-triazol-1-yl)phenyl]-6-phenyl-1-oxa-7-aza-spiro[4.5]decane Hydrochloride Prepared from the compound of Example 64B according to the method of Example 2. $^1$H NMR (360 MHz, D$_2$O) δ 1.82–1.94 (3H, m), 2.06–2.19 (3H, m), 3.21 (1H, m), 3.48–3.55 (2H, m), 3.71 (3H, s), 3.84 (1H, m), 4.10–4.13 (1H, m), 4.37 (1H, s), 6.41 (1H, s), 6.94 (1H, d, J=8.4 Hz), 7.23–7.33 (4H, m), 7.47 (2H, d, J=7.1 Hz), 8.34 (1H, s), and 8.78 (1H, s). m/z (ES$^+$) 391 (M+1).

EXAMPLE 66A (5R,6S)-3-[5-(Pyrimidin-5-yl)-2-(trifluoromethoxy)phenyl]-6-phenyl-1-oxa-7-(tert-butoxycarbonyl)aza-spiro[4.5]dec-3-ene Prepared from the compound of Description 72 and (5R,6S)-3-tributylstannyl-6-phenyl-1-oxa-7-(tert-butoxycarbonyl)aza-spiro[4.5]dec-3-ene according to the method of Example 1A. $^1$H NMR (250 MHz CDCl$_3$) δ 0.85 (1H, d, J=7.6 Hz), 1.35 (9H, s), 1.84 (2H, m), 2.12 (1H, m), 3.2 (1H, m), 4.12 (2H, q, J=7.1 Hz), 4.61 (1H, dd, J=17.1, 2.1 Hz), 4.95 (1H, dd, J=17.0, 1.9 Hz), 5.16 (1H, s), 6.57 (1H, s), 7.29 (5H, m), 7.51 (3H, m), 8.91 (2H, s), and 9.25 (1H, s). m/z (ES$^+$) 554 (M+1).

EXAMPLE 66B (5R,6S)-3-[5-(pyrimidin-5-yl)-2-(trifluoromethoxy)phenyl]-6-phenyl-1-oxa-7-aza-spiro[4.5]dec-3-ene Prepared from the compound of Example 66A according to the method of Example 1B. $^1$H NMR (250 MHz, CDCl$_3$) δ 1.85 (2H, t, J=11.9 Hz), 2.93 (1H, t, J=11.5 Hz), 3.52 (1H, d, J=12.0 Hz), 4.46 (1H, dd, J=12.6, 2.1 Hz), 4.92 (1H, dd, J=12.6, 2.1 Hz), 5.99 (1H, s), 6.98 (1H, d, J=2.2 Hz), 7.3 (5H, m), 7.43 (1H, dd, J=8.56, 6.3 Hz), 7.55 (1H, dd, J=6.0, 1.8 Hz), 8.8 (2H, s), 9.23 (1H, s). m/z (ES$^+$) 454 (M+1).

We claim:

1. A compound of the formula (I):

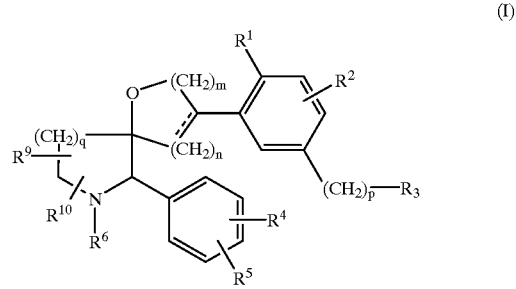

wherein

R$^1$ represents a halogen atom, a hydroxy group, a C$_{1-6}$alkyl group optionally substituted by one to three fluorine atoms, a C$_{1-6}$alkoxy group optionally substituted by one to three fluorine atoms, or a C$_{1-6}$alkylthio group optionally substituted by one to three fluorine atoms;

R² represents hydrogen, halogen, C₁₋₆alkyl or C₁₋₆alkoxy;

or when R² is adjacent to R¹, they may be joined together such that there is formed a 5- or 6-membered saturated or unsaturated ring which is selected from 2,3-dihydrobenzofuranyl, benzofuranyl, 3,4-dihydro-2H-1-benzopyranyl, 2H-1-benzopyranyl, 1,3-benzodioxolyl, and 1,4-benzodioxanyl;

R³ represents a 5- or 6-membered aromatic heterocyclic group wherein R³ is selected from pyrrolyl, furanyl, thienyl, pyridinyl, pyrazolyl, imidazolyl, oxazolyl, isoxazolyl, pyrazinyl, pyrimidinyl, pyridazinyl, triazolyl, oxadiazolyl, thiadiazolyl, triazinyl, and tetrazolyl, which group is optionally substituted by one or two groups selected from C₁₋₆alkyl, C₁₋₆alkoxy, C₃₋₇cycloalkyl, C₃₋₇cycloalkylC₁₋₄alkyl, trifluoromethyl, OCF₃, NO₂, CN, SR$^a$, SOR$^a$, SO₂R$^a$, COR$^a$, CO₂R$^a$, phenyl, —(CH₂)$_r$NR$^a$R$^b$, —(CH₂)$_r$NR$^a$COR$^b$, —(CH₂)$_r$CONR$^a$R$^b$, or CH₂C(O)R$^a$, where R$^a$ and R$^b$ are each independently hydrogen or C₁₋₄alkyl and r is zero, 1 or 2;

or R⁷, R⁸ and the nitrogen atom to which they are attached form a non-aromatic azabicyclic ring system selected from 5-azabicyclo[2.1.1]hexyl, 5-azabicyclo[2.2.1]heptyl, 6-azabicyclo[3.2.1]octyl, 2-azabicyclo[2.2.2] octyl, 6-azabicyclo[3.2.2]nonyl, 6-azabicyclo[3.3.1] nonyl, 6-azabicyclo[3.3.2]decyl, 7-azabicyclo[4.3.1] decyl, 7-azabicyclo[4.4.1]undecyl and 8-azabicyclo [5.4.1]dodecyl;

or Z, R⁷ and the nitrogen atom to which they are attached form a heteroaliphatic ring selected from pyrrolidinyl, piperidyl, morpholinyl, thiomorpholinyl and piperazinyl;

R⁹ and R¹⁰ each independently represent hydrogen, halogen, C₁₋₆alkyl, CH₂OR$^d$, oxo, CO₂R$^a$ or CONR$^a$R$^b$ where R$^a$ and R$^b$ are as previously defined and R$^d$ represents hydrogen, C₁₋₆alkyl or phenyl;

R¹² represents OR$^a$, CONR$^a$R$^b$ or heteroaryl wherein heteroaryl is selected from pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl;

R¹³ represents H or C₁₋₆alkyl;

m is zero 1, 2 or 3;

n is zero, 1, 2, or 3, with the proviso that the sum total of m+n is 2 or 3;

p is zero or 1;

q is 2; and when m is 1 and n is 1 or 2, the broken line represents an optional double bond;

or a pharmaceutically acceptable salt thereof.

2. A compound as claimed in claim 1 wherein R¹ represents a C₁₋₆alkyl group optionally substituted by one to three fluorine atoms, or a C₁₋₆alkoxy group optionally substituted by one to three fluorine atoms.

3. A compound as claimed in claim 1 wherein

R¹ represents a C₁₋₆alkyl group optionally substituted by one to three fluorine atoms, or a C₁₋₆alkoxy group optionally substituted by one to three fluorine atoms;

R² represents hydrogen, halogen, C₁₋₆alkyl or C₁₋₆alkoxy;

R³ represents a 5- or 6-membered aromatic heterocyclic group wherein R³ is selected from pyrrolyl, furanyl, thienyl, pyridinyl, pyrazolyl, imidazolyl, oxazolyl, isoxazolyl, pyrazinyl, pyrimidinyl, pyridazinyl, triazolyl, oxadiazolyl, thiadiazolyl, triazinyl, and tetrazolyl, which group is optionally substituted by a group selected from C₁₋₆alkyl, C₁₋₆alkoxy, C₃₋₇cycloalkyl, C₃₋₇cycloalkylC₁₋₄alkyl, trifluoromethyl, OCF₃, NO₂, CN, SR$^a$, SOR$^a$, SO₂R$^a$, COR$^a$, CO₂R$^a$, phenyl, —(CH₂)$_r$NR$^a$R$^b$, —(CH₂)$_r$NR$^a$COR$^b$, —(CH₂)$_r$CONR$^a$R$^b$, or CH₂C(O)R$^a$, where R$^a$ and R$^b$ are each independently hydrogen or C₁₋₄alkyl and r is zero, 1 or 2; and R⁶ represents hydrogen, COR$^a$, CO₂R$^a$, COCONR$^a$R$^b$, COCO₂R$^a$, C₁₋₆alkyl optionally substituted by a group selected from (CO₂R$^a$, CONR$^a$R$^b$, hydroxy, CN, COR$^a$, NR$^a$R$^b$, C(NOH)NR$^a$R$^b$, CONHphenyl(C₁₋₄ alkyl), COCO₂R$^a$, CONHNR$^a$R$^b$, C(S)NR$^a$R$^b$, CONR$^a$C₁₋₆alkylR¹², CONR¹³C₂₋₆alkenyl, CONR¹³C₂₋₆alkynyl, COCONR$^a$R$^b$, CONR$^a$C(NR$^b$) NR$^a$R$^b$, CONR$^a$heteroaryl, wherein heteroaryl is selected from imidazolyl and triazolyl optionally substituted by =O and optionally substituted by a group of the formula ZNR⁷R⁸, and phenyl optionally substituted by one, two or three substituents selected from C₁₋₆alkyl, C₁₋₆alkoxy, halogen and trifluoromethyl or C₁₋₆alkyl, optionally substituted by oxo, substituted by a 5-membered heterocyclic ring containing 2 or 3 nitrogen atoms selected from imidazolyl and triazolyl wherein the heterocyclic ring is optionally substituted by =O or =S and wherein the heterocyclic ring is optionally substituted by a group of the formula ZNR⁷R⁸ where Z, R⁷ and R⁸ are as previously defined in claim 1;

or a pharmaceutically acceptable salt thereof.

4. A compound as claimed in claim 1 of formula (I'):

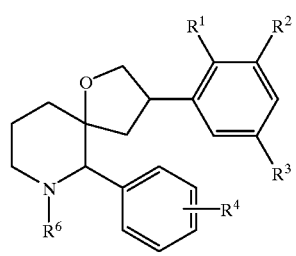

(I')

wherein

R¹ represents a C₁₋₆alkyl group optionally substituted by one to three fluorine atoms, or a C₁₋₆alkoxy group optionally substituted by one to three fluorine atoms;

R² represents hydrogen or halogen;

R³ represents an N-linked tetrazolyl group optionally substituted by a group selected from C₁₋₆alkyl, C₃₋₇cycloalkyl, C₃₋₇cycloalkylC₁₋₄alkyl, trifluoromethyl, SR$^a$, SOR$^a$, SO₂R$^a$, phenyl NR$^a$R$^b$, NR$^a$COR$^b$ or CH₂C(O)R$^a$, where R$^a$ and R$^b$ are each independently hydrogen or C₁₋₄alkyl;

R⁴ represents hydrogen or halogen;

R⁶ represents hydrogen, COR$^a$, CO₂R$^a$, COCONR$^a$R$^b$, COCO₂R$^a$, C₁₋₆alkyl optionally substituted by a group selected from (CO₂R$^a$, CONR$^a$R$^b$, hydroxy, CN, COR$^a$, NR$^a$R$^b$, C(NOH)NR$^a$R$^b$, CONHphenyl(C₁₋₄ alkyl), COCO₂R$^a$, CONHNR$^a$R$^b$, C(S)NR$^a$R$^b$, CONR$^a$C₁₋₆alkylR¹², CONR¹³C₂₋₆alkenyl, CONR¹³C₂₋₆alkynyl, COCONR$^a$R$^b$, CONR$^a$C(NR$^b$) NR$^a$R$^b$, CONR$^a$heteroaryl, wherein heteroaryl is selected from imidazolyl and triazolyl optionally substituted by =O and optionally substituted by a group of the formula ZNR$^7$R$^8$, and phenyl optionally substituted by one, two or three substituents selected from C$_{1-6}$alkyl, C$_{1-6}$alkoxy, halogen and trifluoromethyl or C$_{1-6}$alkyl, optionally substituted by oxo, substituted by a 5-membered heterocyclic ring containing 2 or 3 nitrogen atoms selected from imidazolyl and triazolyl wherein the heterocyclic ring is optionally substituted by =O or =S and wherein the heterocyclic ring is optionally substituted by a group of the formula ZNR$^7$R$^8$ where Z is C$_{1-6}$alkylene or C$_{3-6}$cycloalkyl;

R$^7$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a heteroaliphatic ring selected from pyrrolidinyl, piperidinyl, piperazinyl, morpholinyl, and thiomorpholinyl;

or R$^7$, R$^8$ and the nitrogen atom to which they are attached form a heteroaliphatic ring selected from azetidinyl, pyrrolidinyl, piperidyl, morpholinyl, thiomorpholinyl and piperazinyl, which is optionally substituted by one or two groups selected from hydroxy or C$_{1-4}$alkoxy optionally substituted by a C$_{1-4}$alkoxy or hydroxyl group;

or R$^7$, R$^8$ and the nitrogen atom to which they are attached form a non-aromatic azabicyclic ring system selected from 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.3.2]decyl, 7-azabicyclo[4.3.1]decyl, 7-azabicyclo[4.4.1]undecyl and 8-azabicyclo[5.4.1]dodecyl;

or Z, R$^7$ and the nitrogen atom to which they are attached form a heteroaliphatic ring selected from pyrrolidinyl, piperidyl, morpholinyl, thiomorpholinyl and piperazinyl;

R$^{12}$ represents OR$^a$, CONR$^a$R$^b$ or heteroaryl wherein heteroaryl is selected from pyrrolyl, furanyl, thienyl, pyridyl, pyrazolyl, imidazolyl, oxazolyl, isoxazolyl, thiazolyl, isothiazolyl, pyrazinyl, pyriridinyl, pyridazinyl, triazolyl, oxadiazolyl, thiadiazolyl, triazinyl, and tetrazolyl;

R$^{13}$ represents H or C$_{1-6}$alkyl;

or a pharmaceutically acceptable salt thereof.

5. A compound as claimed in claim 1 wherein R$^1$ is a methyl, trifluoromethyl, methoxy, ethoxy, isopropoxy or trifluoromethoxy group.

6. A compound as claimed in claim 1 wherein R$^2$ is a hydrogen, fluorine or chlorine atom.

7. A compound as claimed in claim 1 wherein R$^3$ is the group

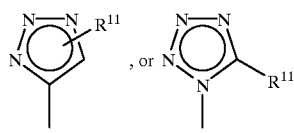

where R$^{11}$ is hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, COR$^a$, CO$_2$R$^a$, (CH$_2$)$_r$CONR$^a$R$^b$, (CH$_2$)$_r$NR$^a$R$^b$ or (CH$_2$)$_r$NR$^a$COR$^b$, where R$^a$ and R$^b$ are hydrogen or C$_{1-4}$alkyl, and r is zero, 1 or 2.

8. A compound as claimed in claim 1 wherein R$^4$ is a hydrogen atom or a fluorine atom.

9. A compound as claimed in claim 1 wherein R$^5$ is a hydrogen atom.

10. A compound as claimed in claim 1 wherein R$^6$ is a hydrogen atom.

11. A compound as claimed in claim 1 wherein R$^9$ and R$^{10}$ are both hydrogen atoms.

12. A compound as claimed in claim 1 wherein m is 1.

13. A compound as claimed in claim 1 wherein n is 1 or 2.

14. A compound as claimed in claim 1 wherein p is zero.

15. A compound as claimed in claim 1 wherein q is 2.

16. A compound selected from:

(6S,5R,3S)-3-(2-methoxy-5-(5-trifluoromethyl)tetrazol-1-yl)phenyl)-6-phenyl-1-oxa-7-aza-spiro[4.5]decane;

(6S,5R,3S)-3-(2-isopropoxy-5-(5-(trifluoromethyl)tetrazol-1-yl)phenyl)-6-phenyl-1-oxa-7-aza-spiro[4.5]decane;

(6S,5R,3S)-3-(2-methoxy-5-(tetrazol-1-yl)phenyl)-6-phenyl-1-oxa-7-aza-spiro[4.5]decane;

(6S,5R,3S)-3-(2-methyl-5-(5-(trifluoromethyl)tetrazol-1-yl)phenyl)-6-phenyl-1-oxa-7-aza-spiro[4.5]decane;

(6S,5R,3S)-3-(2-trifluoromethoxy-5-(5-(trifluoromethyl)tetrazol-1-yl)phenyl)-6-phenyl-1-oxa-7-aza-spiro[4.5]decane;

(6S,5R,3S)-3-(2-methoxy-3-fluoro-5-(5-(trifluoromethyl)tetrazol-1-yl)phenyl)-6-phenyl-1-oxa-7-aza-spiro[4.5]decane;

(6S,5R,3S)-3-(2-methoxy-5-(1,2,4-triazol-4yl)phenyl)-6-phenyl-1-oxa-7-aza-spiro[4.5]decane;

(6S,5R,3S)-3-(2-methoxy-4-fluoro-5-(5-(trifluoromethyl)tetrazol-1-yl)phenyl)-6-phenyl-1-oxa-7-aza-spiro[4.5]decane;

(6S,5R,3S)-6-phenyl-3-(2-methoxy-5-(3,5-bis(trifluoromethyl)-1,2,4-triazol-4-yl)phenyl)-1-oxa-7-aza-spiro[4.5]dec-3-ene;

(6S,5R,3S)-6-phenyl-3-(5-(5-trifluoromethyl)tetrazol-1-yl)-2,3-dihydrobenzfuran-7-yl)-1-oxa-7-aza-spiro[4.5]decane;

(6S,5R,3S)-6-phenyl-3-(5-(5-trifluoromethyl)tetrazol-1-yl)-2,3-dihydrobenzfuran-7-yl)-1-oxa-7-aza-spiro[4.5]dec-3-ene;

(6S,5R,3S)-6-phenyl-3-(2-methoxy-5-(3,5-bis(trifluoromethyl)-1,2,4-triazol-4-yl)phenyl)-1-oxa-7-aza-spiro[4.5]decane;

(6S,5R,3S)-6-phenyl-3-(2-methoxy-5-(5-trifluoromethyl)isoxazol-4-yl)phenyl)-1-oxa-7-aza-spiro[4.5]dec-3-ene;

(6S,5R,3S)-6-phenyl-3-(2-methoxy-5-(5-trifluoromethyl)isoxazol-4-yl)phenyl)-1-oxa-7-aza-spiro[4.5]decane;

(6S,5R,3S)-7-((2,3-dihydro-3-oxo-1,2,4-triazol-5-yl)methyl)-3-(2-methoxy-5-(5-(trifluoromethyl)tetrazol-1-yl)phenyl)-6-phenyl-1-oxa-7-aza-spiro[4.5]decane;

(6S,5R,3S)-7-(2-(N,N-dimethylamino)ethyl)-3-(2-methoxy-5-(5-(trifluoromethyl)tetrazol-1-yl)phenyl)-6-phenyl-1-oxa-7-aza-spiro[4.5]decane;

(6S,5R,3S)-7-((1H-imidazol-5-yl)methyl)-3-(2-methoxy-5-(5-(trifluoromethyl)tetrazol-1-yl)phenyl)-6-phenyl-1-oxa-7-aza-spiro[4.5]decane;

(5R,6S)-3-[2-methoxy-5-(2,4-dimethyl-1H-imidazol-1-yl)phenyl]-6-phenyl-1-oxa-7-(tert-butoxycarbonyl)aza-spiro[4.5]dec-3-ene;

(5R,6S)-3-[2-methoxy-5-(2,4-dimethyl-1H-imidazol-1-yl)phenyl]-6-phenyl-1-oxa-7-aza-spiro[4.5]dec-3-ene;

(3S,5R,6S)-3-[2-methoxy-5-(2,4-dimethyl-1H-imidazol-1-yl)phenyl]-6-phenyl-1-oxa-7-aza-spiro[4.5]decane;

(5R,6S)-3-[2-methoxy-5-(4-pyridyl)phenyl]-6-phenyl-1-oxa-7-(tert-butoxycarbonyl)aza-spiro[4.5]dec-3-ene:

(5R,6S)-3-[2-methoxy-5-(4-pyridyl)phenyl]-6-phenyl-1-oxa-7-aza-spiro[4.5]dec-3-ene;

(3S,5R,6S)-3-[2-methoxy-5-(4-pyridyl)phenyl]-6-phenyl-1-oxa-7-aza-spiro[4.5]decane;

(5R,6S)-3-[5-(4-pyridyl)-2-(trifluoromethoxy)phenyl]-6-phenyl-1-oxa-7-(tert-butoxycarbonyl)aza-spiro[4.5]dec-3-ene;

(5R,6S)-3-[5-(4-pyridyl)-2-(trifluoromethoxy)phenyl]-6-phenyl-1-oxa-7-aza-spiro[4.5]dec-3-ene;

(5R,6S)-3-[5-(4H-1,2,4-triazol-4-yl)-2-(trifluoromethoxy)phenyl]-6-phenyl-1-oxa-7-(tert-butoxycarbonyl)aza-spiro[4.5]dec-3-ene;

(5R,6S)-3-[5-(4H-1,2,4-triazol-4-yl)-2-(trifluoromethoxy)phenyl]-6-phenyl-1-oxa-7-aza-spiro[4.5]dec-3-ene;

(3S,5R,6S)-3-[5-(4H-1,2,4-triazol-4-yl)-2-(trifluoromethoxy)phenyl]-6-phenyl-1-oxa-7-aza-spiro[4.5]decane;

(5R,6S)-3-[2-(trifluoromethoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;

(5R,6S)-3-[2-(trifluoromethoxy-5-(3-trifluoromethyl-4H-1,2,4-triazol-4-yl)phenyl]-6-phenyl-1-oxa-7-aza-spiro[4.5]dec-3-ene;

(3S,5R,6S)-3-[2-(trifluoromethoxy-5-(3-trifluoromethyl-4H-1,2,4-triazol-4-yl)phenyl]-6-phenyl-1-oxa-7-aza-spiro[4.5]decane;

(5R,6S)-3-[2-methoxy-5-(2-trifluoromethyl-1H-imidazol-1-yl)phenyl]-6-phenyl-1-oxa-7-(tert-butoxycarbonyl)aza-spiro[4.5]dec-3-ene;

(5R,6S)-3-[2-methoxy-5-(2-trifluoromethyl-1H-imidazol-1-yl)phenyl]-6-phenyl-1-oxa-7-aza-spiro[4.5]dec-3-ene;

(3S,5R,6S)-3-[2-methoxy-5-(2-trifluoromethyl-1H-imidazol-1-yl)phenyl]-6-phenyl-1-oxa-7-aza-spiro[4.5]decane;

(5R,6S)-3-[2-trifluoromethoxy-5-(2-trifluoromethyl-1H-imidazol-1-yl)phenyl]-6-phenyl-1-oxa-7-(tert-butoxycarbonyl)aza-spiro[4.5]dec-3-ene;

(5R,6S)-3-[2-trifluoromethoxy-5-(2-trifluoromethyl-1H-imidazol-1-yl)phenyl]-6-phenyl-1-oxa-7-aza-spiro[4.5]dec-3-ene;

(3S,5R,6S)-3-[2-trifluoromethoxy-5-(2-trifluoromethyl-1H-imidazol-1-yl)phenyl]-6-phenyl-1-oxa-7-aza-spiro[4.5]decane;

(5R,6S)-3-[2-methoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;

(5R,6S)-3-[2-methoxy-5-(3-trifluoromethyl-4H-1,2,4-triazol-4-yl)phenyl]-6-phenyl-1-oxa-7-aza-spiro[4.5]dec-3-ene;

(3S,5R,6S)-3-[2-methoxy-5-(3-trifluoromethyl-4H-1,2,4-triazol-4-yl)phenyl]-6-phenyl-1-oxa-7-aza-spiro[4.5]decane;

(5R,6S)-3-[2-(2-fluoroethoxy)-5-(5-trifluoromethyl-tetrazol-1-yl)phenyl]-6-phenyl-1-oxa-7-(tert-butoxycarbonyl)aza-spiro[4.5]dec-3-ene;

(5R,6S)-3-[2-(2-fluoroethoxy)-5-(5-trifluoromethyl-tetrazol-1-yl)phenyl]-6-phenyl-1-oxa-7-aza-spiro[4,5]dec-3-ene;

(3S,5R,6S)-3-[2-(2-fluoroethoxy)-5-(5-trifluoromethyl-tetrazol-1-yl)phenyl]-6-phenyl-1-oxa-7-aza-spiro[4.5]decane;

(5R,6S)-3-[2-methoxy-5-(2-methyltetrazol-5-yl)phenyl]-6-phenyl-1-oxa-7-(tert-butoxycarbonyl)aza-spiro[4.5]dec-3-ene;

(5R,6S)-3-[2-methoxy-5-(2-methyltetrazol-5-yl)phenyl]-6-phenyl-1-oxa-7-aza-spiro[4.5]dec-3-ene;

(5R,6S)-3-[2-methoxy-5-(1-methyltetrazol-5-yl)phenyl]-6-phenyl-1-oxa-7-(tert-butoxycarbony-yl)aza-spiro[4.5]dec-3-ene;

(5R,6S)-3-[2-methoxy-5-(1-methyltetrazol-5-yl)phenyl]-6-phenyl-1-oxa-7-aza-spiro[4.5]dec-3-ene;

(3S,5R,6S)-3-[2-methoxy-5-(1-methyltetrazol-5-yl)phenyl]-6-phenyl-1-oxa-7-aza-spiro[4.5]decane;

(5R,6S)-3-[2-chloro-5-(tetrazol-1-yl)phenyl]-6-phenyl-1-oxa-7-(tert-butoxycarbonyl)aza-spiro[4.5]dec-3-ene;

(5R,6S)-3-[2-chloro-5-(tetrazol-1-yl)phenyl]-6-phenyl-1-oxa-7-aza-spiro[4.5]decane;

(5R,6S)-3-[5-(1H-pyrazol-1-yl)-2-(trifluoromethoxy)phenyl]-6-phenyl-1-oxa-7-(tert-butoxycarbonyl)aza-spiro[4.5]dec-3-ene;

(5R,6S)-3-[5-(1H-pyrazol-1-yl)-2-(trifluoromethoxy)phenyl]-6-phenyl-1-oxa-7-aza-spiro[4.5]dec-3-ene;

(5R,6S)-3-[2-ethoxy-5-(2-trifluoromethyl-1H-imidazol-1-yl)phenyl]-6-phenyl-1-oxa-7-(tert-butoxycarbonyl)aza-spiro[4.5]dec-3-ene;

(5R,6S)-3-[2-ethoxy-5-(2-trifluoromethyl-1H-imidazol-1-yl)phenyl]-6-phenyl-1-oxa-7-aza-spiro[4.5]dec-3-ene;

(3S,5R,6S)-3-[2-ethoxy-5-(1H-imidazol-1-yl)phenyl]-6-phenyl-1-oxa-7-aza-spiro[4.5]-decane;

(5R,6S)-3-[2-isopropoxy-5-(3-trifluoromethyl-4H-1,2,4-triazol-4-yl)phenyl]-6-phenyl-1-oxa-7-(tert-butoxycarbonyl)aza-spiro[4.5]dec-3-ene;

(5R,6S)-3-[2-isopropoxy-5-(3-trifluoromethyl-4H-1,2,4-triazol-4-yl)phenyl]-6-phenyl-1-oxa-7-aza-spiro[4.5]dec-3-ene;

(3S,5R,6S)-3-[2-isopropoxy-5-(3-trifluoromethyl-4H-1,2,4triazol-4-yl)phenyl]-6-phenyl-1-oxa-7-aza-spiro[4.5]decane;

(5R,6S)-3-[2-isopropoxy-5-(2-trifluoromethyl-1H-imidazol-1-yl)phenyl]-6-phenyl-1-oxa-7-(tert-butoxycarbonyl)aza-spiro[4.5]dec-3-ene;

(5R,6S)-3-[2-isopropoxy-5-(2-trifluoromethyl-1H-imidazol-1-yl)phenyl]-6-phenyl-1-oxa-7-azaspiro[4.5]dec-3-ene;

(3S,5R,6S)-3-[2-isopropoxy-5-(2-trifluoromethyl-1H-imidazol-1-yl)phenyl]-6-phenyl-1-oxa-7-aza-spiro[4.5]decane;

(5R,6S)-3-[2-methoxy-5-(oxazol-5-yl)phenyl]-6-phenyl-1-oxa-7-(tert-butoxycarbonyl)aza-spiro[4.5dec-3-ene;

(5R,6S)-3-[2-methoxy-5-(oxazol-5-yl)phenyl]-6-phenyl-1-oxa-7-aza-spiro[4.5]dec-3-ene;

(3S,5R,6S)-3-[2-methoxy-5-(oxazol-5-yl)phenyl]-6-phenyl-1-oxa-7-aza-spiro[4.5]decane;

(5R,6S)-3-[2-isopropoxy-5-(oxazol-5-yl)phenyl]-6-phenyl-1-oxa-7-(tert-butoxycarbonyl)aza-spiro[4.5]dec-3-ene;

(5R,6S)-3-[2-isopropoxy-5-(oxazol-5-yl)phenyl]-6-phenyl-1-oxa-7-aza-spiro[4.5]dec-3-ene;

(3S,R,6S)-3-[2-isopropoxy-5-(oxazol-5-yl)phenyl]-6-phenyl-1-oxa-7-aza-spiro[4.5]decane;

(5R,6S)-3-[2-benzyloxy-5-(2-trifluoromethyl-1H-imidazol-1-yl)phenyl]-6-phenyl-1-oxa-7-(tert-butoxycarbonyl)aza-spiro[4.5]dec-3-ene;

(5R,6S)-3-[2-benzyloxy-5-(2-trifluoromethyl-1H-imidazol-1-yl)phenyl]-6-phenyl-1-oxa-7-aza-spiro[4.5]dec-3-ene;

(3S,5R,6S)-3-[2-hydroxy-5-(2-trifluoromethyl-1H-imidazol-1-yl)phenyl]-6-phenyl-1-oxa-7-aza-spiro[4.5]decane;

(5R,6S)-3-[5-(1-methyl-1H-1,2,3-triazol-3-yl)-2-(trifluoromethoxy)phenyl]-6-phenyl-1-oxa-7-(tert-butoxycarbonyl)aza-spiro[4.5]dec-3-ene;

(5R,6S)-3-[5-(1-methyl-1H-1,2,3-triazol-3-yl)-2-(trifluoromethoxy)phenyl]-6-phenyl-1-oxa-7-aza-spiro[4.5]dec-3-ene;

(3S,5R,6S)-3-[5-(1-methyl-1H-1,2,3-triazol-3-yl)-2-(trifluoromethoxy)phenyl]-6-phenyl-1-oxa-7-aza-spiro[4.5]decane;

(5R,6S)-3-[5-(2-methyl-2H-1,2,3-triazol-3-yl)-2-(trifluoromethoxy)phenyl]-6-phenyl-1-oxa-7-(tert-butoxycarbonyl)aza-spiro[4.5]dec-3-ene;
(5R,6S)-3-[5-(2-methyl-2H-1,2,3-triazol-3-yl)-2-(trifluoromethoxy)phenyl]-6-phenyl-1-oxa-7-aza-spiro[4.5]dec-3-ene;
(3S,5R,6S)-3-[5-(2-methyl-2H-1,2,3-triazol-3-yl)-2-(trifluoromethoxy)phenyl]-6-phenyl-1-oxa-7-aza-spiror4.5]decane;
(5R,6S)-3-[5-(pyrid-3-yl)-2-(trifluoromethoxy)phenyl]-6-phenyl-1-oxa-7-(tert-butoxycarbonyl)aza-spiro[4.5]dec-3-ene;
(5R,6S)-3-[5-(pyrid-3-yl)-2-(trifluoromethoxy)phenyl]-6-phenyl-1-oxa-7-aza-spiro[4.5]dec-3-ene;
(3S,5R,6S)-3-[2-isopropoxy-5-(pyrid-3-yl)phenyl]-6-phenyl-1-oxa-7-(tert-butoxycarbonyl)aza-spiro[4.5]decane;
(3S,5R,6S)-3-[2-isopropoxy-5-(pyrid-3-yl)phenyl]-6-phenyl-1-oxa-7-aza-spiro[4.5]decane;
(5R,6S)-3-[2-methoxy-5-(1H-1,2,4-triazol-1-yl)phenyl]-6-phenyl-1-oxa-7-(tert-butoxycarbonyl)aza-spiro[4.5]dec-3-ene;
(5R,6S)-3-[2-methoxy-5-(1H-1,2,4-triazol-1-yl)phenyl]-6-phenyl-1-oxa-7-aza-spiro[4.5]dec-3-ene;
(3S,5R,6S)-3-[2-methoxy-5-(1H-1,2,4-triazol-1-yl)phenyl]-6-phenyl-1-oxa-7-aza-spiro[4.5]decane;
(5R,6S)-3-[5-(pyrimidin-5-yl)-2-(trifluoromethoxy)phenyl]-6-phenyl-1-oxa-7-(tert-butoxycarbonyl)aza-spiro[4.5]dec-3-ene;
(5R,6S)-3-[5-(pyrimidin-5-yl)-2-(trifluoromethoxy)phenyl]-6-phenyl-1-oxa-7-aza-spiro[4.5]dec-3-ene;
or a pharmaceutically acceptable salt thereof.

17. A pharmaceutical composition comprising a compound as claimed claim 1 in association with a pharmaceutically acceptable carrier or excipient.

18. A method for the treatment of pain or inflammation, which method comprises administration to a patient in need thereof of an effective amount of a compound according to claim 1.

19. A method for the treatment of migraine, which method comprises administration to a patient in need thereof of an effective amount of a compound according to claim 1.

20. A method for the treatment of emesis, which method comprises administration to a patient in need thereof of an effective amount of a compound according to claim 1.

21. A method for the treatment of postherpetic neuralgia, which method comprises administration to a patient in need thereof of an effective amount of a compound according to claim 1.

22. A process for the preparation of a compound of formula (I) as claimed in claim 1 which comprises:

(A), where m is 1 and n is 1 or 2, reduction of a compound of formula (I) in which the broken line represents a double bond, i.e. a compound of formula (II)

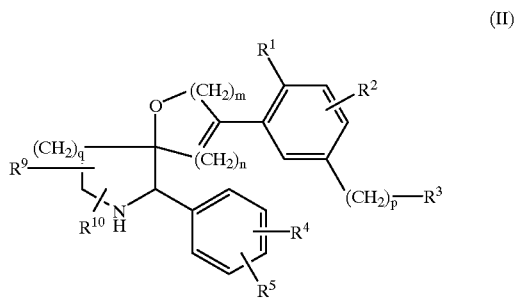

(II)

wherein $R^1$, $R^2$, $R^3$, $R^4$, $R^5$, $R^6$, $R^9$, $R^{10}$, p and q are as defined in claim 1;

to give the compound of formula (I);

the process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I, or a salt thereof, into a pharmaceutically acceptable salt thereof.

* * * * *